(12) United States Patent
Papanicolau et al.

(10) Patent No.: US 10,564,271 B2
(45) Date of Patent: Feb. 18, 2020

(54) SYSTEMS, METHODS AND DEVICES FOR HIGHLY-PARALLELIZED QUS-VALUE DETERMINATION FOR CHARACTERIZING A SPECIMEN

(71) Applicant: EVRIKA RESEARCH TECHNOLOGIES INC., Toronto (CA)

(72) Inventors: Naum Papanicolau, Toronto (CA); Alireza Sadeghian, Markham (CA); Ervis Sofroni, Toronto (CA)

(73) Assignee: EVRIKA RESEARCH TECHNOLOGIES INC., Toronto (CA)

( * ) Notice: Subject to any disclaimer, the term of this patent is extended or adjusted under 35 U.S.C. 154(b) by 229 days.

(21) Appl. No.: 15/511,252

(22) PCT Filed: Sep. 17, 2015

(86) PCT No.: PCT/CA2015/050909
§ 371 (c)(1),
(2) Date: Mar. 15, 2017

(87) PCT Pub. No.: WO2016/041081
PCT Pub. Date: Mar. 24, 2016

(65) Prior Publication Data
US 2017/0254889 A1    Sep. 7, 2017

Related U.S. Application Data

(60) Provisional application No. 62/051,476, filed on Sep. 17, 2014.

(51) Int. Cl.
*G01S 7/52* (2006.01)
*G01S 15/89* (2006.01)
(Continued)

(52) U.S. Cl.
CPC ........ *G01S 7/52036* (2013.01); *A61B 5/7257* (2013.01); *A61B 8/4483* (2013.01); *A61B 8/483* (2013.01); *G01S 15/8993* (2013.01)

(58) Field of Classification Search
CPC ............ G01S 7/52036; G01S 15/8993; G01S 7/52071; G01S 7/52028; G01S 15/8906; A61B 8/483; A61B 8/4483; A61B 5/7257
See application file for complete search history.

(56) References Cited

U.S. PATENT DOCUMENTS

2017/0254889 A1 *  9/2017  Papanicolau ....... G01S 15/8993

FOREIGN PATENT DOCUMENTS

| CA | 2998399 A1 * | 3/2016 | ......... G01S 15/8993 |
| WO | WO 2014/096789 | 6/2014 | |
| WO | WO-2016041081 A9 * | 4/2016 | ......... G01S 15/8993 |

OTHER PUBLICATIONS

Tanter M Fink M Ultrafast imaging in biomedical ultrasound IEEE Trans. Ultrasonics . . . , Jan. 2014, vol. 61, No. 1, http://ieeexplore.ieee.org/stamp/stamp.jsp?arnumber=6689779.
(Continued)

*Primary Examiner* — Daniel Pihulic
(74) *Attorney, Agent, or Firm* — Eric L. Lane; Green Patent Law

(57) ABSTRACT

A quantitative ultrasound (QUS) system for characterizing a specimen, the system comprising an ultrasound transducer operable to transmit ultrasound signals into the specimen along multiple adjacent scan lines extending axially within the specimen, and collect returned ultrasound signals therefrom and generate RF signals based on said returned ultrasound signals, wherein said RF signals are associated with respective ones of said scan lines to represent a characteristic of the specimen at each of multiple locations within the specimen along each of said scan lines; and a parallelizable processing unit communicatively coupled to said ultrasound (Continued)

transducer and operable to concurrently compute from said RF signals respective QUS values representative of said characteristic for each of a plurality of said multiple locations in parallel, wherein successive parallel outputs of said respective QUS values are characteristic of the specimen along each of said multiple scan lines.

27 Claims, 35 Drawing Sheets

(51) Int. Cl.
*A61B 5/00* (2006.01)
*A61B 8/00* (2006.01)
*A61B 8/08* (2006.01)

(56) References Cited

OTHER PUBLICATIONS

International Search Report dated Jan. 12, 2016 in related International Patent Application No. PCT/CA2015/050909.
Written Opinion dated Jan. 12, 2016 in related International Patent Application No. PCT/CA2015/050909.

* cited by examiner

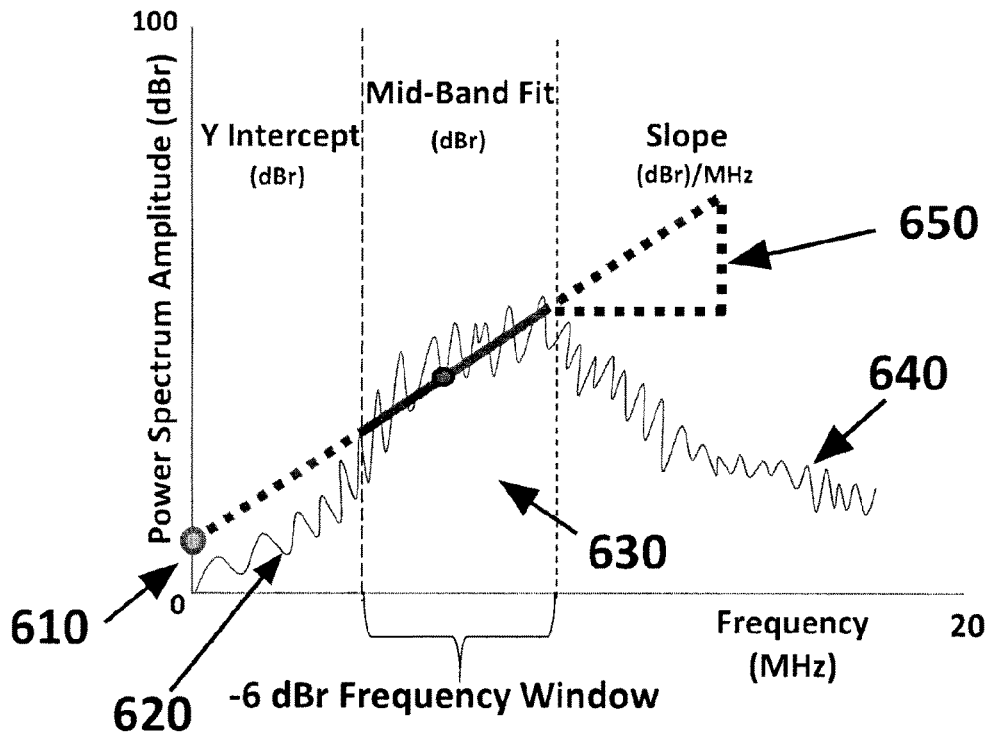

FIGURE 6

|  | Window 1 | Window 2 | Window 3 | Window 4 | ...Window n |
|---|---|---|---|---|---|
| Gate 1 | MBF Slope Intercept | MBF Slope Intercept | MBF Slope Intercept | MBF Slope Intercept | MBF Slope Intercept |
| Gate 2 | MBF Slope Intercept | MBF Slope Intercept | MBF Slope Intercept | MBF Slope Intercept | MBF Slope Intercept |
| Gate 3 | MBF Slope Intercept | MBF Slope Intercept | MBF Slope Intercept | MBF Slope Intercept | MBF Slope Intercept |
| Gate 4 | MBF Slope Intercept | MBF Slope Intercept | MBF Slope Intercept | MBF Slope Intercept | MBF Slope Intercept |
| Gate 5 | MBF Slope Intercept | MBF Slope Intercept | MBF Slope Intercept | MBF Slope Intercept | MBF Slope Intercept |
| Gate 6 | MBF Slope Intercept | MBF Slope Intercept | MBF Slope Intercept | MBF Slope Intercept | MBF Slope Intercept |
| Gate n |  |  |  |  |  |

FIGURE 7

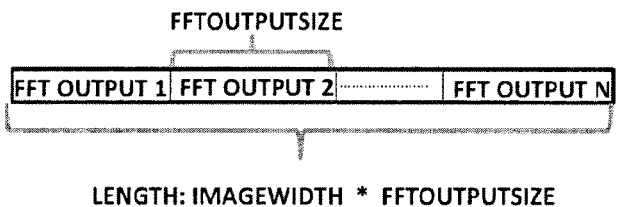
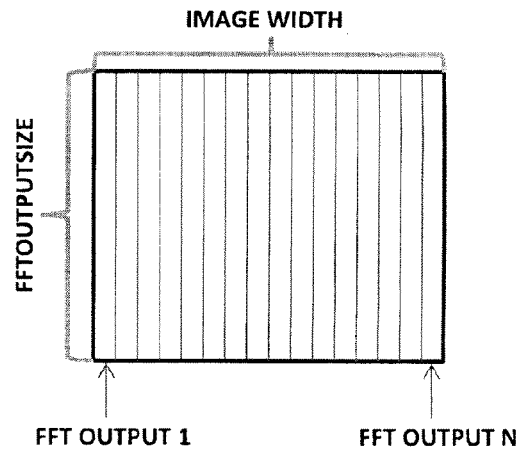
FIGURE 19
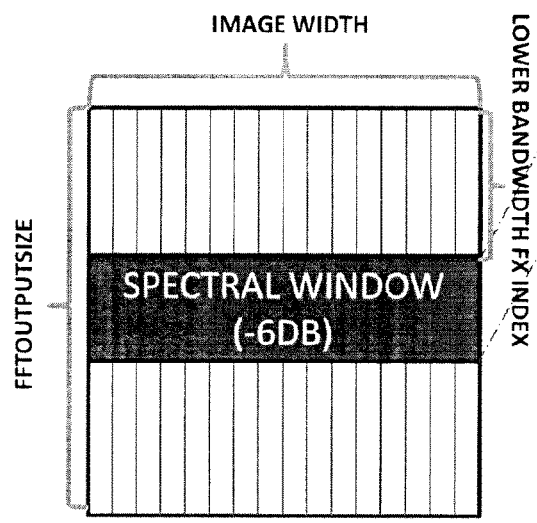
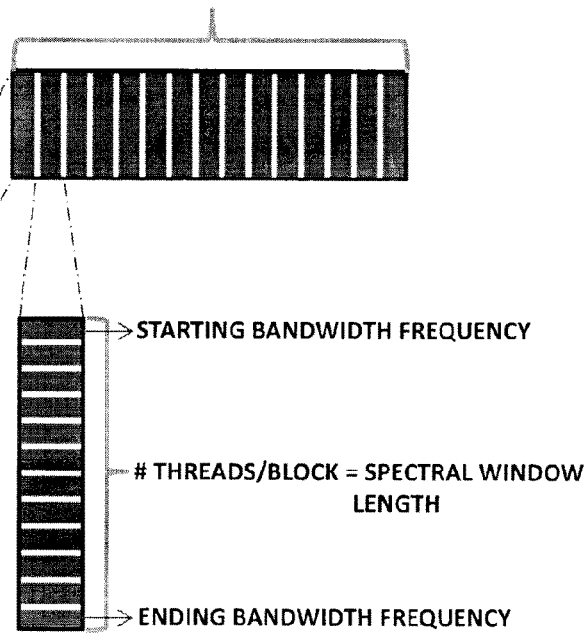
FIGURE 20

SOME EXAMPLE QUS PARAMETERS
SLOPE = (N * ΣXY − ΣXΣY) / N * (ΣX$^2$) − (ΣX)$^2$
INTERCEPT = (ΣY * ΣX) − (ΣX*ΣXY) / N * (ΣX$^2$) − (ΣX)$^2$
MBF = INTERCEPT + SLOPE * [MBFINDEX]
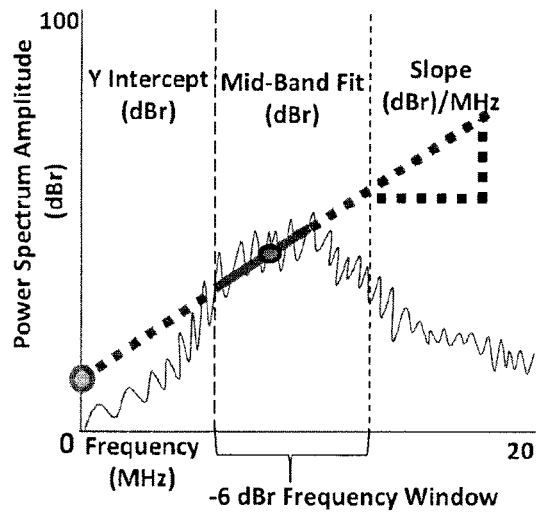
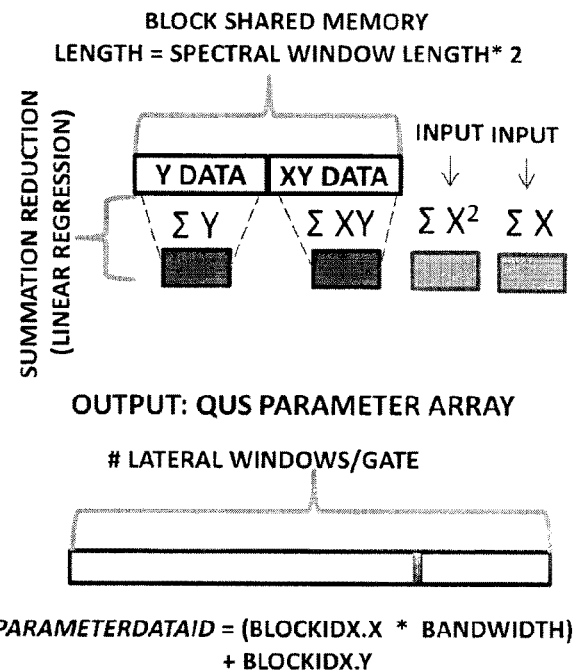
*PARAMETERDATAID = (BLOCKIDX.X * BANDWIDTH) + BLOCKIDX.Y*
FIGURE 29
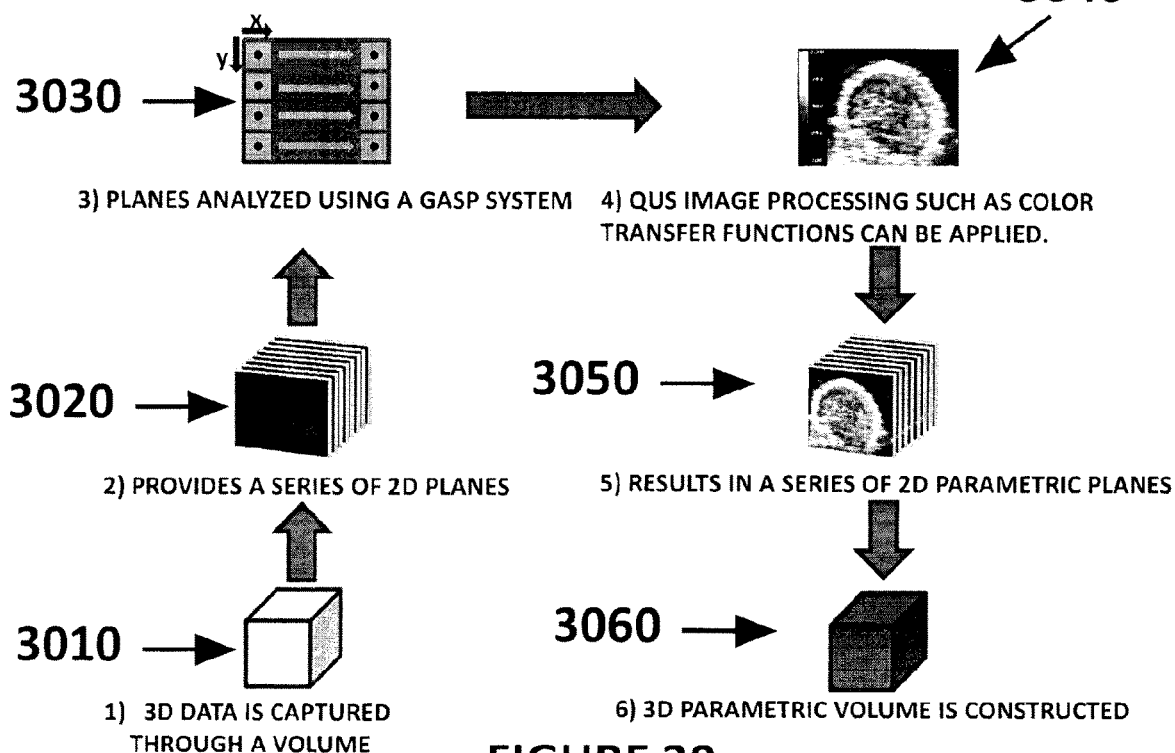
FIGURE 30

*Input*: RF Image Data (2D Abstraction)   *Input*: Hanning Window Data Array

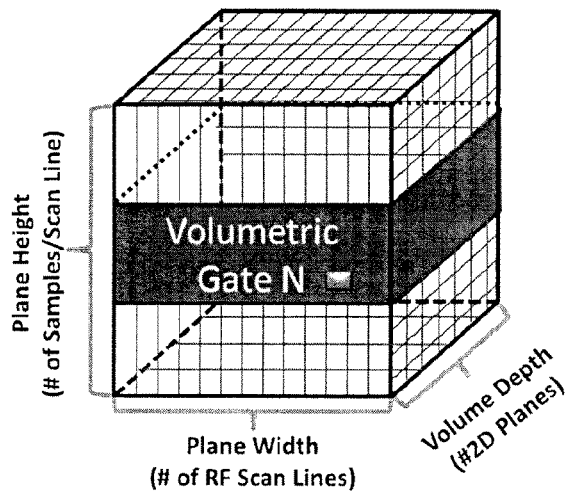

*HanningDataID* = ThreadIdx.x

*ImageDataID* = (BlockID.x * ImageHeight)
 + (GateNumber * GateOffset)
 + ThreadIdx.x

*Output*: FFT Batch Compute Array

FFT Compute Length * Plane Width * Volume Depth

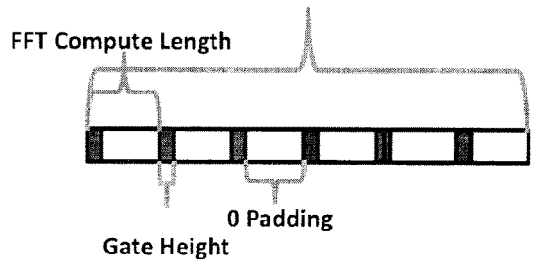

*FFTDataID* = (BlockIDx * FFTComputeLength)
 + ThreadIdx.x

CALCULATION

FFTBatch[*FFTDataID*] = RFImageData[*ImageDataID*] * HanningData[*HanningDataID*];

FIGURE 36

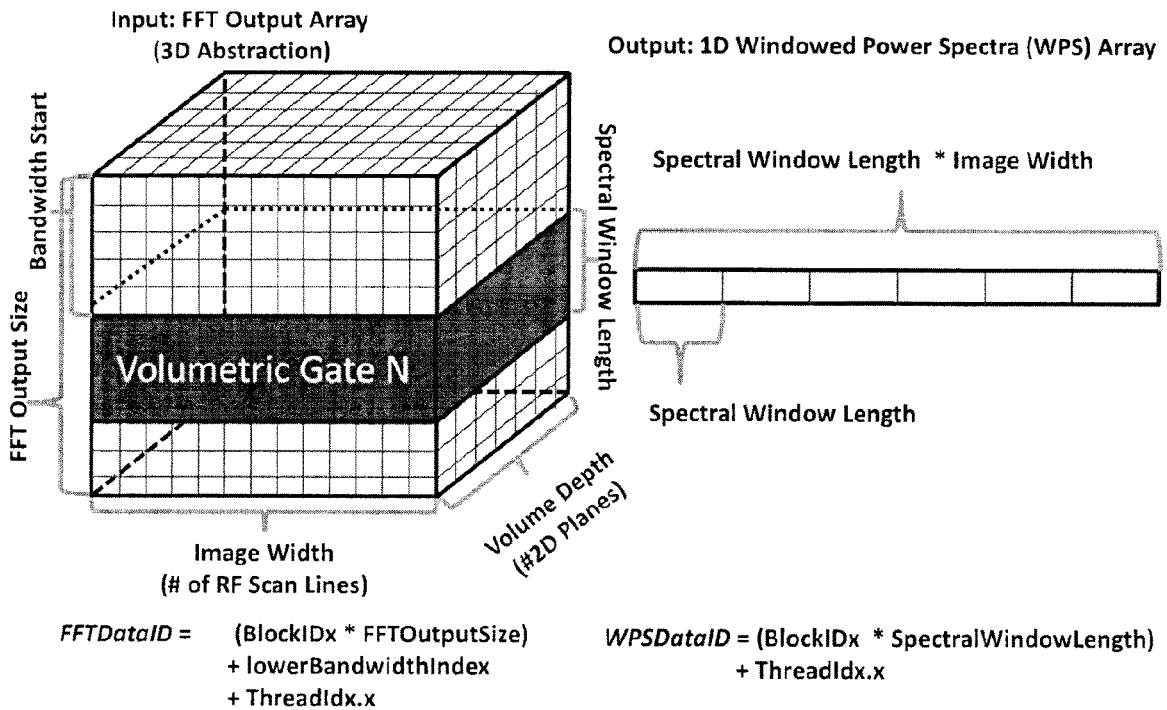
FIGURE 40
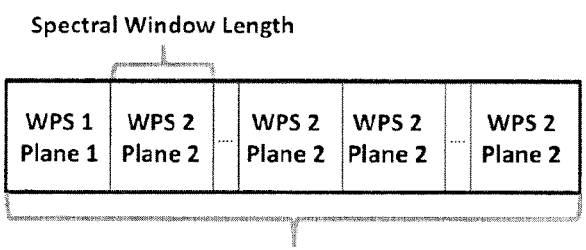
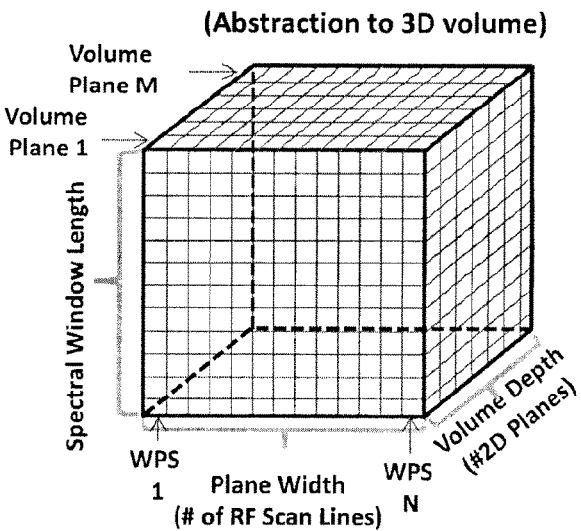
FIGURE 41

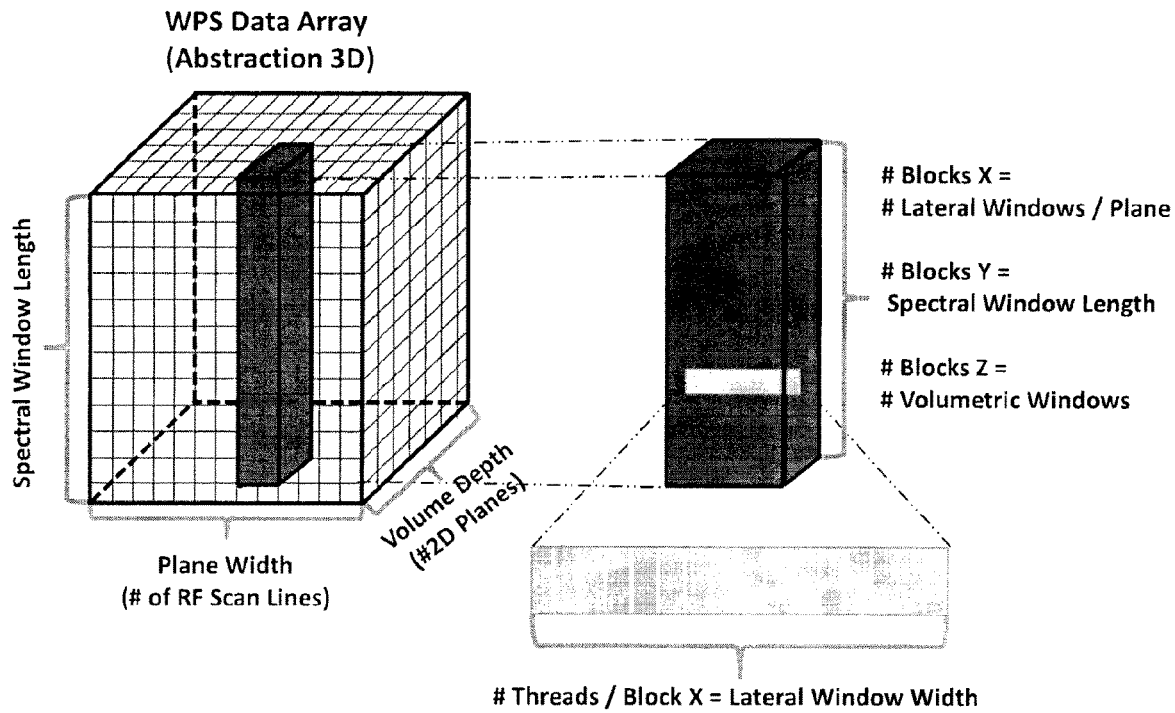
FIGURE 42
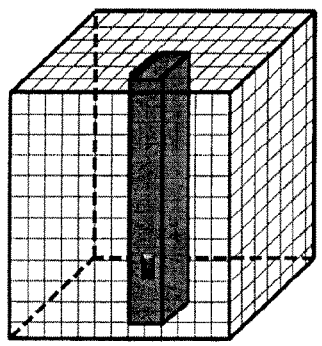
$WPS\_DataID$ = SpectralWindowLength*((blockIdx.z+numberLateralWindow]
+ (blockIdx.x * LateralWindowOffset) + threadIdx.x)
+ BlockIdx.y;
CALCULATION
SharedMemory[ *SharedMem_DataID* ] = WindowedPowerSpectralArray[*WPS_DataID*];
FIGURE 43

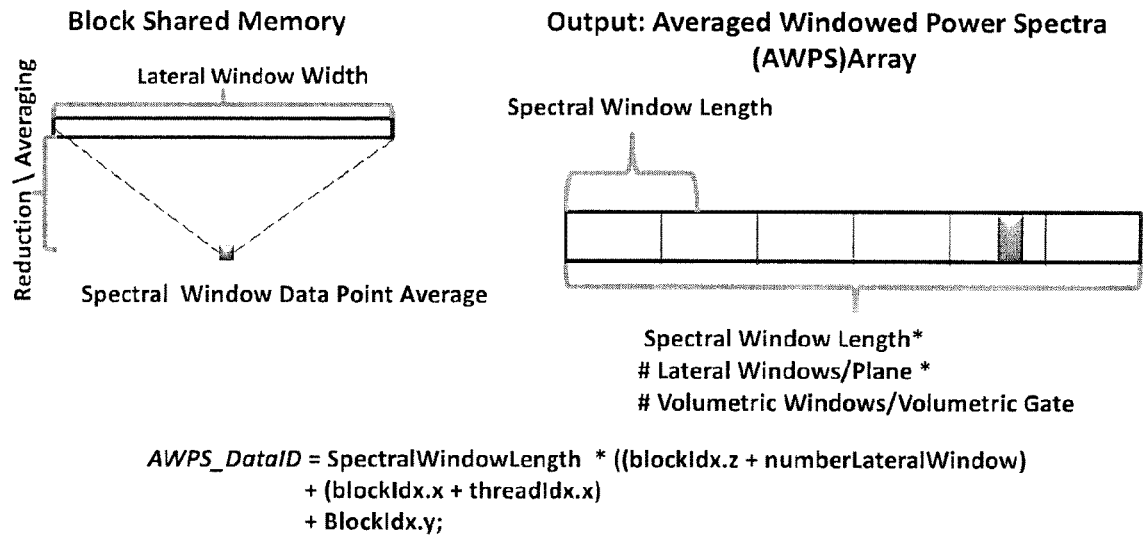
FIGURE 44
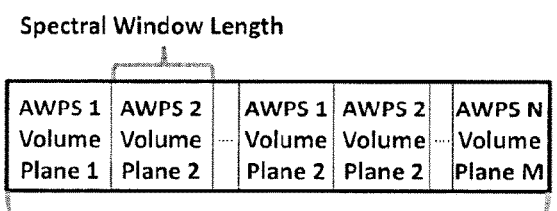
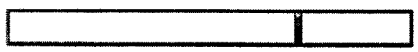
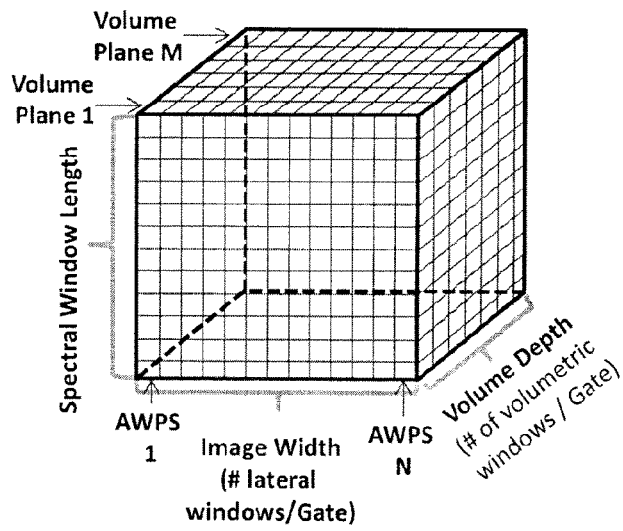
FIGURE 45

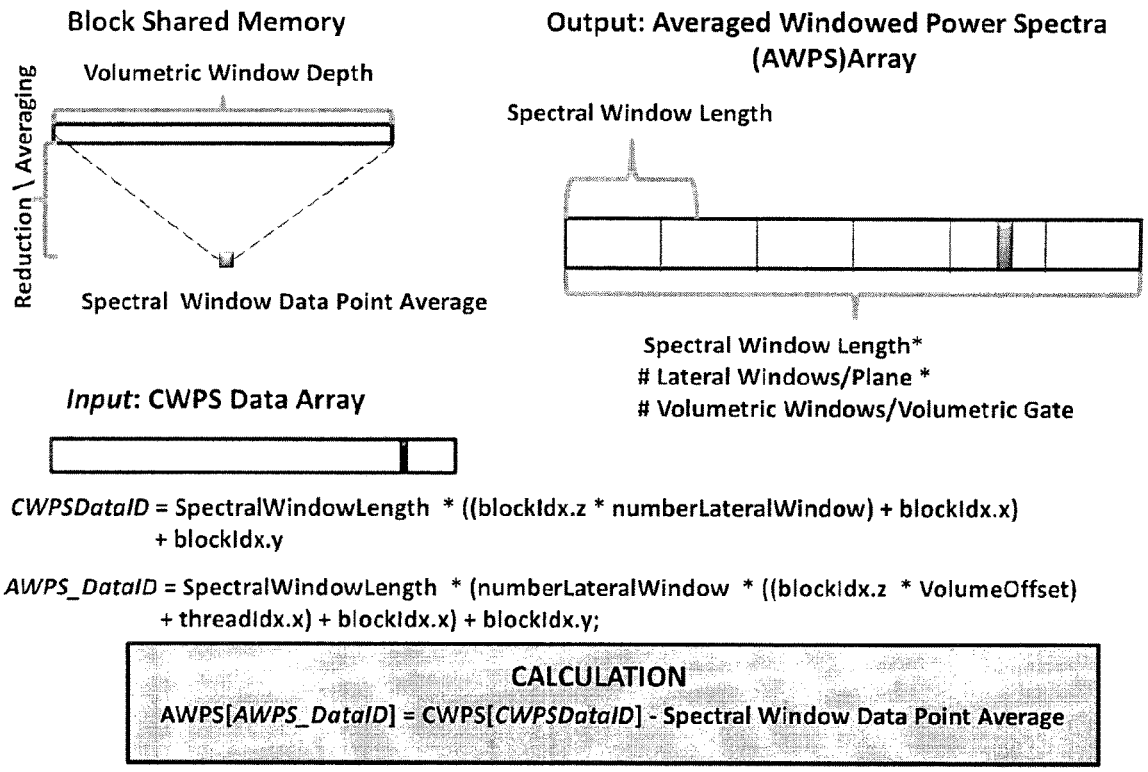
FIGURE 48
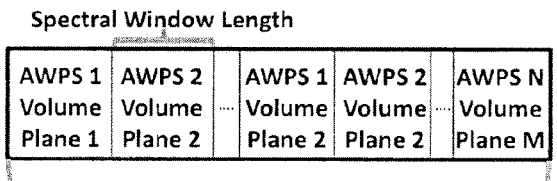
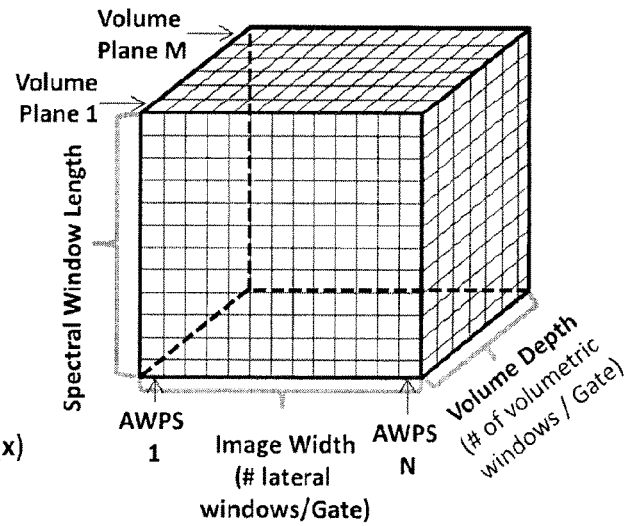
FIGURE 49

Input: AWPS Array (3D Abstraction)

Shared Block Memory Array

Spectral Window Length

| y data | xy data | y_SharedMemID = threadIdx.x;
xy_SharedMemID = threadIdx.x
                + Spectral Window Length;

AWPS_DataID = (BlockIDx.x) * Specral Window Length
           + threadIdx.x;

KERNEL CALCULATION
Copy Power Spectral Point to Shared Memory and Perform Reduction Operation for Regression

SYSTEMS, METHODS AND DEVICES FOR HIGHLY-PARALLELIZED QUS-VALUE DETERMINATION FOR CHARACTERIZING A SPECIMEN

TECHNICAL FIELD

The present disclosure relates to the use of parallelizable processing units, including GPUs, to increase QUS data processing capabilities to provide real-time, near real-time and post-processing-time specimen characterization and imaging.

BACKGROUND

There is a substantial body of research which has shown that quantitative information regarding tissue microstructure may be obtained from ultrasound backscatter data. These techniques typically employ analysis of ultrasound radiofrequency (RF) information, in one instance through spectroscopic analysis methods which have been shown to correlate to underlying features of tissue microstructure. The advent of a method of obtaining information regarding underlying tissue characteristics through ultrasound imaging has allowed for the branch of research known as ultrasound tissue characterization to materialize.

Some prior systems may refer to a limited degree to parallel processing to indicate processing which is conducted at the same time, in that it processes raw incoming ultrasound data in order to form an ultrasound data set from a multi-channel ultrasound imaging device, this in general refers to sequentially computing a set of aggregated values. This is because many ultrasound systems can have multiple channels of data being collected simultaneously which are typically processed independently in order to form the image (or beams), each of which are independently processed—or aggregated (e.g. an average intensity may be calculated for a given location) and then the aggregated values are independently and sequentially analyzed over a region of interest.

A theoretical framework behind ultrasound tissue characterization techniques was proposed by Lizzi and Feleppa [Lizzi F L, Greenebaum M, Feleppa E J, Elbaum M, Coleman D J. Theoretical framework for spectrum analysis in ultrasonic tissue characterization. Soc Am 1983; 73(4): 1366-1373, Lizzi F L; Ostromogilsky M, Fellepa E J, Rork M C, Yaremko M M. Relationship of Ultrasonic Spectral Parameters to Features of Tissue Microstructure. IEEE Trans Ultrason Ferroelectr Freq Control 1986; 33:319-329;] Lizzi F L, Astor M, Liu T, Deng C, Coleman D J, Silverman R H. Ultrasonic spectrum analysis for tissue assays and therapy evaluation. Int J Imaging Syst Technol 1997; 8:3-10.]. They determined that characteristics in the frequency information of ultrasound backscatter data could be correlated to characteristics of sub-resolution ultrasound scatterers found in tissue. Initial research demonstrated the correlation between spectral characteristics of ultrasound RF data to features of retinal and liver tissue microstructures and has since broadened to encompass a variety of Quantitative ultrasound (QUS) analysis applications. QUS applications have been demonstrated to measure tissue micro-characteristics allowing for identification of various types and states [Czarnota G J, Kolios G J, Vaziri H. Ultrasound biomicroscopy of viable, dead and apoptotic cells. Ultrasound in Med and Biol. 1997; 23:961-965; Czarnota G J, Kolios M C, Abraham J. Ultrasound imaging of apoptosis: High-resolution noninvasive monitoring of programmed cell death in vitro, in situ and in vivo. Br J Cancer 1999; 81(3):520-527; Tunis A, Czarnota G J, Kolios M C. Monitoring structural changes in cells with high frequency ultrasound signal statistics. Ultrasound in Med and Biol. 2005; 31(8):1041-1049. Kolios M C, Czarnota G J, Hussain M, Foster F S, Hunt J W, Sherar M D. Analysis of ultrasound backscatter from ensembles of cells and isolated nuclei. IEEE Ultrasonics Symposium 2001; 2:1257-1260; Vlad R, Brand S, Kolios M C, Czarnota G J, Quantitative ultrasound characterization of response to radiotherapy in cancer mouse models. Clin Cancer Res 2009; 15:2067-2075; Vlad R, Brand S, Kolios M C, Czarnota G J. Quantitative ultrasound characterization of cancer radiotherapy effect in vivo. Int J Radiat Oncol Biol Phys 2008; 72:1236-1243; Banihashemi B, Vlad R, Debeljevic B, Giles A, Kolios M C, Czarnota G J. Ultrasound Imaging of Apoptosis in Tumor Response: Novel Preclinical Monitoring of Photodynamic Therapy Effects. Cancer Res 2008; 68:8590-8596; Sadeghi-Naini A, Papanicolau N, Falou O, Zubovits J, Dent R, Verma S, Trudeau M, Boileau J F, Spayne J, Iradji S, Sofroni E, Lee J, Lemon-Wong S, Yaffe M, Kolios M C, Czarnota G J. Quantitative Ultrasound Evaluation of Tumor Cell Death Response in Locally Advanced Breast Cancer Patients Receiving Chemotherapy. Clin Cancer Res. 2013; 19(8):2163-74; Sadeghi-Naini A, Falou O, Tadayyon H, Al-Mahrouki A, Tran W, Papanicolau N, Kolios M C, Czarnota G J. Conventional Frequency Ultrasonic Biomarkers of Cancer Treatment Response In Vivo. Transl Oncol. June 2013; 6(3): 234-243; Sadeghi-Naini A, Papanicolau N, Falou O, Tadayyon H, Lee H, Zubovits J, Sadeghian A, Karshafian R, Al-Mahrouki A, Giles A, Kolios M C, Czarnota G J. Low-frequency quantitative ultrasound imaging of cell death in vivo. Med. Phys. 40 (8), August 201; Sadeghi-Naini A, Falou O, Czarnota G J. Quantitative ultrasound visualization of cell death: Emerging clinical applications for detection of cancer treatment response. Conf Proc IEEE Eng Med Biol Soc. 2012; 2012:1125-8; Lakshmanan S, Tadayyon H, Sadeghi-Naini A, Falou O, Jahedmotlagh Z, Oelze M L, Czarnota G J. Evaluation of tumor cell death response in locally-advanced breast cancer patients to chemotherapy treatment by scattering property estimates using ultrasound backscatter. POMA 19, 075087 (2013); Taggart L R, Baddour R E, Giles A, Czarnota G J, Kolios M C. Ultrasonic characterization of whole cells and isolated nuclei. Ultrasound Med Biol. 2007; 33:389-401]. By providing the capacity to distinguish underlying cell morphologies, ultrasound tissue characterization techniques have been applied to a diverse set of fields such as distinguishing between areas of malignancy in the human prostate [E J Feleppa, A Kalisz, S Melgar, Typing of prostate tissue by ultrasonic spectrum analysis. IEEE Trans. Ultrason Ferroelec Freq Contr 1996: 43: pp 609-619; Ervis Sofroni, "Tissue Characterization of Prostate Cancer Using Quantitative Analysis of Low Frequency Ultrasound," MSc, Computer Science, Ryerson Univeristy, Toronto, 2011] and differentiation of liver as well as cardiac abnormalities [R H Silverman, R Folberg, M J Rondeau, Spectral parameter imaging for detection of prognostically significant histologic features in uveal melanoma. Ultrasound in Med. and Biol. 2003: 29: pp 951-959; F L Lizzi, D L King, M C Rorke, Comparison of theoretical scattering results and ultrasonic data from clinical liver examinations. Ultrasound in Med. and Biol. 1988: 14: pp 377-385]. Further examples of QUS analysis techniques have been demonstrated to differentiate between benign fibroadenomas from mammary carcinomas and sarcomas, in the detection of apoptotic cell death leading to technologies for cancer treatment monitoring in a variety of experimental and clinical models, as well as many others.

Traditional approaches using standard central processing units (CPU) in general purpose computers are not well suited to solving these computational-intensive calculations efficiently across many locations points within a specimen. CPU architectures are designed for general purpose computing and not optimized for highly parallelizable data processing.

Currently, QUS parameters are being calculated using traditional computing methods which use the computers Central Processing Unit (CPU) to process ultrasound RF data. This approach to computing QUS parameters results in tens of seconds to minutes of processing time in order to obtain QUS parameters for a typical frame of ultrasound radiofrequency data on modern computing platforms. Although CPU technology has rapidly increased in processing capabilities, the resulting increase in QUS parameter calculations has not afforded the capability processing speeds approaching those required for real time data processing, particularly in view of the computational requirements for calculating QUS parameters of the higher resolution (or granularity) needed for some tissue characterization, coupled with demands for real-time or on-demand analysis or imaging.

The limitations of traditional CPU computing techniques to compute QUS parameters from ultrasound radiofrequency data has limited the use of the technology to a post processing paradigm. One drawback to standard CPU processing approaches is that they approach the analysis in a serial manner and do not have the processing capabilities necessary for real time requirements.

There is a need for a system which accelerates the processing throughput of QUS parameters, preferably for ultrasound tissue characterization.

This background information is provided to reveal information believed by the applicant to be of possible relevance. No admission is necessarily intended, nor should be construed, that any of the preceding information constitutes prior art.

SUMMARY

The following presents a simplified summary of the general concept(s) described herein to provide a basic understanding of some aspects of the subject matter described herein. This summary is not an extensive overview of the subject matter. It is not intended to restrict key or critical elements of the subject matter or to delineate the scope of the subject disclosed herein beyond that which is explicitly or implicitly described by the following description and claims.

Traditional approaches to QUS parameter calculations for the purpose of ultrasound tissue characterization approach the problem in a mainly serial manner using windowing processes. There is a need for coupling very high numbers of discrete computational analyses across a region of an ultrasound subject, which is needed for QUS tissue characterization, with a highly parallelizable software and hardware architecture to permit real-time, or near real-time data processing.

There are provided herein systems, methods and devices for highly parallelized QUS-value determination for characterizing a specimen via ultrasound.

In one aspect there are provided quantitative ultrasound (QUS) systems for characterizing a specimen, the system comprising an ultrasound transducer operable to transmit ultrasound signals into the specimen along multiple adjacent scan lines extending axially within the specimen, and collect returned ultrasound signals therefrom and generate RF signals based on said returned ultrasound signals, wherein said RF signals are associated with respective ones of said scan lines to represent a characteristic of the specimen at each of multiple locations within the specimen along each of said scan lines; and a parallelizable processing unit communicatively coupled to said ultrasound transducer and operable to concurrently compute from said RF signals respective QUS values representative of said characteristic for each of a plurality of said multiple locations in parallel, wherein successive parallel outputs of said respective QUS values are characteristic of the specimen along each of said multiple scan lines.

In another aspect, there are provided methods of real-time quantitative ultrasound (QUS) calculation across a region of a specimen, the specimen being subjected to ultrasound signals along one or more scan lines, the method comprising associating RF signals generated from returned ultrasound signals from the specimen with respective locations along the one or more scan lines; providing to a parallelizable processing unit, in response to an initiating data request, a plurality of raw signal data, each of said raw signal data uniquely associated with the respective locations calculating, in parallel in said parallelizable processing unit, at least one QUS parameter value, preferably a plurality of QUS parameter values, each of said QUS parameter values associated with at least one of said raw signal data from a group of one or more adjacent respective locations along one or more of the one or more scan lines; and generating, in a communicatively coupled data storage medium, a data array of QUS parameter values, each of said QUS parameter values in said data array being indicative of a characteristic of the specimen at the at least one location associated with the returned ultrasound signals, and associated RF signals, used to calculate that QUS parameter value.

In another aspect, there is provided a parallelizable processing device for simultaneously calculating at least one quantitative ultrasound (QUS) value, preferably a plurality of QUS values representative of a region of a specimen, said parallelizable processing device configured to receive a plurality of RF signals collected from an ultrasound analysis of said region, each RF signal associated with respective axial scan lines in said specimen representative of a characteristic of the specimen at each of multiple locations within the specimen along each of said axial scan lines, said parallelizable processing device comprising a data bus configured to accept a plurality of data values associated with said RF signals, each respective data value relating to a given RF signal based on an ultrasound signal from a given location in said specimen; a data storage medium configured to store said plurality of data values and, upon a data request, provide at least some of said plurality of data values; and a parallel processing unit, said parallel processing unit comprising a plurality of processors, said processors for concurrently performing the same analysis function in parallel on each of said provided data values.

According to one aspect, there is provided use of at least one graphical processing unit (GPU), in a single instruction multiple data graphical processing unit (SIMD GPU) architecture for processing of at least one quantitative ultrasound (QUS) data parameter, preferably a plurality of QUS data parameters.

According to another aspect, there is provided use of at least one GPU to increase raw ultrasound backscatter processing speeds.

According to yet another aspect, there is provided a system for increasing processing throughput of at least one QUS parameter, preferably a plurality of QUS parameters, said system comprising: at least one QUS datum; preferably selected from RF datum, more preferably selected from raw ultrasound datum; at least one SIMD GPU architecture; for receiving and processing said at least one QUS datum; and at least one computer for housing said architecture and passing said at least one QUS datum from an input source of said at least one QUS datum to the at least one SIMD GPU.

According to yet another aspect, there is provided a method of processing at least one QUS datum, preferably a plurality of QUS data, using at least one GPU, said method comprising: gating at least one axial scan line, preferably a plurality of axial scan lines; optionally gate windowing; calculating at least one axial gate spectrum, preferably axial gate spectra, preferably a power spectrum; organizing said at least one axial gate spectrum into at least one lateral window, preferably organizing axial gate spectra into lateral windows; averaging said at least one lateral window, preferably averaging said lateral windows; optionally normalizing said at least one averaged lateral window, optionally normalizing said lateral windows, preferably to a calibration pulse; extracting bandwidth from said at least one averaged lateral window, preferably extracting bandwidth from said averaged lateral windows, preferably said bandwidth is −6 dB; computing at least one QUS parameter, preferably at least one spectral property, preferably spectral properties, such as but not limited to integrated backscatter, mid-band fit, slope, 0-MHz intercept and combinations thereof.

According to yet another aspect, there is provided a method of accelerating processing of at least one QUS data parameter, preferably a plurality of QUS data parameters, said method comprising the use of at least one GPU, most preferably at least one SIMD GPU, in processing said at least one QUS data parameter.

According to yet another aspect, there is provided Real-Time (or near real time) Tissue Characterization using at least one GPU.

According to yet another aspect, there is provided Real-Time (or near real time) QUS calculation using at least one GPU.

According to yet another aspect, there is provided individual GPU processing steps for computing RF data for QUS, said processing steps comprising: Gating; Windowing; Performing at least one Fast Fourier Transform (FFT) calculation from RF data within windows; and Various Spectral Analysis processes for computing QUS parameters.

According to yet another aspect, there is provided individual GPU processing steps for computing RF data for QUS, said processing steps comprising at least one of the following steps: Gating; Windowing; At least one spectral calculation, including frequency-domain calculations such as, but not limited to, FFT; and Various Spectral Analysis Processes for computing parameters.

According to yet another aspect there is provided a QUS process, preferably real-time, to be implemented by a computing device, comprising: receiving as input multiple ultrasonic axial scan lines; gating said multiple ultrasonic axial scan lines into distinct gates; for each of said scan lines within a given one of said gates, concurrently calculating one or more spectral parameters in parallel; and combining (mapping) said one or more spectral parameters in one or more output arrays. Preferably said QUS process further comprises windowing said multiple ultrasonic axial scan lines into distinct windows; and concurrently calculating said one or more spectral parameters in parallel for each of said distinct windows. Even more preferably, said process further comprises, prior to said calculating, batch processing, preferably via parallel batch FFT processing, each of said scan lines within said given one of said gates to output respective spectra from which said one or more spectral parameters may be respectively calculated in parallel.

According to yet another embodiment, there is provided a computer-readable medium having statements and instructions for implementation by a processing device having parallel processing capabilities to process ultrasonic data for QUS application by: receiving as input multiple ultrasonic axial scan lines; gating said multiple ultrasonic axial scan lines into distinct gates; for each of said scan lines within a given one of said gates, concurrently calculating one or more spectral parameters in parallel; and combining (mapping) said one or more spectral parameters in one or more output arrays. Preferably, the computer-readable medium further comprises statements and instructions for implementing parallel calculation of said one or more spectral parameters on a GPU.

In one embodiment, said processing is in real-time. In another embodiment, there is provided the use of GASP for accelerated volumetric QUS analysis and imaging.

As GASP achieves order of magnitude larger processing throughputs when compared to the current processing systems, GASP may provide enhancements in the processing of multi-frame ultrasound data, allowing for sufficient acceleration for 3D visualization and analytical applications.

In another embodiment, there is provided QUS Post-Processing Analysis Techniques using GASP. As GASP may be used to accelerate the processing of ultrasound data and provide the input parameters for further analysis, it may accelerate the overall process.

Other aims, objects, advantages and features of the subject matter disclosed herein will become more apparent upon reading of the following non-restrictive description of specific embodiments thereof, given by way of example only with reference to the accompanying drawings.

BRIEF DESCRIPTION OF THE FIGURES

In order that the disclosed subject matter may be better understood, exemplary embodiments will now be described by way of example only, with references to the accompanying drawings, wherein:

FIG. 6 is a depiction of QUS parameters through linear regression.

FIG. 7 is a depiction of a processed QUS parameters data array.

FIG. 19 is another depiction of a data analysis step in accordance with one embodiment of the instant application.

FIG. 20 is another depiction of a data analysis step in accordance with one embodiment of the instant application.

FIG. 29 is another depiction of data analysis steps in accordance with one embodiment of the instant application.

FIG. 30 is a depiction of a 3-dimensional ultrasound analysis based on 2-dimensional conjoining.

FIG. 36 is another depiction of a data analysis step in accordance with one embodiment of the instant application.

FIG. 40 is another depiction of a data analysis step in accordance with one embodiment of the instant application.

FIG. 41 is another depiction of a data analysis step in accordance with one embodiment of the instant application.

FIG. 42 is another depiction of a data analysis step in accordance with one embodiment of the instant application.

FIG. 43 is another depiction of a data analysis step in accordance with one embodiment of the instant application.

FIG. 44 is another depiction of a data analysis step in accordance with one embodiment of the instant application.

FIG. 45 is another depiction of a data analysis step in accordance with one embodiment of the instant application.

FIG. 48 is another depiction of a data analysis step in accordance with one embodiment of the instant application.

FIG. 49 is another depiction of a data analysis step in accordance with one embodiment of the instant application.

DETAILED DESCRIPTION

Figure 1:
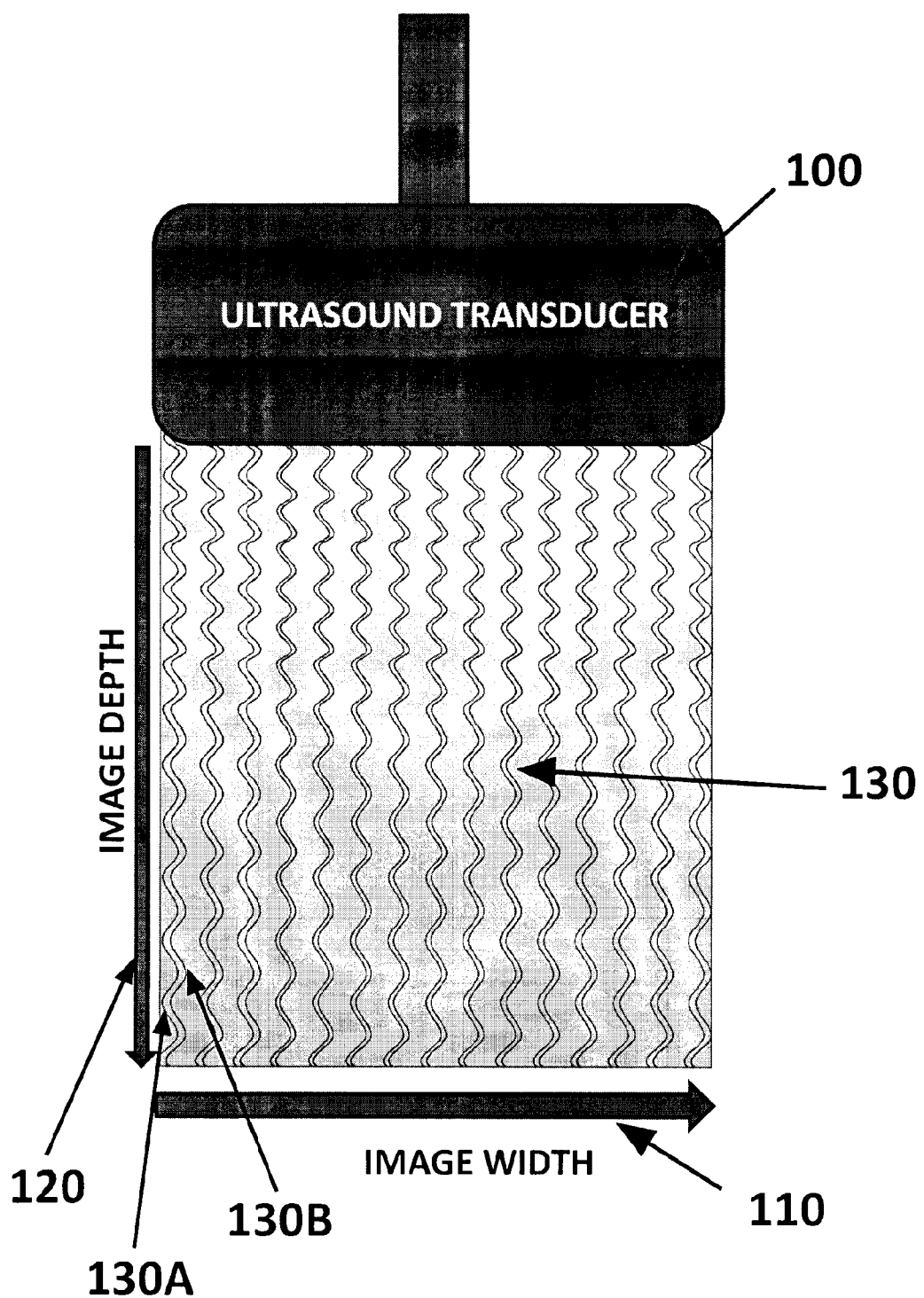
FIG. 1 is an ultrasound transducer.

With reference to the disclosure herein and the appended figures, systems, methods and devices for characterization, including real-time characterization in some embodiments, of quantitative ultrasound parameters of a region of a specimen in accordance with various embodiments.

Aspects of the subject matter disclosed herein, provide for systems, methods and devices relating to the collection and efficient processing of quantitative ultrasound data, which may be used, inter alia, to perform tissue characterization beyond ultrasound imaging and include a wide variety of RF signal analysis from signals returned from a specimen during ultrasound analysis. Such RF signal analysis often requires computationally intensive analyses across regions of a specimen that, relative to the sampling resolution used in many ultrasound analyses, is large. Embodiments herein provide parallel analysis for the following non-limiting examples: (a) aggregating raw signal data into useful data that is associable with, for example, axial gates and lateral windows that relate to corresponding locations of the region being analyzed in the specimen; (b) compiling underlying ultrasound data into other QUS data, or other data required for additional QUS data calculation, such as, for example, at each axial gate and lateral window or groups thereof, RF signal parameters, such as but not limited to backscatter intensity, as well as time- and frequency-domains of RF signals; (c) signal parameter correction or smoothing that avoids over-emphasizing statistical outliers, as well as comparison or standardization using reference signals, at each of a plurality of axial gate and lateral window locations; (d) determining additional QUS parameters from additional mathematical processes, such as regression-based analysis, from any of the foregoing at each of a plurality of axial gate and lateral window locations; (e) outputting all of the foregoing into a data array; (f) generating tissue characterization analyses or image-based representations thereof from said data array, wherein one or more data array elements correspond to a specific location within the specimen and/or the resulting image. While standard techniques, which often involve sequential collection and analyses of raw data (e.g. to get time-domain spectral data) as well as higher order parameters corresponding to discrete sampling locations (e.g. regression analysis on frequency-domain spectral data), the time for calculating QUS parameters across a region of a specimen is too great for real-time or on-demand analysis. In some cases, existing QUS analysis requires a sequential set of calculations for each gate/window location to provide the desired QUS parameter (since the input of one function is the output of a preceding step), which is then sequentially determined for each gate/window location across the region of interest in the specimen. Embodiments herein provide a system, device and method for parallelizing at least each step for all gate/window locations and providing concurrent determination for a subsequent step of the overall analysis, and in some embodiments, multiple steps may be performed in parallel for all gate/window locations (e.g. gate signal array inputting, Hann windowing thereof, and reference signal correction). In some embodiments, the architectures of the parallelizable processing unit operate in conjunction with the output of the ultrasound transducer to determine in a highly parallelized manner a plurality of complex analyses at a plurality of scanned locations in a specimen to provide on-demand tissue characterization data and/or imaging based on tissue characterization data. In some cases, the analysis is in respect of a 2-dimensional region of interest in a given specimen (i.e. a planar image of a cross-section of a specimen). In some cases, the analysis is in respect of a 3-dimensional region of interest in a given specimen (e.g. a volumetric representation of a specimen, or portion thereof). As used herein, the term "parallelization" refers to the general approach of analytical processing required to obtain quantitative measurements of a data set in a manner which involves solving independent regions of analysis simultaneously. This may be, in some embodiments, a computational parallelization approach as opposed to a data collection and processing perspective.

With reference to FIG. 1, there is shown an ultrasound transducer 100. Typical signal processing requirements employed in QUS analysis of ultrasound radiofrequency data obtainable from said ultrasound transducer are as follows: Ultrasound data is acquired within a field of view, essentially equivalent to the image width 110 to the image depth 120 using an ultrasound transducer 100 as shown in FIG. 1. This is a simple example of ultrasound data. It is understood that ultrasound data may comprise signal pulses 130 of varying types of beams and shapes in varying degrees of complexity generated by the receiving function of the transducer upon reception and detection of ultrasound energy emitted from, and sent back to the ultrasound transducer 100. The scanned region is defined by multiple scan lines 130 of data constituting the width (lateral direction) 110 of the image. The depth (axial direction) 120 of the image is comprised of a given number of sampled data points from each scan line. The ultrasound transducer 100 is configured to transmit ultrasound, which when returned back to the transducer 100 is converted to an RF signal. Each scan line 130 comprises of ultrasound emitted 130A by the ultrasound transducer 100, as well as ultrasound that is returned 130B to the transducer 100 as a result of the emitted ultrasound signal 130A, for example due to either or a combination of reflection, absorption, signal loss, constructive or destructive interference, or signal generation. Upon detection and measurement of said returned ultrasound signal 130B, an RF signal is created by the ultrasound transducer 100 that is representative of the returned ultrasound signal 130B.

In some embodiments, the RF signal data, representative and associated with locations across the region of interest in the specimen (i.e. some or all of the scanned region), is then analyzed in parallel. Various examples of possible data processing of the collected data are shown in FIGS. 2 to 7 and 15 to 29. In some aspects any or all of such data processing steps may be done in a parallelizable processing unit that is data communication with the ultrasound transducer (or alternatively can receive raw RF signal data collected previously from an ultrasound transducer). A parallelizable processing unit may refer to any data processing unit that is configured to perform a very high number of discrete data processing functions in parallel, each by a discrete data processing sub-unit (e.g. a processor or core thereof). In some embodiments, the parallelizable processing unit ("PPU") may be characterized in that it is configured to access or retrieve a large number of discrete data points concurrently, possibly as a result of the same triggering event (i.e. a read request or a fetch request) and then processing each of them across discrete data processors that individually make up the PPU. In some embodiments, the PPU may be configured to facilitate the operation of a single instruction (or instruction group) for each of large number of discrete data points; in some embodiments, it may support SIMD (Single Instruction Multiple Data) architecture. In some embodiments, the PPU utilizes an architecture wherein each of the multiple processors do not require distribution of instructions prior to processing (which in conventional CPU processors may cause latency issues); such instructions may be pre-loaded or distributed once to each processor in parallel.

In some embodiments, exemplary PPUs may include Connection Machine (see Sung, "SIMD Parallel Processing", 6.911: Architectures Anonymous Feb. 22, 2000) which is composed of 65,536 bit processors, wherein each die thereof consisted of 16 processors with each processor capable of communicating with each other via a switch. These 4,096 dies formed the nodes of a 12th dimension hypercube network. Thus, a processor was guaranteed to be within 12 hops of any other processor in the machine. The hypercube network also facilitated communication by providing alternative routes from source processor to destination. Each node was given a 12-bit node ID, and different paths between two nodes in the network could be traversed based on how the node ID was read. The network allowed for both packet and circuit-based communication for flexibility. Another PPU may include the Abacus machine created at the MIT AI Lab (see also Sung, above) and comprising of 1024 bit processing elements set in a 2D mesh. The primary concept of interest from the design was that the processing elements were configurable, and used reconfigurable bit parallel "RBP" algorithms instead of traditional bit serial computation. This means that each PE emulated logic for part of an arithmetic circuit (be it an adder, shifter, multiplier, etc.) based on a RBP algorithm, which permitted configurable discrete processors with some tradeoff to parallelization (i.e. even though most processes occurred more or less concurrently, there may be some introduced latency as some processes may not begin and/or end simultaneously). Another PPU may include the CAM-8 cellular automata machine (see also Sung, above) wherein each processing element is connected in a 3D mesh, a natural topology for describing microphysical simulations, wherein each processing element consisted of a programmable lookup-table with an associated local memory. Since there are usually not enough processing elements to assign one to each cell of the system that was to be simulated, each PE was assigned a specific region and performed updates to each cell virtually. Cellular automata applications include microscopic physics/lattice gas simulations (for which the machine was originally intended), statistical mechanics, and data visualization/image processing.

In yet other embodiments, a PPU may be described as a data processing unit whose architecture is specifically designed for high throughput through discrete individual processors, wherein specific latency on any given individual processor therefore of reduced significance compared to, e.g., a conventional CPU processor in a general purpose computer. In some embodiments, a PPU may comprise a processing unit wherein there is, relative to conventional CPUs, a significantly high number of transistors dedicated to carrying out specific processing instructions (e.g. arithmetic logic units, or ALUs) with a reduced number of transistors dedicated to control, caching or registering. An example of such a PPU would include a GPU, and variants thereof; this may further include for example, NVIDIA's Tesla C2050/C2070 GPU.

In some aspects of the disclosed subject matter, QUS value calculation may be summarized according to the following processes. Initially, radiofrequency (RF) data is input into the system. Data resulting from this input is generated as a result of beams of ultrasound signals introduced into a specimen and the responses thereof being sampled by the ultrasound transducer or imaging device. In some aspects, some or all collected data may be associated with its respective sample location in parallel.

The sampled data is collected from each of a plurality of locations along an axial scan line into the specimen. The collected data are associated with axial scan lines and are "gated" along said scan lines (sometimes referred to as axial scan line "gating"). Depth dependent regions of analysis are called gates; RF data is sampled from each such region and associated with said gate. The process of gating ultrasound backscatter data involves identifying the particular sampled data that corresponds to particular gates, and extracting the data from the overall data set. In some embodiments, individual data points may correspond to multiple gates as gates may form overlapping regions. In some aspects, some or all gates may be associated with its corresponding RF data in parallel by the PPU.

The gated data is then associated with lateral windows across the width of the scanned region. The term windowing can have varying meanings depending on the context. In this instance, windowing refers to the use of a time domain windowing function which is applied to the data prior to calculating the spectra. This is applied to each scan line of each gate prior to spectral calculations, or in some cases data from multiple scan lines wherein a given window may comprise or be based on data from the same one or more corresponding windows from adjacent scan lines. In some embodiments, a mathematical function is applied to select discrete portions of the sample RF signals and/or to increase the robustness of the data to outliers, including by reducing the bias of outlier sample data resulting from, e.g., measurement error or variability or other non-specimen related data. In some embodiments, various distribution calculations may be used; in some embodiments, Hann windowing may be used. In some aspects, some or all windowing and/or distribution calculation for each of said windows may be performed in parallel.

Some aspects include the process of computing the power spectrum of a given set of ultrasound backscatter data belonging to a gate. Calculation requires the computation of a Fast Fourier Transform (FFT) to transform the data into the frequency domain, followed by a calculation to compute the logarithmically compressed power spectrum. In some embodiments, this is performed for each scan line on each gate through the data set. In some aspects, some or all power spectra calculation for each of the windows may be performed in parallel.

In some aspects, spectral data windowing, or lateral scan line windowing, for each gate is organized into one or more windows across the scanned region dependent upon application requirements. The term scan line windowing refers to identifying which calculated power spectra correspond to windows and organizing the spectra for further processing. In most cases, individual spectra correspond to multiple windows, as windows form overlapping regions, as can be seen, for example in FIG. 4. In some aspects, some or all power spectra calculation for each of the windows may be performed in parallel.

In some aspects, there may be provided lateral scan line averaging. This may refer to an averaging operation on the data for each individual window in the data set; which may be performed in parallel. The result is a single averaged power spectrum representing the data for each window. In some embodiments, this step may comprise various mathematical operations to provide an aggregated value for a group of individual windows, and may employ various weighting, or other distribution functions, and is not limited to determining, for example, mean or median values of RF signal parameters.

In some aspects, there may be provided window power spectrum normalization, which refers to a data calibration process, and may not be required in all embodiments. Calculated power spectral data from a reference source such as a planar reflector or imaging phantom is used to normalize the current image. This may be performed by the division of the current image data from the reference data, but other mathematical functions for normalizing the power spectrum against a reference spectrum may be used. While this may be carried out in parallel across all windows and/or gates in the scanned region, the step may be performed parallel with other steps to the extent that this step does not require the output of any prior step.

In some aspects, there may be provided power spectrum windowing, which refers to the process of identifying and extracting the region of the calculated power spectrum which will be used in linear regression calculations (or potentially any other statistical analysis for determining relationships between variables). The steps of identifying the regions of the spectra that will be used are described in Step 3 below and in FIGS. 18 through 21 (pre-processing calculations). In many cases, identifying the spectral window is only required once, and this step reduces to an extraction of the required data and setup for the next step. This step is performed upon all normalized averaged window data through the data set. As with other steps, it may be performed in a parallelized manner for multiple discrete data sets.

In some aspects, each discrete data set may have performed on it various linear regression calculations on each power spectra window (or other data, such as the time-domain window). Other statistical analyses may be performed on each discrete data set, including, without limitation, the raw data or the time-domain data. Other types of regression, including non-linear, may also be used as indeed any other type of statistical analysis for determining parameters associated with how the data points of interest are related. This step may, for example, calculate a line of best fit through the normalized averaged spectral window data using a least squares approach, or indeed other regression types. The characteristics of the linear regression line may be the final QUS parameters of interest. Other mathematical functions may be applied to the normalized averaged spectral window, including non-linear regression. As with other steps, the regression step for a plurality of discrete data sets may be carried out in parallel.

In some aspects, there is provided a step of parameter extraction. The process of identifying characteristics of interest from the linear regression calculations, and organizing the data into a final output array, wherein the population of each array element may be carried out in parallel. Moreover, in some aspects, this array may be used for analytical or image formation purposes; again, each element of the image (i.e. pixel) or of the analytical array may be determined or generated in parallel.

In each of the above steps, it is to be understood that parallel processing may include substantially parallel processing wherein the carrying out of process instructions on discrete data sets may not occur simultaneously, but rather at least some of a significant portion of the concurrent process instructions at least partly overlap in time. Moreover, a plurality of data points may be "fetched" or requested at the same time or as a result of the same data request or triggering event. In some cases, control information relating to the process instructions for each processor in a parallelizable processing unit may be requested in parallel, or substantially concurrently.

In one embodiment, there is provided a system for processing QUS spectral data for analyzing a region of a specimen. In some embodiments, the analysis is utilized for tissue characterization, including but not limited to differentiating between different tissues or tissues that exhibit particular physiological and/or histological characteristics. In other embodiments, the specimen may comprise non-biological systems, including for example in fault detection or detection of non-uniform or non-homogenous materials.

In some embodiments, the system comprises an ultrasound transducer operable to transmit ultrasound signals into the specimen along multiple adjacent scan lines extending axially within the specimen, and collect returned ultrasound signals, such as ultrasound backscatter therefrom, on the basis of which the ultrasound transducer generates RF signals that are representative of the returned ultrasound signals. In some embodiments, the transmission and detection of ultrasound and/or RF signals need not be from the same device. Scan lines may be linearly arranged in some devices (i.e. along a single line or axis), but in others the adjacent scan lines may be arranged non-linearly or lengthwise and widthwise. In addition, the transmitted ultrasound signals may be emitted in scan lines, or as broader beams. In some embodiments, the signals may not always be transmitted in a parallel fashion and may be emitted in various directions from the device to generate additional coverage with the scanned portion of the specimen.

On the basis of sampled returned ultrasound signals, RF signals are generated and are associated with respective scan lines to represent a characteristic of the specimen at each of multiple locations within the specimen along each of said scan lines. In some embodiments, the multiple locations along each scan line are defined by gates, which define an axial (i.e. depth dependent) portion of scan line (or multiple adjacent scan lines).

In some embodiments, a system may comprise a parallelizable processing unit (PPU) communicatively coupled to said ultrasound transducer. In other embodiments, the PPU may be configured to receive unprocessed or partially processed data associated with the RF signal that was collected remotely and/or at a prior time. Said PPU is operable to concurrently compute from said returned ultrasound signals respective quantitative ultrasound values representative of said characteristic for each of a plurality of said multiple locations in parallel. In some embodiments, the PPU is a graphics processing unit (GPU).

The PPU is configured to be provided with a plurality of discrete sets of raw or pre-processed or processed data, which in some embodiments is provided from a single data access or request (or response thereto), such that each discrete set of data may be processed by the PPU substantially in parallel or concurrently, and in some such cases, simultaneously. In some embodiments, successive parallel outputs of said respective quantitative ultrasound (QUS) values are characteristic of the specimen gates/windows corresponding to locations in the specimen along each of said multiple scan lines. The parallel outputs may be used to characterize tissue or specimen material at locations in the specimen corresponding to each QUS value. In some embodiments, a representative image may be generated to provide a visual representation of one or more tissue characteristics based on the characterized tissue. In some embodiments, each pixel of such an image is based on the QUS value or interpolations thereof associated with the location in the specimen corresponding to the image pixel.

In some embodiments, depth-dependent locations along a single scan line, or a group of adjacent scan lines, may be associated with sampled RF signal data. By measuring over time and aggregating such data, including by calculating a mean signal for a given axial range of sampling (i.e. multiple samples within a single gate, or overlapping gates) or RF signals resulting from a plurality of scan line transmissions, a time-domain signal, or time-based signal may be determined. Lateral windows may be selected wherein multiple time-based signals may be aggregated or calculated independently and then aggregated. All of these calculations over many different gates and lateral windows may be calculated by the PPU concurrently in parallel.

In some embodiments, tissue characterization may be accomplished by determining differences in the frequency-domain of returned signals. Such frequency-based signal indicators include power spectra signals calculated by performing a Fourier Transform or Fast-Fourier Transform on the time-domain signal to obtain frequency-domain information. The resulting frequency-based indicator is frequency-domain signal data, which depending on even subtle changes in tissue characteristics, there can be changes in parameters relating to said frequency-domain signal data. For example, upon a mid-band fit window location and range, a slope therein, and a y-intercept therefrom will, it has been empirically shown, be similar for similarly characterized tissues or materials. Such values may be referred to as further signal parameters.

In some embodiments, there is provided a parallelizable processing device for simultaneously calculating a plurality of QUS values representative of a region of a specimen. A PPU may be provided RF signal data, for example, post hoc from a storage medium, or via a communications medium from a remote measurement or data storage location. Said parallelizable processing unit may be configured to receive from a communicatively coupled ultrasound transducer (possibly via the internet or other communication network), or via a data storage medium as an intermediate, a plurality of ultrasound signals. In some embodiments, data representative of RF signal data may be recalled from storage or even simulated; such PPUs may, in a highly parallelizable manner, determine a variety of QUS parameters, preferably in real-time, even without direct access or inclusion with an ultrasound transducer or other ultrasound device. RF signal data may be collected, pre-collected, or simulated, from a region of interest in a specimen, wherein each ultrasound signal associated with axial scan lines into said specimen are representative of a characteristic of the specimen at each of multiple locations within the specimen along each of said scan lines. In some embodiments, the parallelizable processing device comprises a data bus, which provides an interface between local data storage and/or a network interface (e.g. NIC) and the processor unit. A data bus is a communications interface between two computing elements or devices. The data bus may be specifically configured to accept a high number of data values collected by an ultrasound transducer, each said data value relating to a given ultrasound signal from a given location in said specimen, and provision each of said plurality of data values to respective processors in a processing unit in the PPU. In some embodiments, there may be provided a data storage medium configured to store said plurality of data values and, upon a data request, provide at least some of said plurality of data values; said data storage medium may be configured to accept an output of the data processing of said data values. In some embodiments, the PPU further comprises a plurality of individual processor units, said processor units for concurrently performing the same analysis function in parallel on each of said provided data values. In some embodiments, the individual processor units may comprise ALUs.

Figure 2:
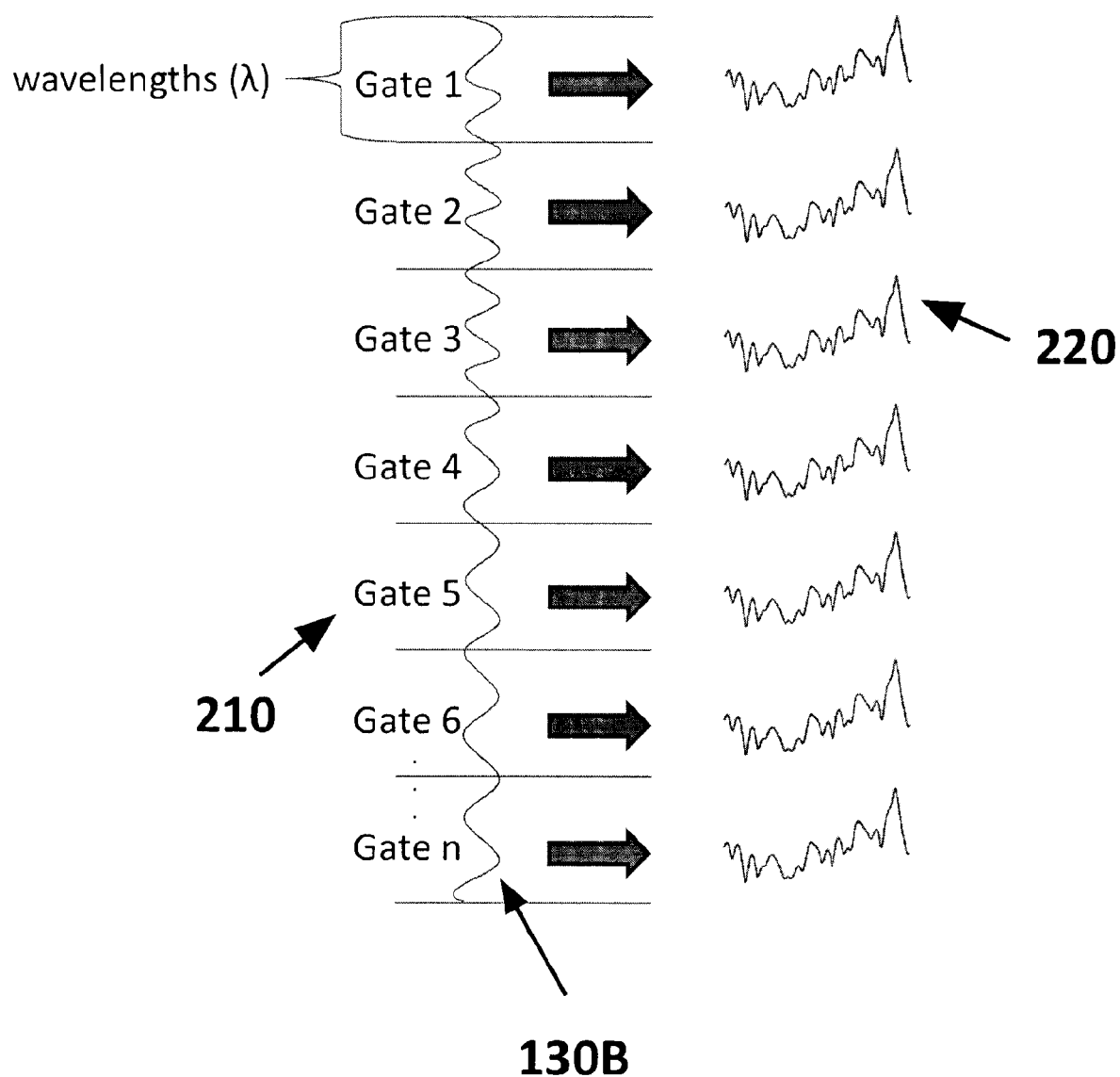
FIG. 2 is a depiction of RF Signal Gating.

With reference to FIG. 2, there is shown an individual scan lines 130B which is processed in segments along the depth of the image as shown in FIG. 2. These segments are known as gates 210. A time-domain signal 220 can be extracted from samples taken within said gates 210.

Figure 3:
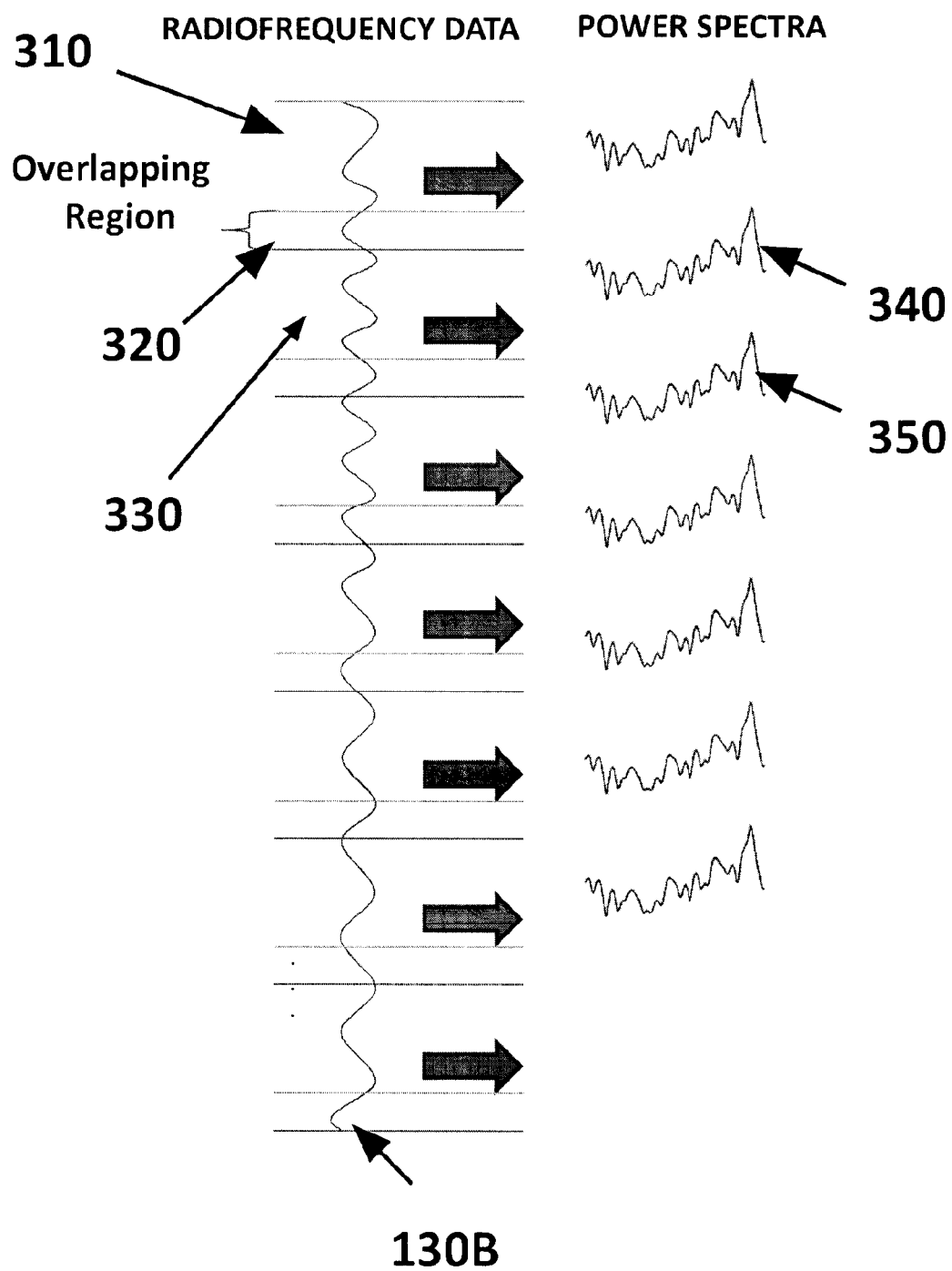
FIG. 3 is a depiction of RF Signal Gating with Overlapping Regions.

The position and length of individual gates vary between QUS application requirements. An example with gates 310, 330 having overlapping regions (e.g. 320) is shown in FIG. 3. Individual power spectra 340, 350 may be calculated for each unique gate in each scan line (even they partially share some RF signal data, due to common samples within the overlap region 320).

Figure 4:
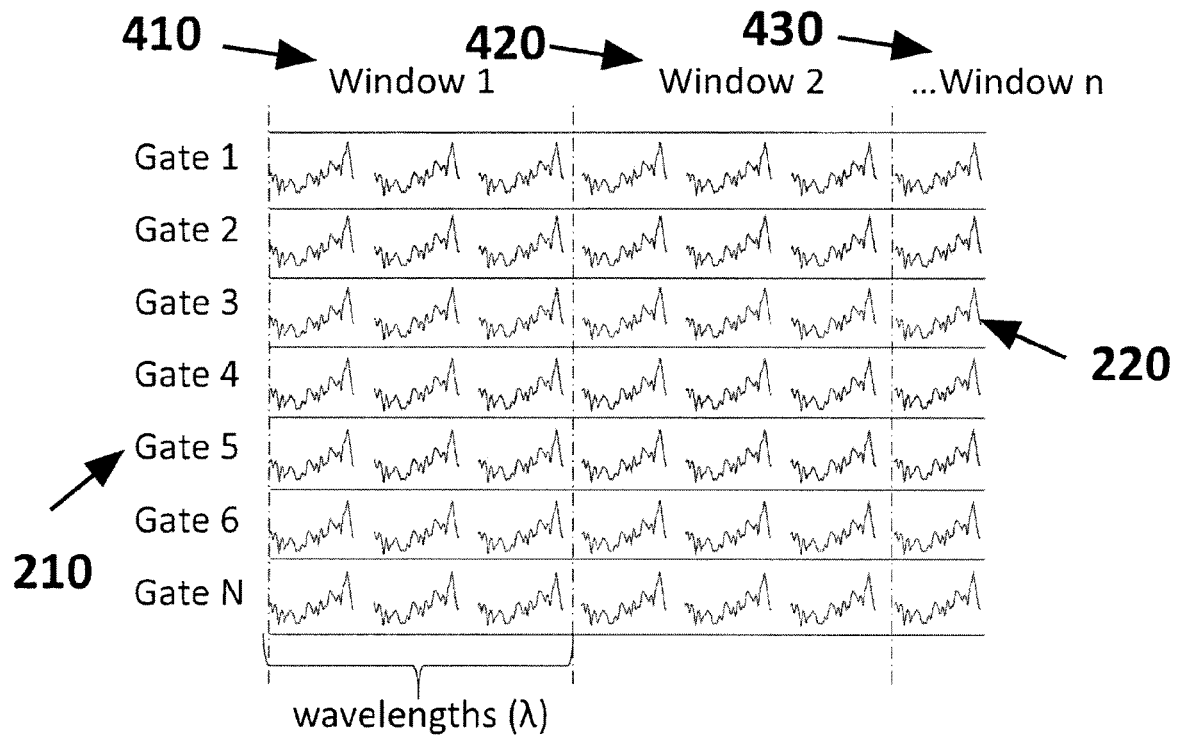
FIG. 4 is a depiction of Gated Spectra Windowing.

Processing of all individual scan lines results in an array of spectral data for each gate 210 as shown in FIG. 4. Depending upon QUS applications, the spectral gate data 220 may be processed axially and laterally. This example averages spectral data laterally into individual windows 410, 420, 430. Window locations and dimensions vary between QUS applications. Windows, such as Window 410 may correspond to a given scan line or a portion of a scan line or a data from at least one scan line.

Figure 5:
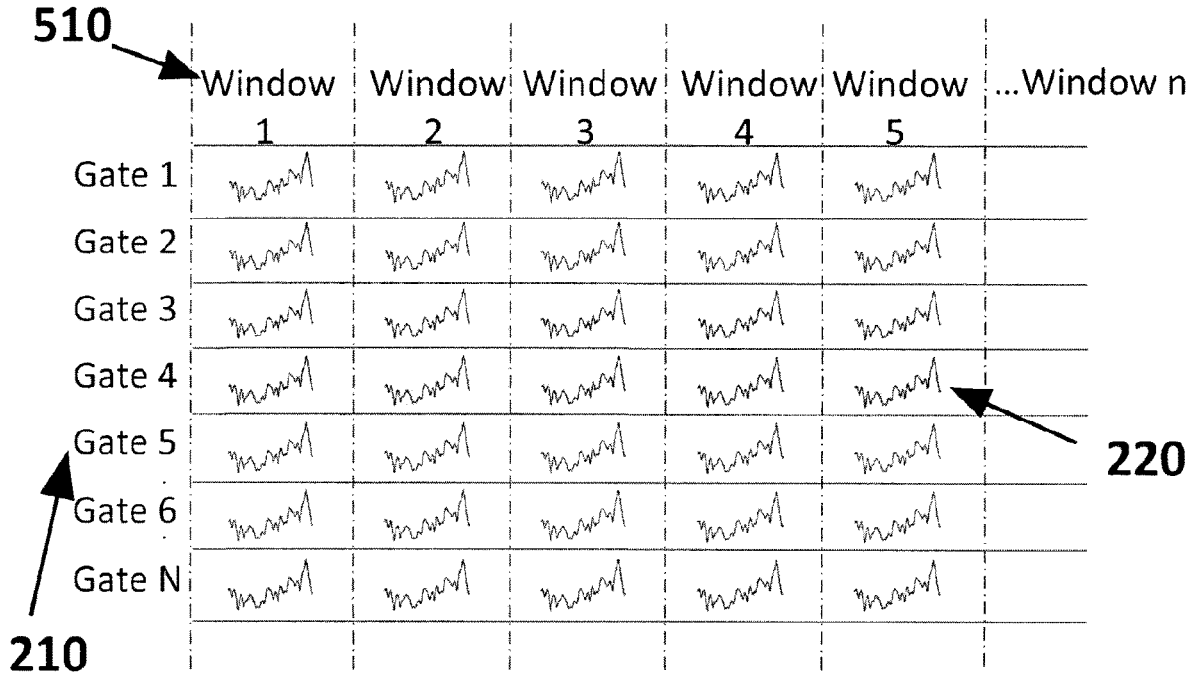
FIG. 5 is a depiction of Averaged Spectral Data.

Spectral data in individual windows may be averaged into a single averaged spectrum within each window, e.g. Window 1 510. Processing of individual windows results in an array of averaged spectral data as shown in FIG. 5.

Referring to FIG. 6, individual averaged (or aggregated) spectral window data are processed and further parameters 610, 630, 650 may be extracted (data outside the mid-band fit, i.e. 620, 640 may be withdrawn from any analysis to keep data clean and to standardize data processing across different windows/gates. Processing of spectral data, and the further parameters may vary between QUS application. The example shown in FIG. 6 obtains QUS parameters through linear regression analysis of averaged (and potentially normalized) power spectra. The three parameters shown are typical examples of QUS parameters of interest. The method and parameters depicted shown are not meant to be an exhaustive list of QUS parameters.

An example of a processed QUS parameter data array is shown in FIG. 7. The figure depicts an example list of QUS parameters 710 which could be generated for each Gate/Window 210, 510 using the example linear regression analysis in FIG. 6. This data may be used in ultrasound tissue characterization applications both for analysis or image formation purposes.

While conventional approaches to computing QUS parameters on standard CPUs (generally characterized with having one or single ALU or processing core, with high degrees of flexibility and low latency due in part to a high degree of control and memory resources) tens of seconds to minutes of processing time in order to obtain QUS parameters for a typical frame of ultrasound radiofrequency data on modern computing platforms. In general, multi-core CPUs are now the norm for computing, however they differ from a PPU in that the programmer may not take control of the cores and rather the system does load balancing of processing requirements and it attempts to spread the processing over the cores in accordance with its load balancing objectives. Although CPU technology has rapidly increased in processing capabilities, the resulting increase in QUS parameter calculations has not afforded the capability processing speeds approaching those required for real time data processing. The inability of traditional CPU computing techniques to compute QUS parameters from ultrasound radiofrequency data has limited the use of the technology to a post-processing paradigm. One drawback to the CPU processing approach, at least for QUS applications, is that it often approaches the solution in a serial manner and does not have the highly parallelized processing capabilities necessary for real time requirements. CPUs are typically designed for low-latency rather than high throughput—control over process functions and reduction in latency is critical, whereas for a PPU, latency is deprioritized from throughput but there may be a trade-off with respect to the level control and memory access to each core. As such, traditional approaches to QUS parameter calculations for the purpose of ultrasound tissue characterization approach the problem in a mainly serial manner using windowing processes. In contrast, and as shown in the pictorial description in FIG. 7, RF data sets are divided into axial regions known as gates and lateral regions known as windows. Although in most cases processing requirements of windows/gates are independent of one another, current CPU approaches largely limit processing approaches to serial solution strategies. Independent windows are processed using various windowing processes such as a sliding window process. This approach serially computes independent windows depicted in FIG. 7 throughout the entirety of the image data set.

Figure 8:
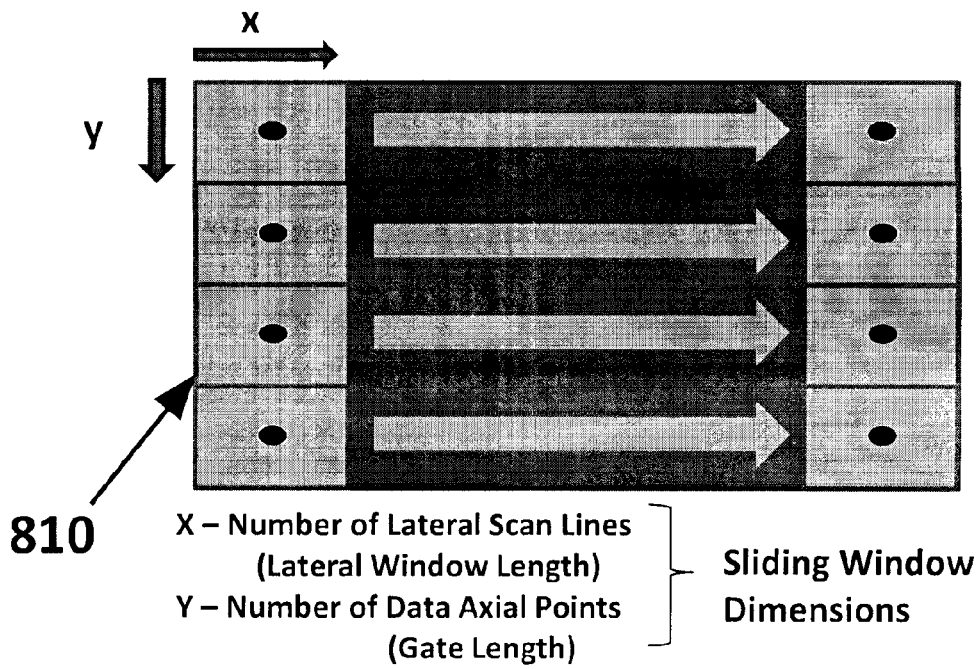
FIG. 8 is a depiction of a Sliding Window Process.

An example of a typical set of processing requirements of individual windows 810 is shown in FIG. 8. This is not meant to be an exhaustive solution to all QUS processing requirements. The processing order and requirements may vary with application and hardware requirements, although the serial nature of the calculation requirements remains.

Figure 9:
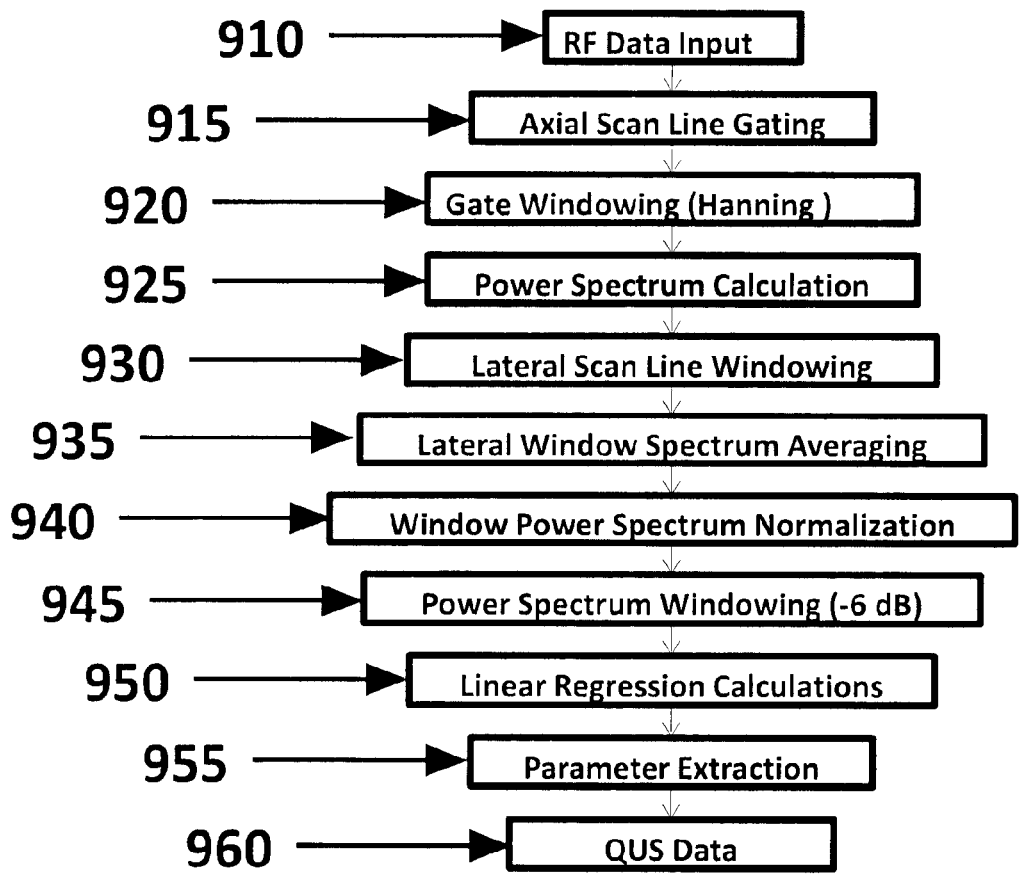
FIG. 9 is a depiction of a typical set of processing requirements of individual windows.

Referring to FIG. 9, there are depicted typical processing steps for calculating QUS parameters for a single gate/window. As shown, these include RF Data input 910, Axial RF data gating 915; Windowing (Hanning window in this example) 920; and Individual RF line Power spectrum calculation 925; followed by a series of serially calculated values 930 to 955, eventually resulting in a QUS value for single gate/window 960, which in turn serially determined for each window/gate.

Figure 10:
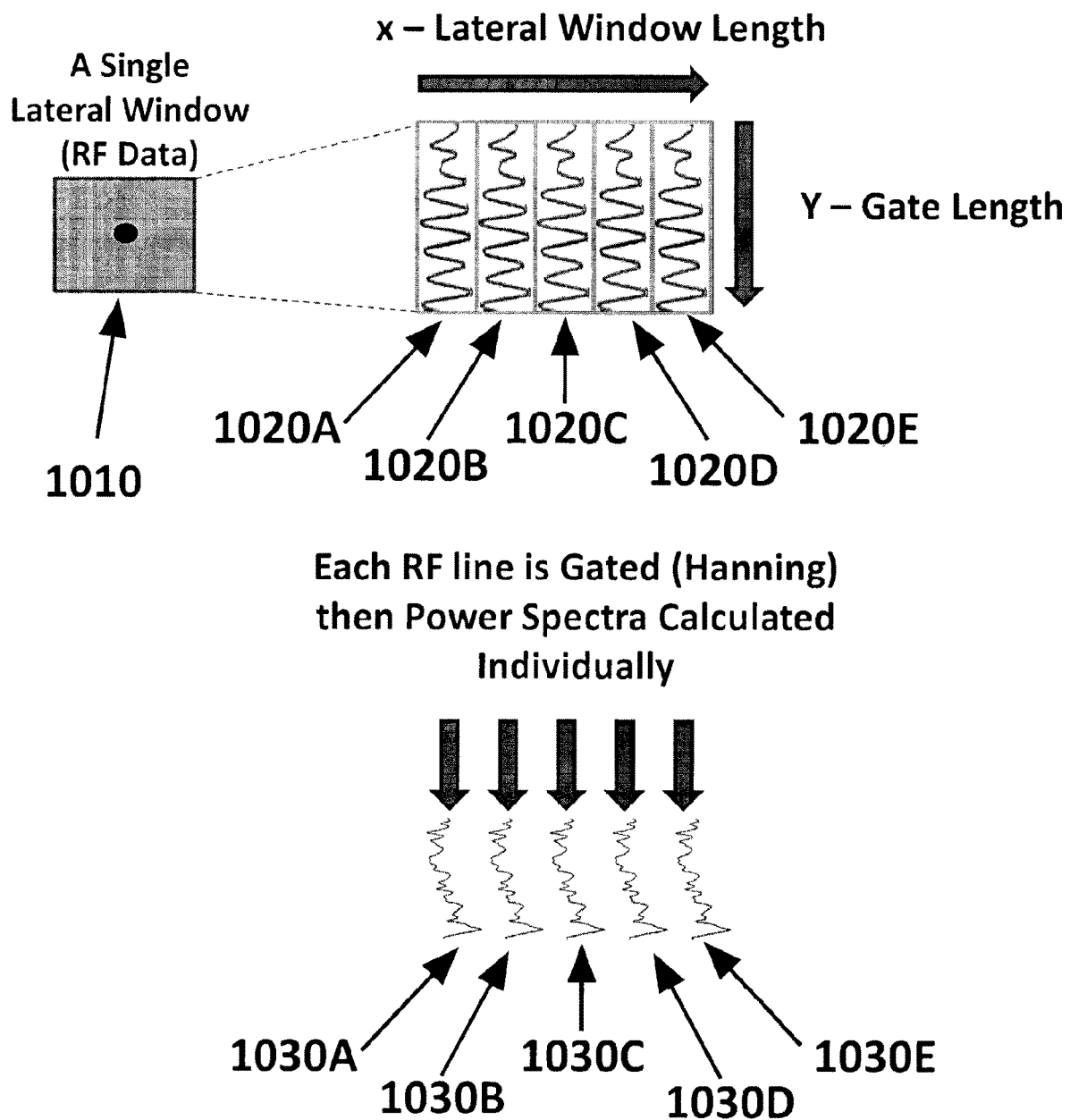
FIG. 10 is a depiction of typical processing requirements for calculating QUS parameters for a single gate/window.

Turning to FIG. 10, Individual Power Spectra 1030A to 1030E have been calculated for a given gate 1010 in each Scan Line through the window in FIG. 10 from sampled RF signal data 1020A to 1020E across a window at said gate 1010. The individual Power Spectra 1030A to 1030E through a window are averaged and often normalized for calibration purposes resulting in a single normalized averaged spectrum for each lateral window.

Figure 11:
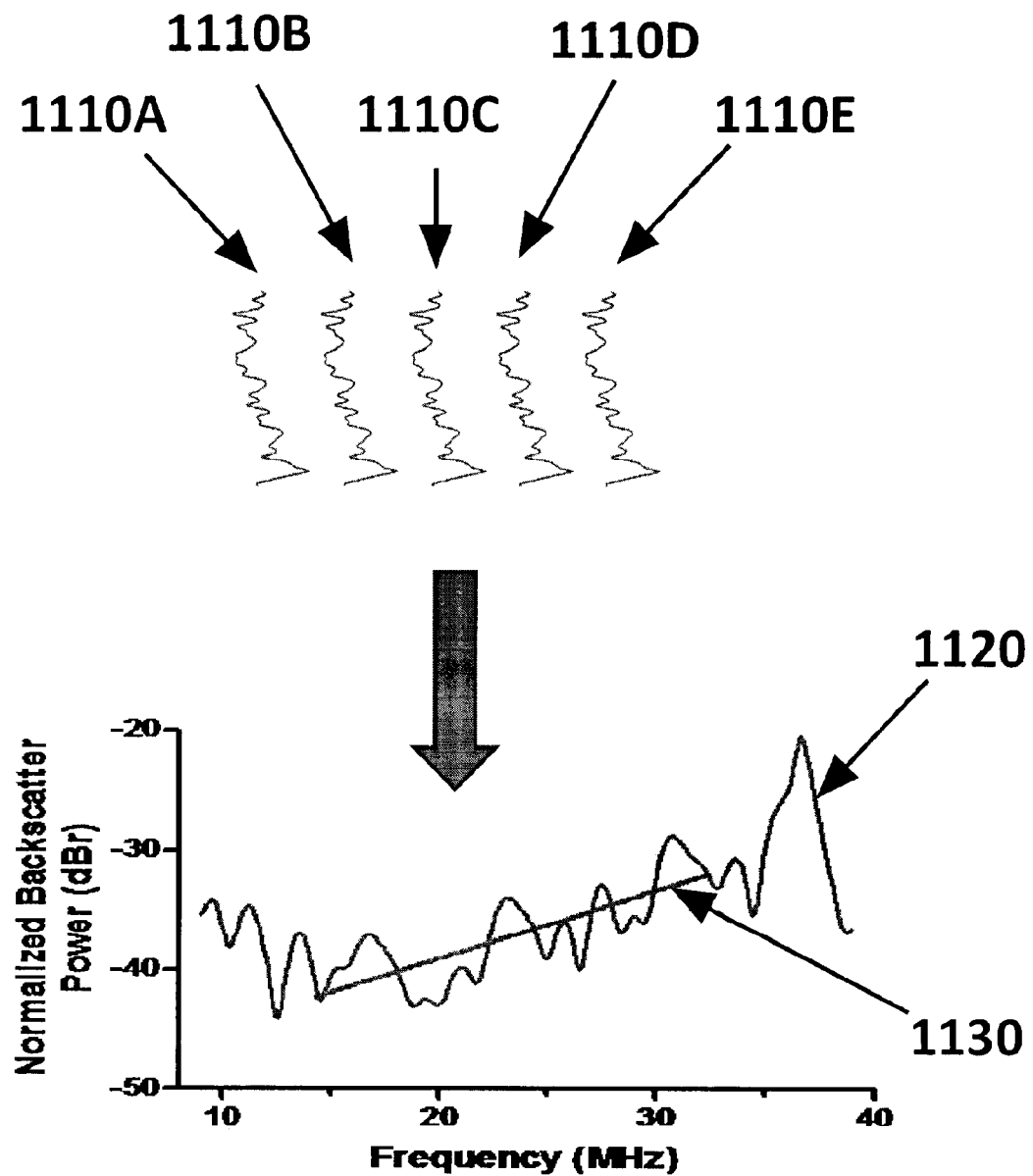
FIG. 11 is a depiction of a Sliding Window Spectrum Averaging.

FIG. 11 depicts a pictorial representation of the linear regression calculations mentioned in FIG. 8 by fitting a best fit line 1130 through a spectral frequency window of the frequency-domain (or frequency-based signal indicator) 1120 as calculated from a set of aggregated (or Hann windowed and averaged) set of time-domain RF signals 1110A to 1110E.

Figure 12:
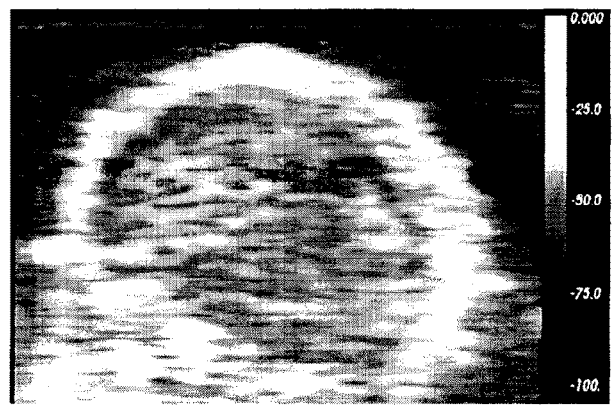
FIG. 12 is a pictorial representation of a colour transfer function applied to spectral parameters and final resulting QUS image.

Once QUS parameters have been generated for all windows/gates throughout the desired image data, a final QUS data array is obtained. This data may be used to obtain quantitative tissue characterization measurements as well as image formation purposes. As best seen in FIG. 12, a pictorial representation of a color transfer function being applied to spectral parameters and final resulting QUS Image is shown. Although an image is formed in this example, the QUS data may be used in any suitable manner, for example, but not limited to, post processing techniques known to those skilled in the art. Furthermore, statistical analysis of QUS data may be performed at this step rather than depicting the resulting QUS image.

Figure 13:
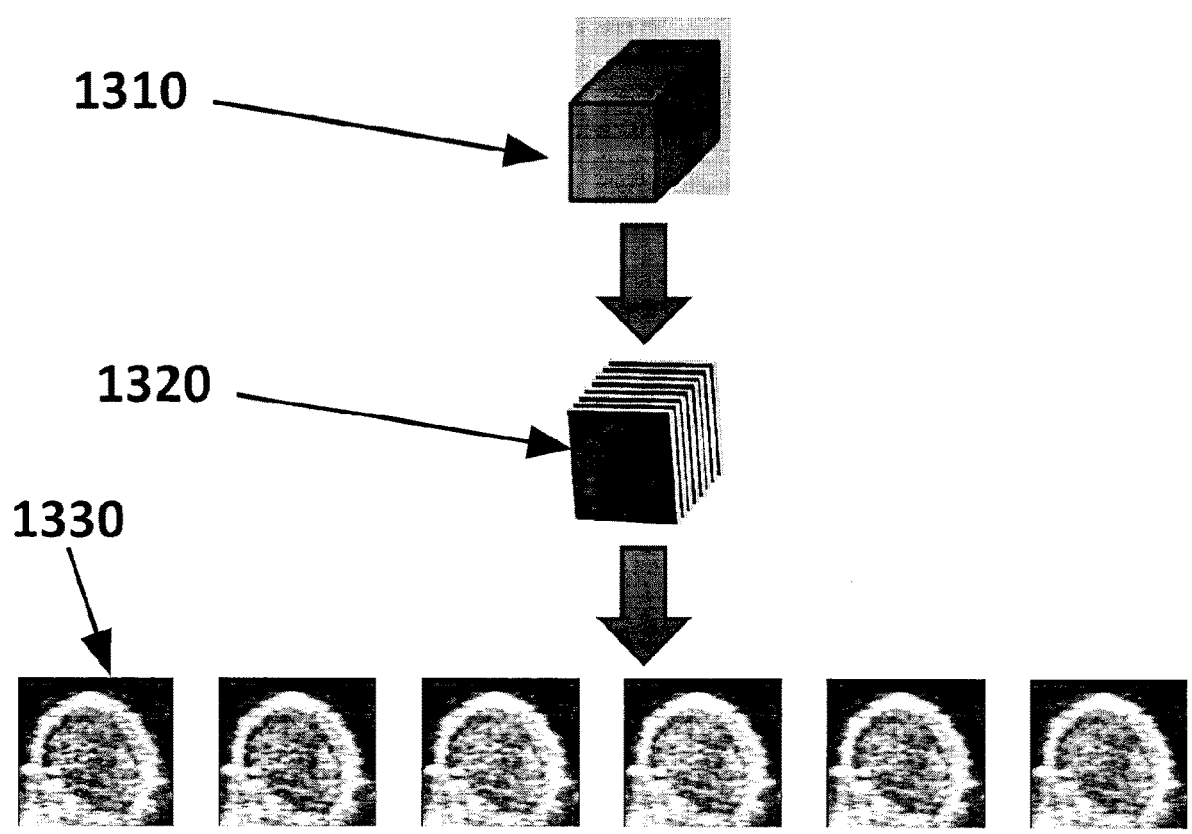
FIG. 13 is a depiction of typical ultrasound data processing.

Turning to FIG. 13, there is depicted a pictorial representation of typical ultrasound data processing for translating multiple adjacent 2-dimensional result sets into a 3-dimensional result set. Initially, a multi-frame data is acquired through a given volume of data 1310 and individual frames are processed using windowing processes to align adjacent layers of the volume 1320. The result is a QUS data set containing desired QUS data parameters for each acquisition frame selected 1330.

In one exemplary aspect, there is provided the use of a PPU that is a GPU employing a graphical processing unit (GPU) Accelerated Spectral Processing (GASP) approach to computing QUS parameters from ultrasound-related RF data for the purposes of ultrasound tissue characterization. This approach involves employing General Purpose Programming GPU (GPGPU) approaches to process ultrasound-related data, including for example, CUDA programming platform and/or SIMD architecture. This allows for highly parallelized processing solutions to be implemented, fundamentally altering the method in which QUS parameters are calculated. Due to the fact that QUS parameters are often calculated independently of one another throughout an RF data set, the process of QUS parameter calculations may be approached in a highly parallelized processing approach making it an ideal application for processing on a computer's GPU.

Figure 14:
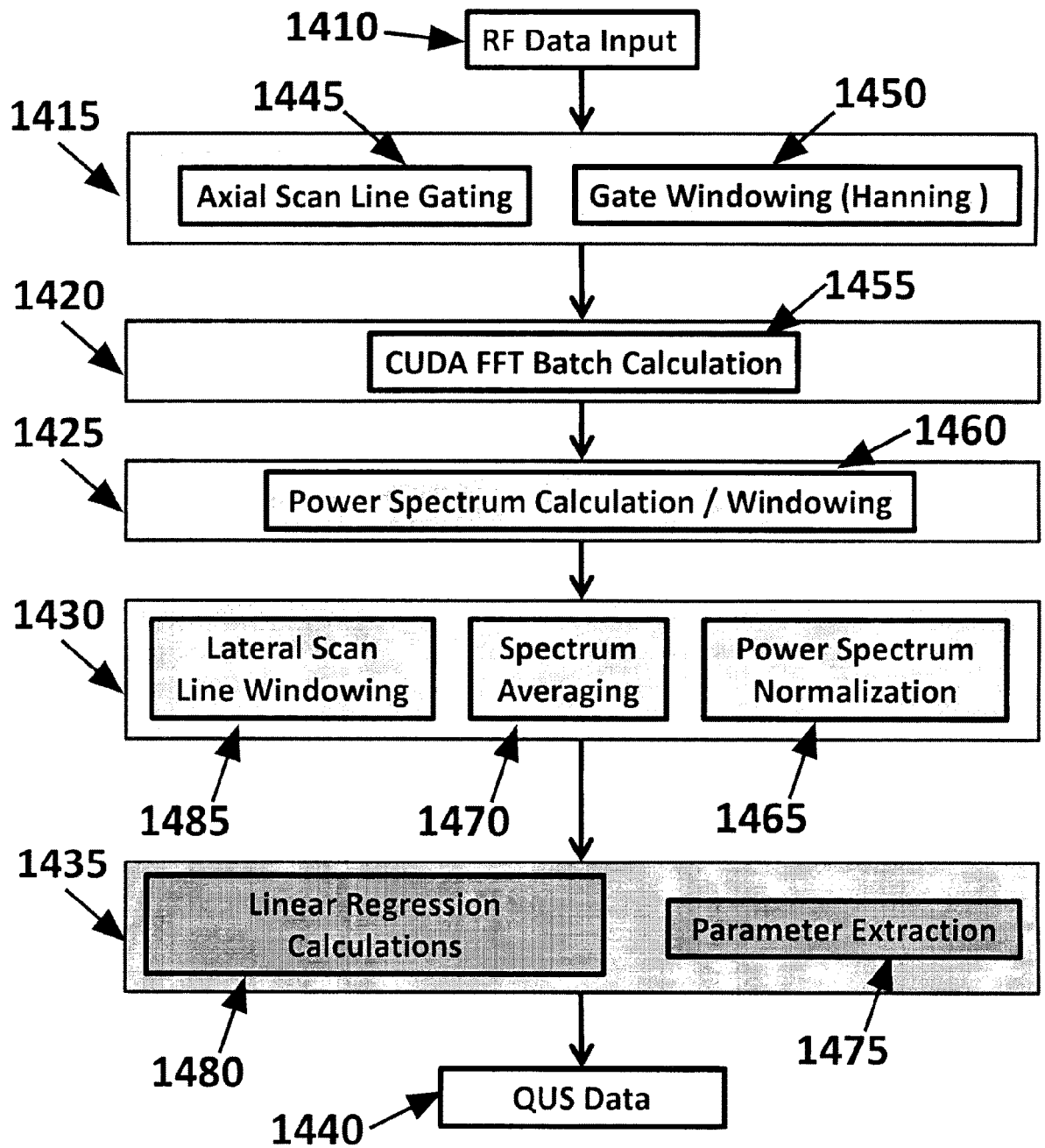
FIG. 14 is a depiction of a single gate parallelization process incorporating GASP.

The system described herein implements a gate level parallelization process, as an example of a GASP system capable of multi-frame per second QUS parameter calculation speeds employing GPU technology. There are provided methods that demonstrate an implementation of the QUS process calculation described in FIG. 14 which is a typical example of QUS processing requirements. The parallelization process shown in FIG. 14 describes a single gate GASP parallelization process through an RF image data set and has been demonstrated to accurately process a typical frame of ultrasound-related RF data with orders of magnitude higher processing throughput when compared to CPU programming approaches. The input data as step 1410 to the PPU constitutes the RF data collected from the ultrasound transducer. At step 1415 RF data associated with gates across the region of interest in the specimen 1445 and time-domain RF signals in each individual gate is mathematically windowed, in this case using Hann windowing 1450. A plurality of these process steps for every gate across the scanned region occurs in parallel in each processor in the PPU. The output is an input to step 1420, which is an FFT batch calculation 1455 for a plurality of gates concurrently in the PPU, which uses CUDA programming methodologies which is specifically designed for highly parallelized processing. At step 1425, power spectra, along with spectral signal windowing across the region of interest in specimen is calculated 1460 in parallel across the region. At step 1430, each of lateral scan windowing 1485, spectrum averaging 1470, and power spectrum normalization 1465, may occur in parallel at each gate, and the calculations for multiple gates may also occur in parallel since the high number of processors in the PPU are specifically configured to perform these operations concurrently. The output of step 1430 is an input to step 1435, which performs linear regression calculations 1480 and parameter extractions 1475 (which calculations may be computed in parallel within a given gate) across a plurality of gates in parallel. The output 1440 is the resulting QUS data for this process. Of course, other QUS values may be determined using the PPU, along with different types of values and mathematical analyses (e.g. the instant subject matter is not limited to linear regression, or indeed regression techniques) may be used to calculate such QUS values by the PPU.

The gate level parallelization process described herein is not meant to be an exhaustive solution to all QUS data processing requirements. This particular example may be scaled based upon application requirements and hardware capabilities to include a given set of gates however does not account for all QUS processing circumstances. Modifications for varying hardware RF data outputs is an example of further extensions to this particular GASP implementation.

In an exemplary embodiment, the following steps are illustrative of one QUS analysis across a portion of a spectrum, which are further depicted in FIGS. 15 through 29. Many of the following exemplary steps are further broken down into sub steps.

In a first step, a single axial gate of RF data is extracted from an input RF data set in a format suitable of use of the CUDA FFT batch computations.

Figure 15:
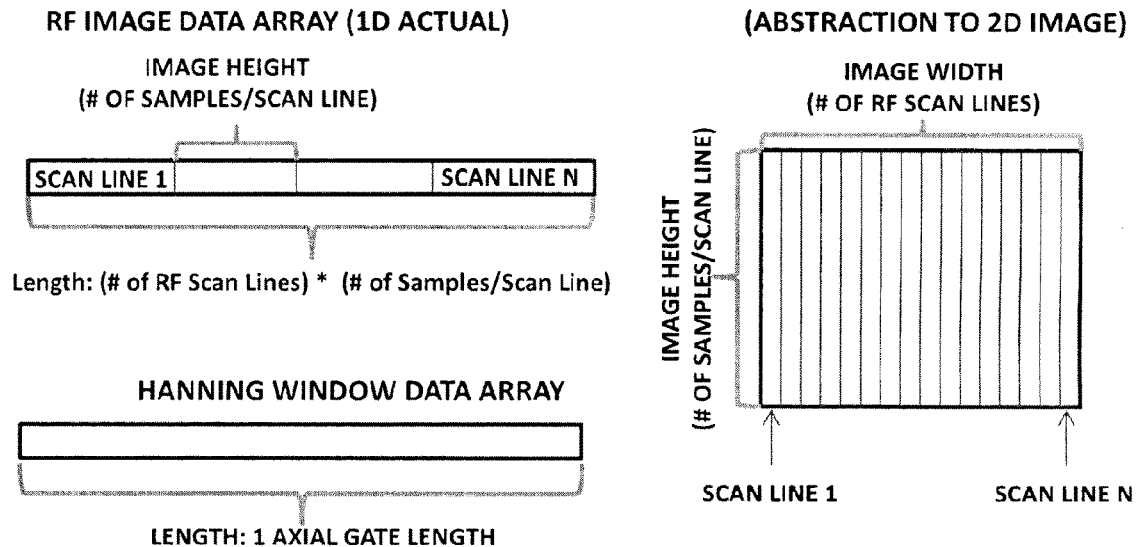
FIG. 15 is a depiction of a data analysis step in accordance with one embodiment of the instant application.

Referring to FIG. 15, there is depicted as an initial sub step (1/3) of step 1, the inputs into the GASP system. Data is comprised of a single array containing the original RF input data set for a single frame of raw ultrasound data. The ultrasound data is stored in scan line major ordering as shown in the image abstraction to two dimensions. As the implementation of this GASP system applies a Hanning window to the input RF data prior to computing the spectra, a Hanning input array is also required.

Figure 16:
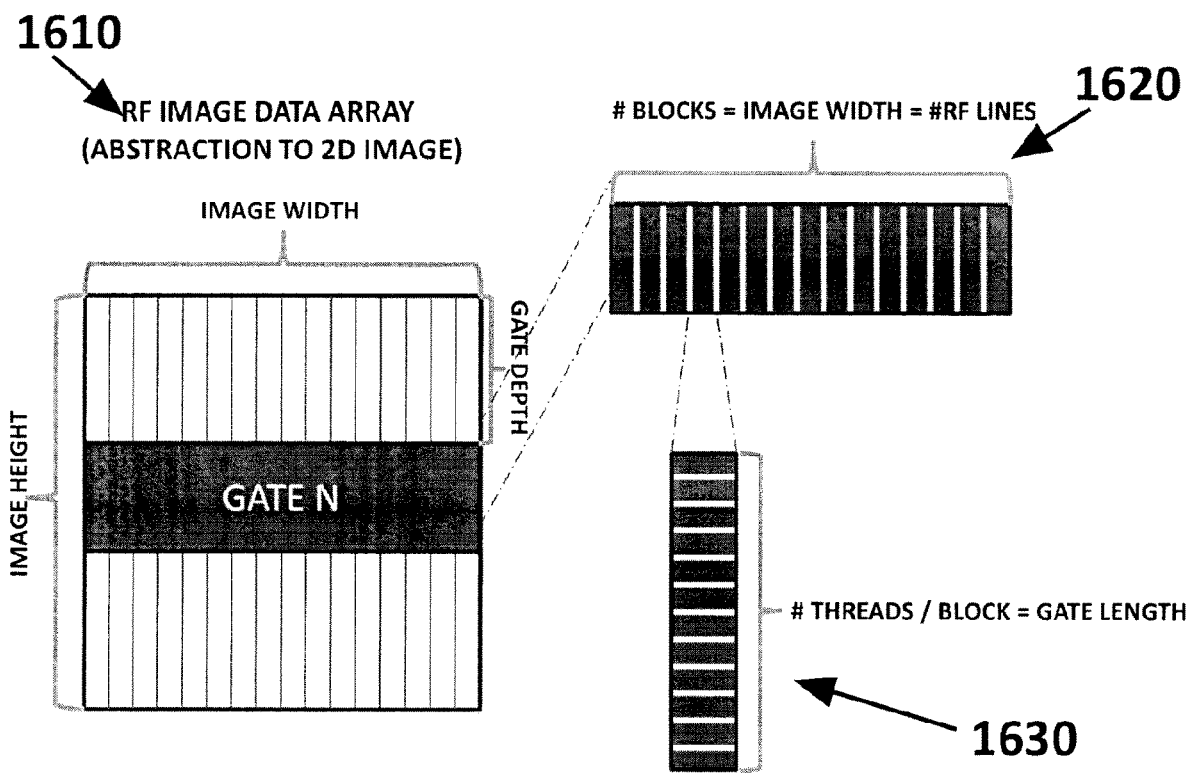
FIG. 16 is another depiction of a data analysis step in accordance with one embodiment of the instant application.

Referring to FIG. 16, there is depicted as an intermediate (2/3) substep of step 1, a pictorial representation of the parallelization process employed for step 1 in the GASP system. At any Gate throughout the input image data, a block of execution threads is executed for every scan line in the data set. Each block is executed with a Gate Length number of threads.

Figure 17:
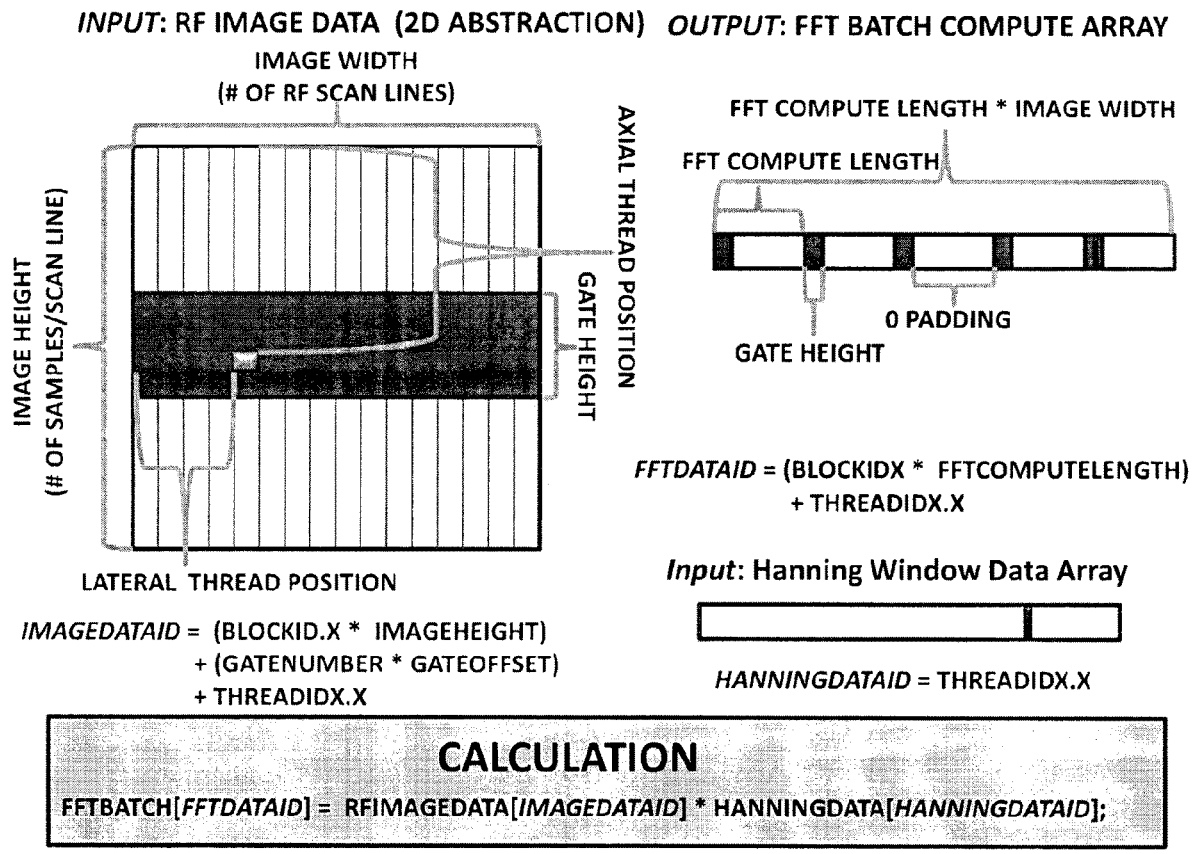
FIG. 17 is another depiction of a data analysis step in accordance with one embodiment of the instant application.

FIG. 17 depicts the final substep (3/3) of step 1, the execution of a single kernel thread described in Step 1(2/3). Each kernel is executed on a GPU SIMD processor and is responsible for copying a single data point from the original input data set, applying the appropriate Hanning windowing, and saving the result to the required location in the FFT-BatchCompute Array.

Figure 18:
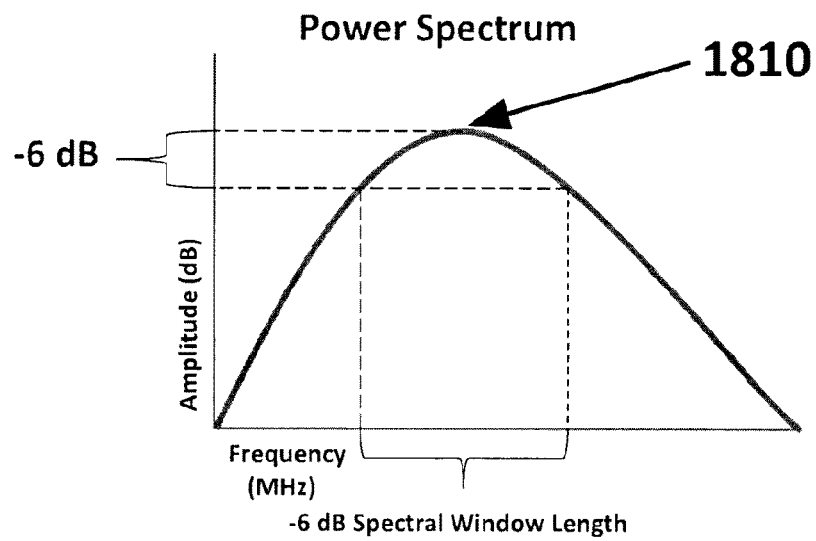
FIG. 18 is another depiction of a data analysis step in accordance with one embodiment of the instant application.

In step 2, the GASP system described in this example computes the power spectrum of the input RF data using the parallel FFT Batch processing capabilities provided by the CUDA development architecture. The input data to this processing step is described in Step 1. The output data of this step contains the computation of the Fourier transform for each scan line segment extracted for the Gate in step 1. FIG. 18 depicts a calculation which is required prior to the execution of Step 3. In order to perform the windowing of the spectral data, the system requires the start and end indexes of the spectral window being used. The example in this figure is a pictorial representation of the calculation of the frequency bandwidth corresponding to a −6 dB window size. Selection of the frequency bandwidth may vary between applications and affect the amount of data processed by the GASP system.

The purpose of the next step, Step 3, is to calculate the logarithmically compressed power spectra from the FFT output data and extract the desired bandwidth described in the Step 3 pre-processing step.

FIG. 19 describes the inputs into step 3 (1/3) of the GASP system. It is comprised of a single data array containing the output from the CUDA FFT Batch computations. As before, the individual FFT data are stored in scan line major ordering as depicted in the 2D data abstraction.

FIG. 20 depicts an intermediate substep (2/3) of Step 3, as a pictorial representation of the parallelization process employed for step 3 in the GASP system. A Block of execution threads is executed for computed FFT in the input set. Each block is executed with a Gate Length number of threads. The Gate Length is computed in the Step 3 pre-processing step.

Figure 21:
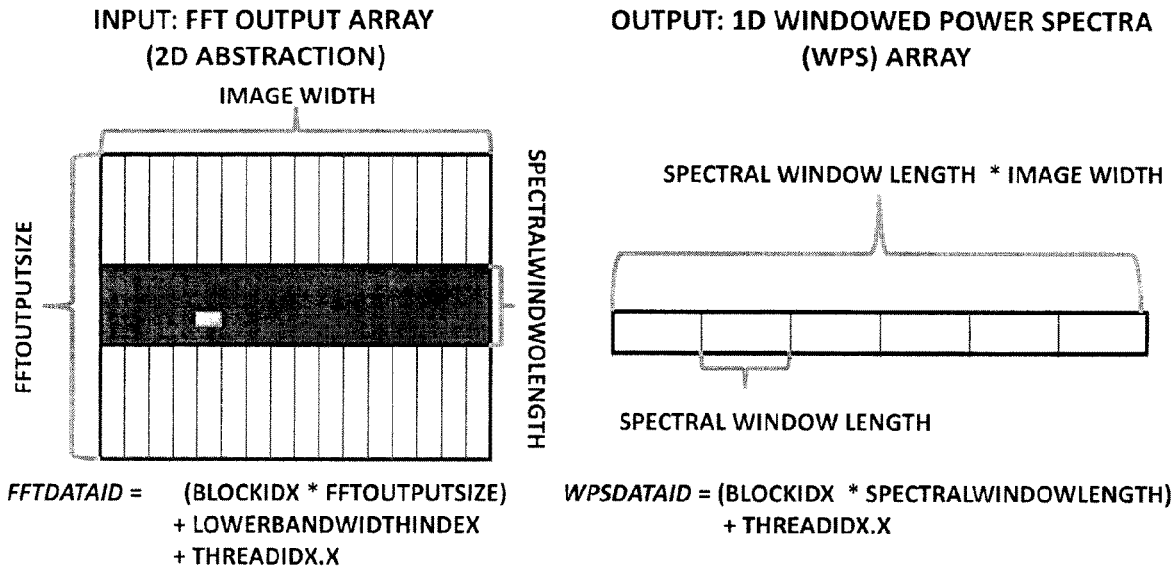
FIG. 21 is another depiction of a data analysis step in accordance with one embodiment of the instant application.

FIG. 21 depicts the final substep (3/3) of Step 3, which is the execution of a single kernel thread described in Step 3: 2/3. Each kernel is executed on a GPU SIMD processor and is responsible for copying two data points from the FFTOutput Array, computing the data point in the logarithmically compressed power spectrum, and saving the result to the required location in the Windowed Power Spectra Array.

The purpose of Step 4 is to calculate an averaged power spectrum for each lateral window for a single gate of windowed power spectra.

Figure 22:
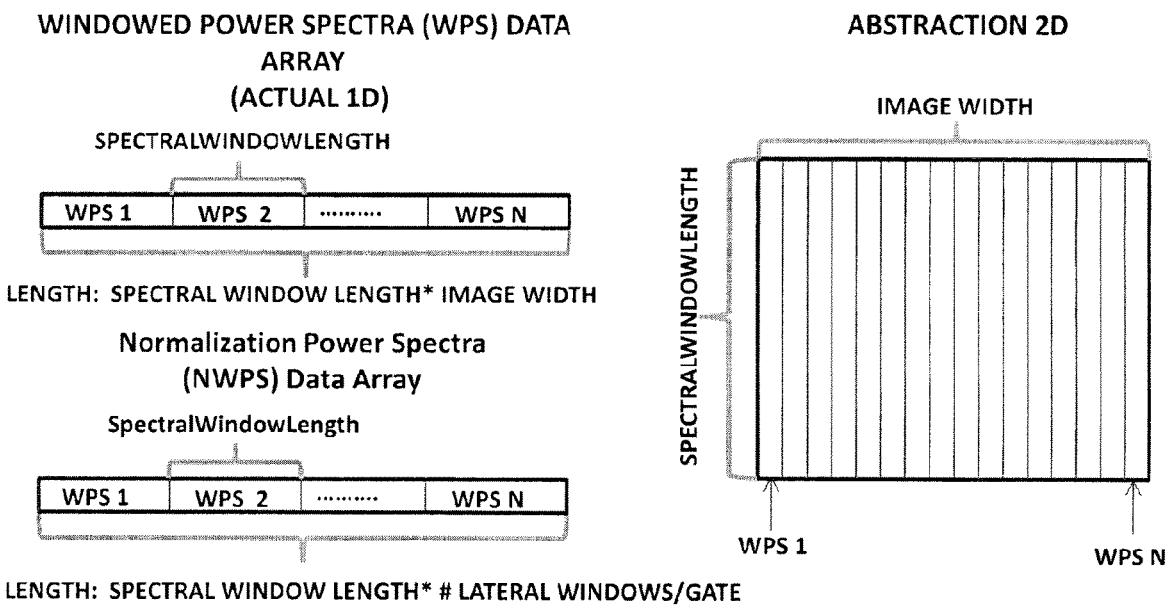
FIG. 22 is another depiction of a data analysis step in accordance with one embodiment of the instant application.

FIG. 22 depicts the initial substep (1/4) of Step 4, and describes the inputs into step 4 of the GASP system. It is comprised of a data array containing the logarithmically compressed power spectra output from step 3. As before, individual Spectra are stored in scan line major ordering as depicted in the 2D data abstraction. Additionally, a second data array containing a previously calculated window averaged spectral data for a corresponding gate of calibration data is input.

Figure 23:
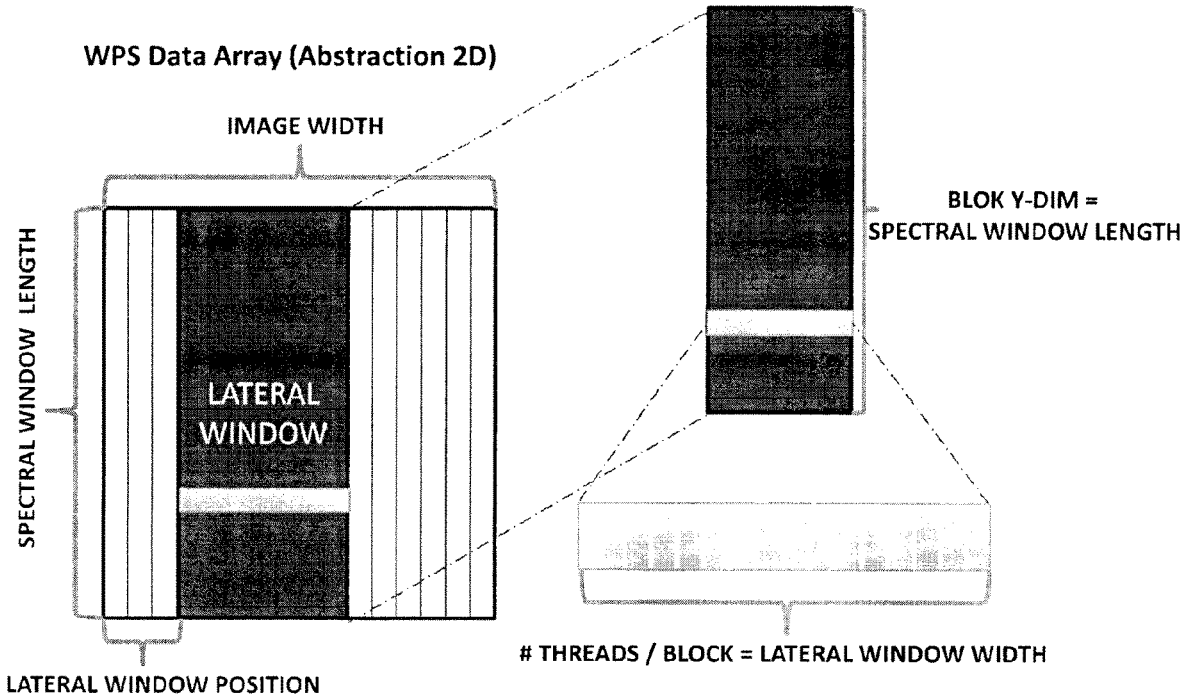
FIG. 23 is another depiction of a data analysis step in accordance with one embodiment of the instant application.

FIG. 23 depicts a first intermediate substep (2/4) of step 4, as pictorial representation of the parallelization process employed for step 4 in the GASP system. A two dimensional Block of threads is executed, one for each window through the gate, and the second for each data point within the spectral window. Each block is executed with a Lateral Window Width number of threads.

Figure 24:
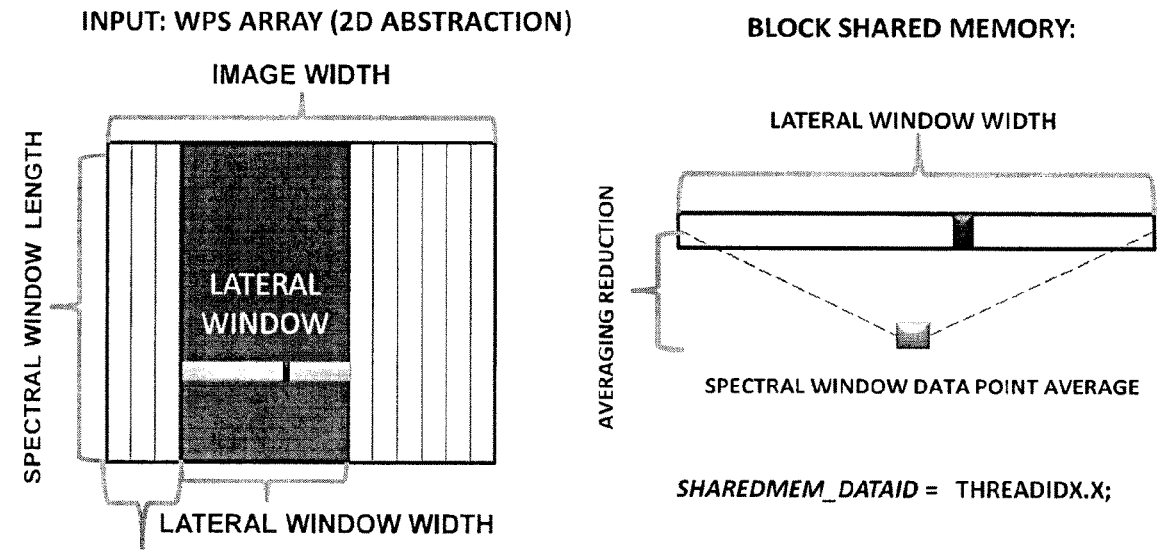
FIG. 24 is another depiction of a data analysis step in accordance with one embodiment of the instant application.

FIG. 24 depicts a second intermediate substep (3/4) of step 4. There is shown the first of two calculations performed for step 4 of the GASP system. Each kernel is executed on a GPU SIMD processor and is responsible for copying a single data point to a point in block shared memory. Once the data points corresponding to a given frequency point are copied to the block shared memory, a reduction operation is performed in order to obtain the average.

Figure 25:
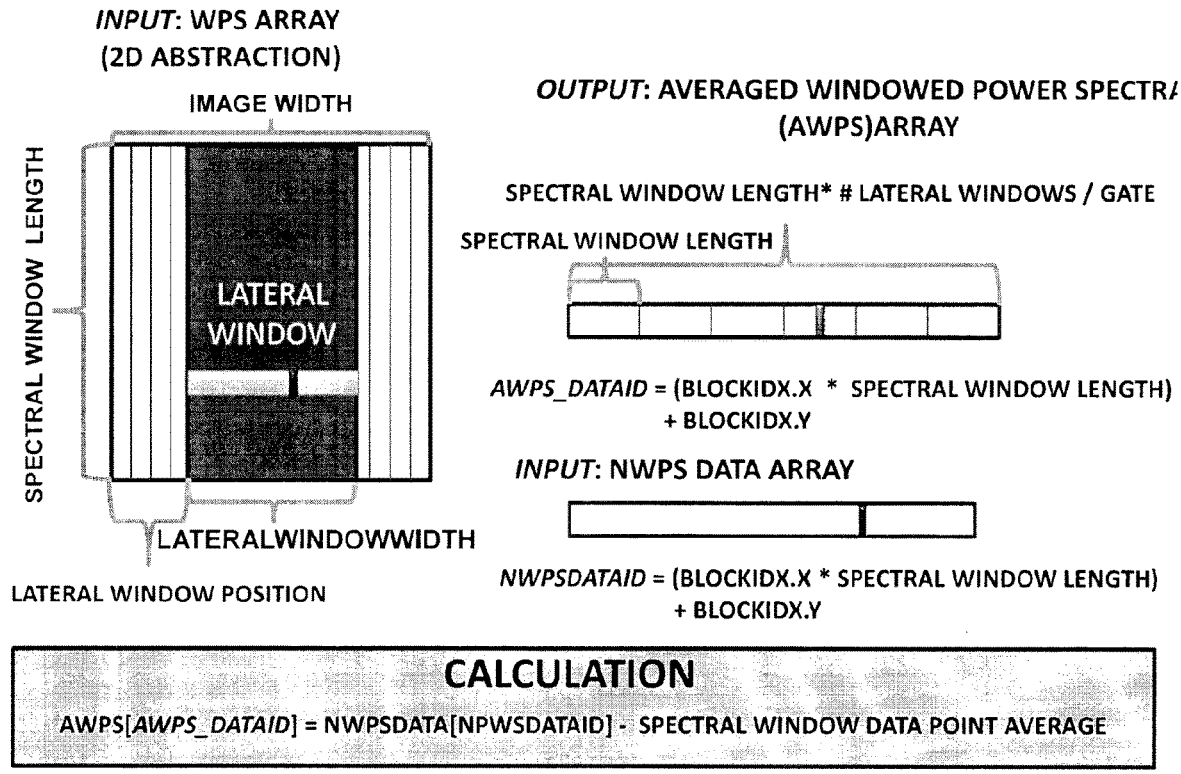
FIG. 25 is another depiction of a data analysis step in accordance with one embodiment of the instant application.

FIG. 25 depicts the final substep (4/4) of Step 4, which is the second of two calculations performed for step 4 of the GASP system. Once the averaged power spectral data point is calculated in Step 4 (3/4), the data point is normalized to the corresponding data point in the Normalization Power Spectra Data Array and saved in the corresponding position in the output Averaged Windowed Power Spectra data array.

The fifth, and in some embodiments, the final step in the GASP system described in this documentation. The purpose of this step is to calculate the best fit line through each of the averaged spectral windows in the Gate and extract desired spectral parameters.

Figure 26:
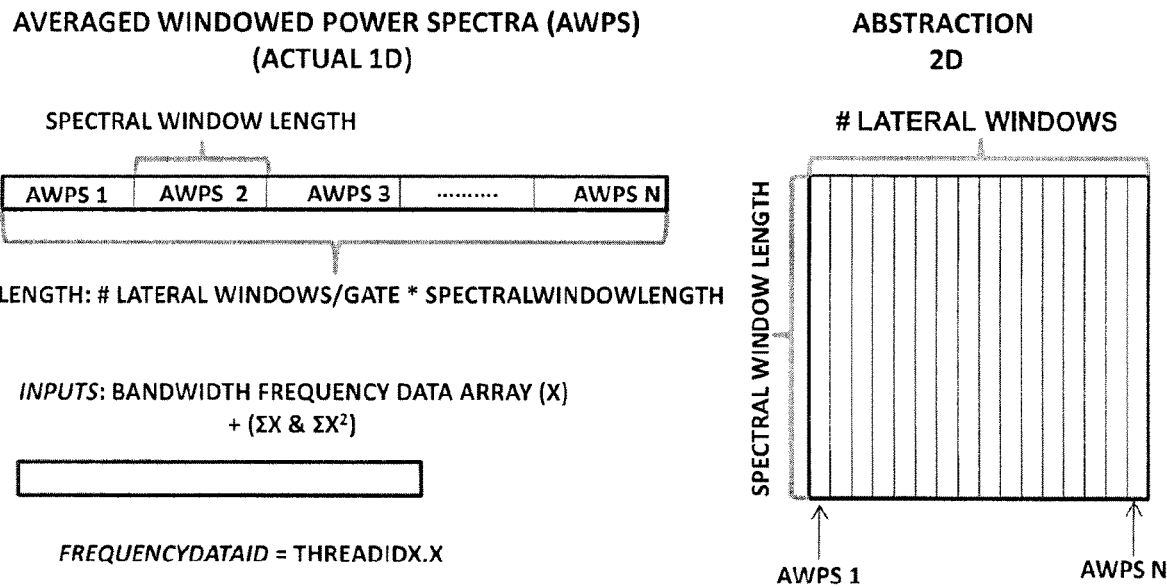
FIG. 26 is another depiction of a data analysis step in accordance with one embodiment of the instant application.

FIG. 26 depicts the inputs into step 5 of the GASP system (or the initial (1/4) substep of step 5). This step is comprised of a data array containing the averaged, normalized, windowed, and logarithmically compressed power spectra output from step 4. Individual averaged spectra are stored in window major ordering as depicted in the 2D data abstraction. Additionally, a second array containing the frequency values corresponding to the X-Axis of the power spectra are also provided as input. The previously calculated sum and sum of squares of the array are provided for linear regression calculations.

Figure 27:
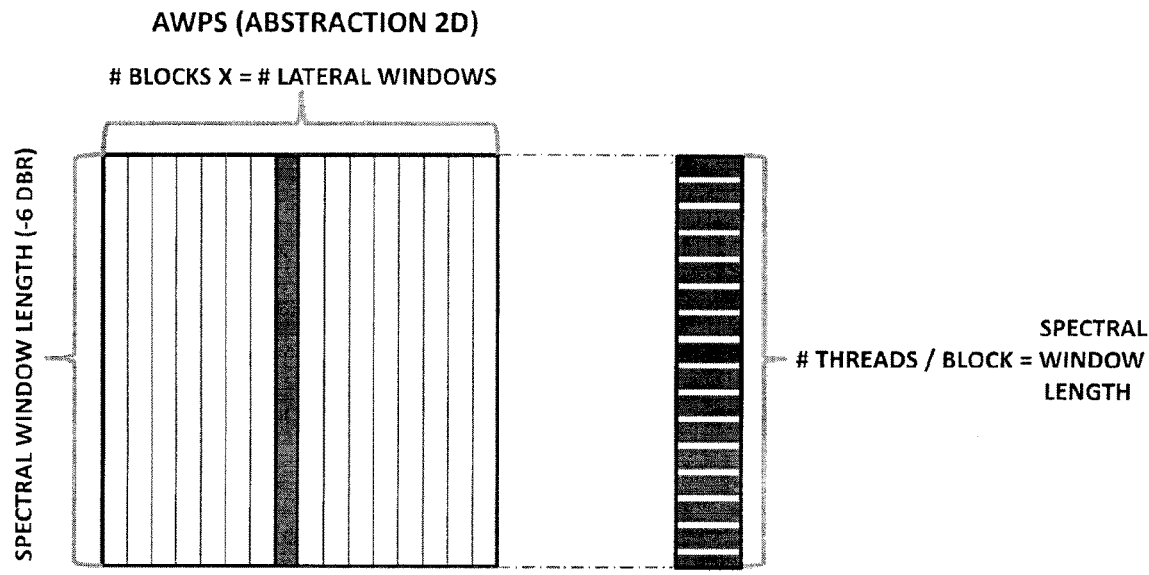
FIG. 27 is another depiction of a data analysis step in accordance with one embodiment of the instant application.

FIG. 27 depicts a pictorial representation of the parallelization process employed for step 5, substep 2/4, in the GASP system. A one dimensional Block of threads is executed, one for each window through the gate. Each block is executed with a Spectral Window Length number of threads.

Figure 28:
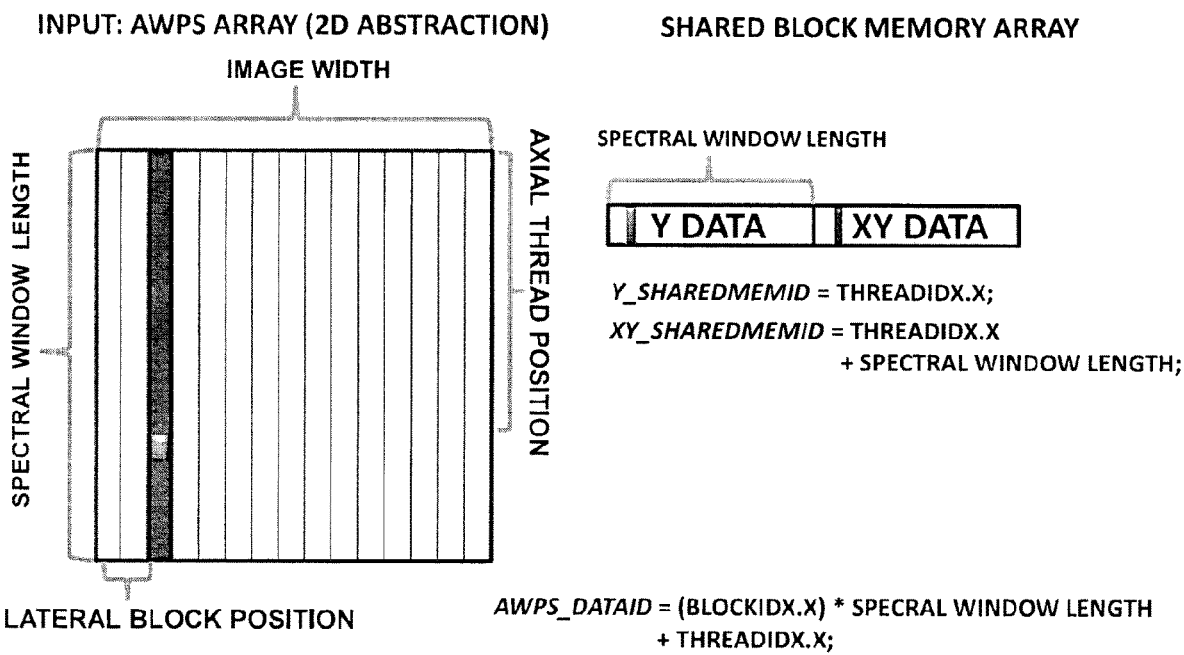
FIG. 28 is another depiction of a data analysis step in accordance with one embodiment of the instant application.

FIG. 28 depicts the first of two calculations performed for step 5, substep 3/4, of the GASP system. Each kernel is executed on a GPU SIMD processor and is responsible for copying a single data point to a point in shared memory as well as multiplying it by the corresponding X-axis input value and copied to second point in shared memory.

FIG. 29 depicts the first of two calculations performed as step 5, substep 4/4, of the GASP system and the final step in obtaining final data parameter arrays. Once the data points corresponding to a given frequency point are copied to the block shared memory locations in Step 5, substep 3/4, two reduction operations are performed in order to obtain the sums. QUS linear regression parameters are calculated and stored to the corresponding location in the QUS Parameter output Array. Several example QUS parameters of interest calculations are displayed.

Referring to FIG. 30 there is depicted an exemplary method of generating a 3-D analysis array or image representative of tissue characteristics that is based on conjoining multiple 2-D analyses or images. Step 1 3010 depicts 3D data capture through a volume. Step 2 3020 depicts the development of a series of aligned and stacked 2D planes that are image data representative of adjacent planar regions or cross sections. Step 3 3030 is a pictorial representation of the parallelized processing of a plurality of QUS data across many gates/windows in the region of interest in the specimen. Step 4 3040 shows an individual image representation, with Step 5 3050 showing the series of aligned adjacent planar regions in the volume. Step 6 3060 shows the constructed 3D volume based on the aligned 2D images.

In some embodiments, there is provided volumetric (three dimensional) computations of quantitative ultrasound parameters for tissue characterization purposes. Volumetric computations of QUS data require additional processing when compared to two-dimensional data requirements as the calculations encompass data from multiple planes of two dimensional ultrasound data in order to compute data for three-dimensional volumetric windows. The ultrasound backscatter volume data set may be acquired through acquisition from multiple two dimensional planes acquired through an acquisition volume, or as three dimensional data sets from two dimensional array transducers which acquire multiple planes of data through a volume simultaneously. There may be provided in some embodiments, the acceleration of the calculation of QUS parameters for tissue characterization purposes by demonstrating a system which encompasses three-dimensional QUS parameter data processing. Accelerating the processing of volumetric QUS calculations may allow for volumetric tissue characterization applications and technologies to be developed and form the foundation of a 4D QUS imaging systems (real or near real time 3D QUS imaging system). The Volumetric Processing Steps may comprise the following:

Two-dimensional RF data sets are generally divided into axial regions known as gates and lateral regions known as windows. These regions encompass portions of the ultrasound data set which are independently processed, and as such highly suitable for a highly parallelized processing approach. The volumetric windowing algorithm furthers the principle to encompass a third dimension in the region of analysis and windowing algorithm resulting in volumetric gates and volumetric windows. Volumetric gates are similar to the two dimensional axial gates as they are depth dependant, however encompass gate data across all planes in the data set at a particular gate depth. Similarly, volumetric windows encompass the same lateral regions as two-dimensional windows; however encompass windowed data across multiple planes of data at a particular depth. The number, location and size of volumetric gates and windows processed are application dependant.

The following outlined steps are meant to demonstrate an extension of the two dimensional windowing process into a three dimensional application, and are not meant to be an exhaustive solution to all QUS processing requirements. The processing order and final spectral calculation method/parameter of interest may vary with application and hardware requirements, although the nature of the calculation requirements remains.

Figure 32:
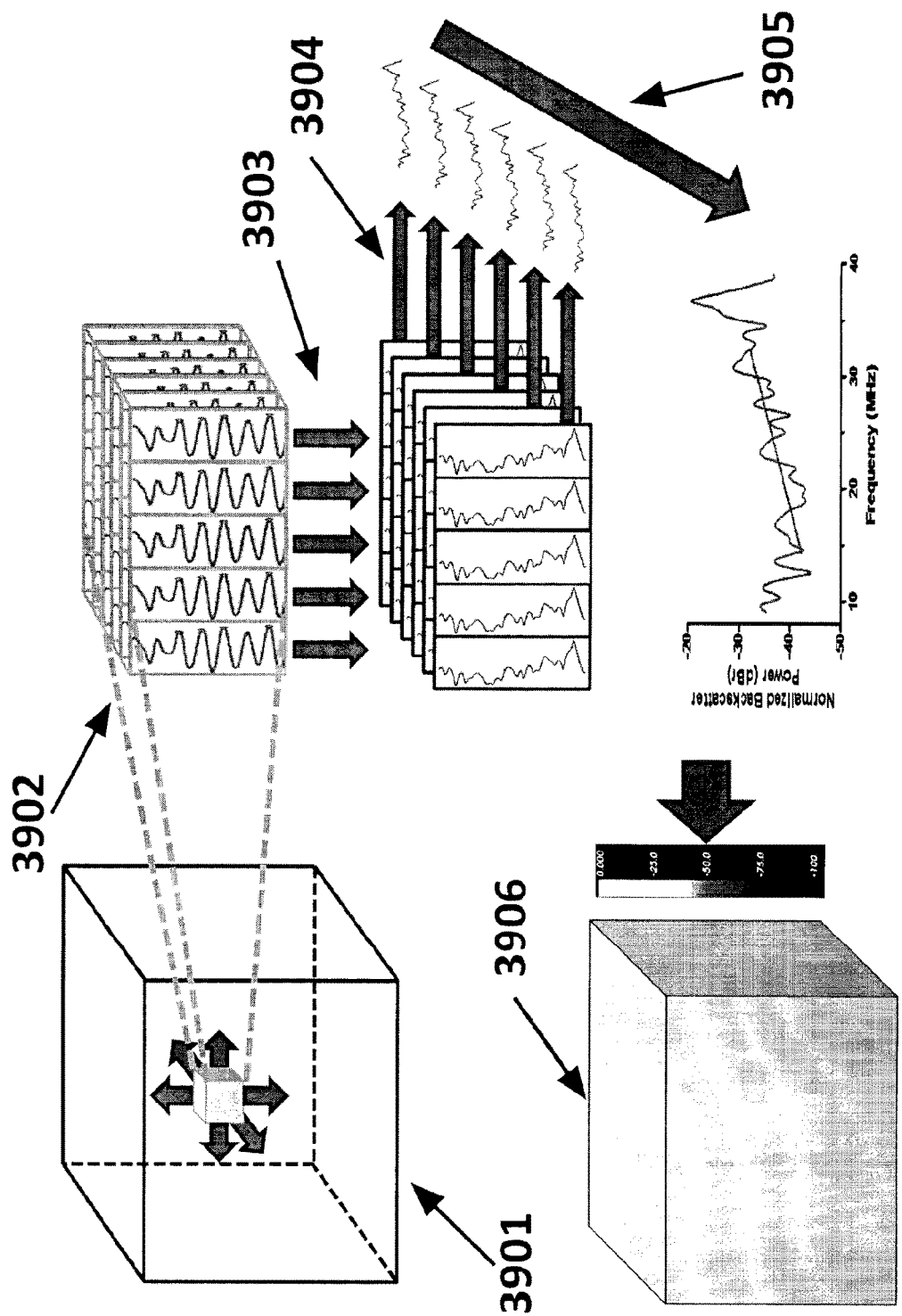
FIG. 32 is a depiction of a volumetric ultrasound analysis.

Independent volumetric windows may be computed using various windowing methods in this instance employing a sliding volume process. This approach computes independent volumetric windows 3901, as depicted in FIG. 32 throughout the entirety of the volume data set. FIG. 32 represents a pictorial representation of a sliding volume employed 3901 in volumetric windowing and depicts a three dimensional volume of acquired ultrasound-related RF data. The volumetric window 3901 depicted represents three-dimensional regions of ultrasound backscatter data which are independently calculated across three axes.

An example of a typical process flow for volumetric windows is shown in FIG. 32. This is not meant to be an exhaustive solution to all volumetric QUS processing requirements. The processing order and requirements may vary with application and hardware requirements, although the independent nature of the individual volumetric window calculation requirements remains.

Referring to FIG. 32, individual power spectra 3902 have been calculated for each Scan Line through the volumetric window 3901. The representation depicts a three dimensional volume of acquired ultrasound-related RF data. The volumetric window depicted represents multiple planes of two-dimensional regions of ultrasound backscatter data. Volumetric windows represent independently calculated regions of analysis across three axes. Independent spectral calculations 3903 are performed for each RF data scan line employing a gate length number of data samples. The system described employs the same window width across each plane in the volumetric window, as such averaged power spectra are calculated independently for each plane 3904 and the resulting two dimensional window averages averaged in order to obtain a single averaged spectrum representing three dimensional spectral data for the volumetric window 3905.

FIG. 32 depicts a pictorial representation of spectral calculations performed during volumetric window processing. The representation depicts spectral data 3904 which has been computed across multiple imaging planes averaged to acquire a single averaged power spectral 3905 per plane for each volumetric window. The individual Power Spectra 3904 through a window are averaged and often normalized for calibration purposes resulting in a single normalized averaged spectrum for each volumetric window.

FIG. 32 depicts a pictorial representation 3905 of linear regression calculations by fitting a best fit line through a spectral frequency window generated during volumetric window processing. The representation depicts averaged spectral data which has been computed across multiple imaging planes averaged to acquire a single averaged power spectral representing the data for each volumetric window. Once QUS parameters have been generated for all volumetric windows/gates throughout the desired volumetric data, a final volumetric QUS data array is obtained. This data may be used to obtain quantitative tissue characterization measurements as well as image formation purposes. A pictorial representation of an image transfer function being applied to spectral parameters and final resulting volumetric QUS visualization 3906 is shown. Although an image is formed in this example, the volumetric QUS data may be used in any suitable manner, for example, but not limited to, post processing techniques known to those skilled in the art. Indeed, the image formation 3906 in FIG. 32 is a pictorial representation of a particular one or more characteristic of the volumetric region of interest, rather than, e.g., an image of what the volume would look like to an observer.

Figure 31:
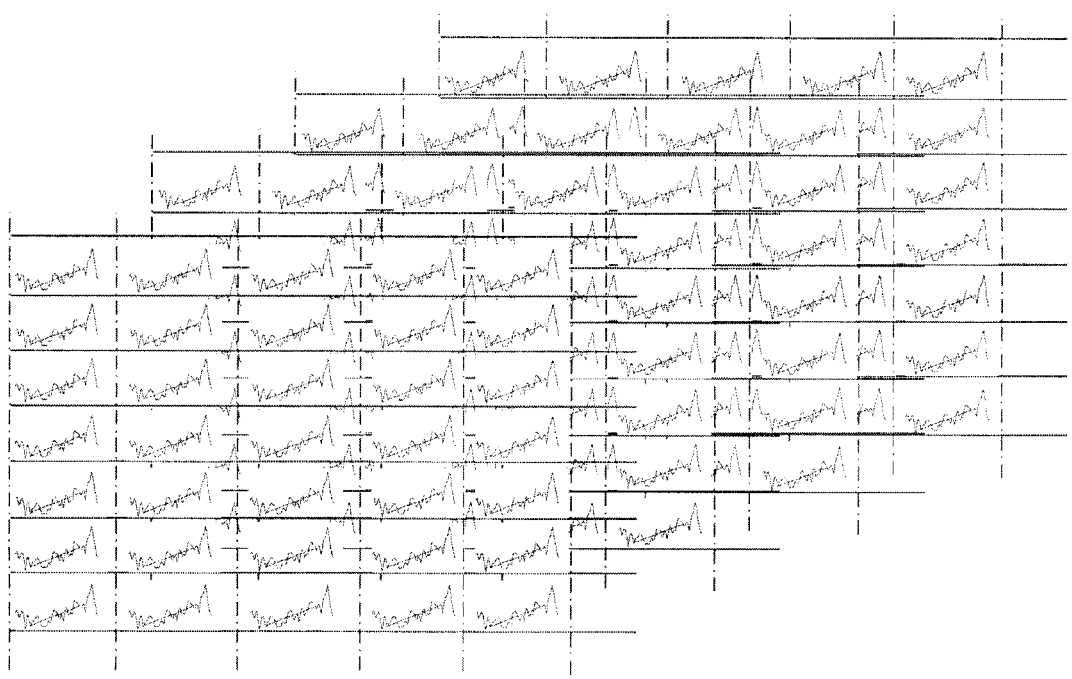
FIG. 31 is a depiction of volumetric gates/windows of a specimen.

FIG. 31 shows the 3-dimensional representation of the power spectra.

FIG. 32 shows one embodiment of an overview of the process flow for volumetric analysis of the specimen materials characterization.

Figure 33:
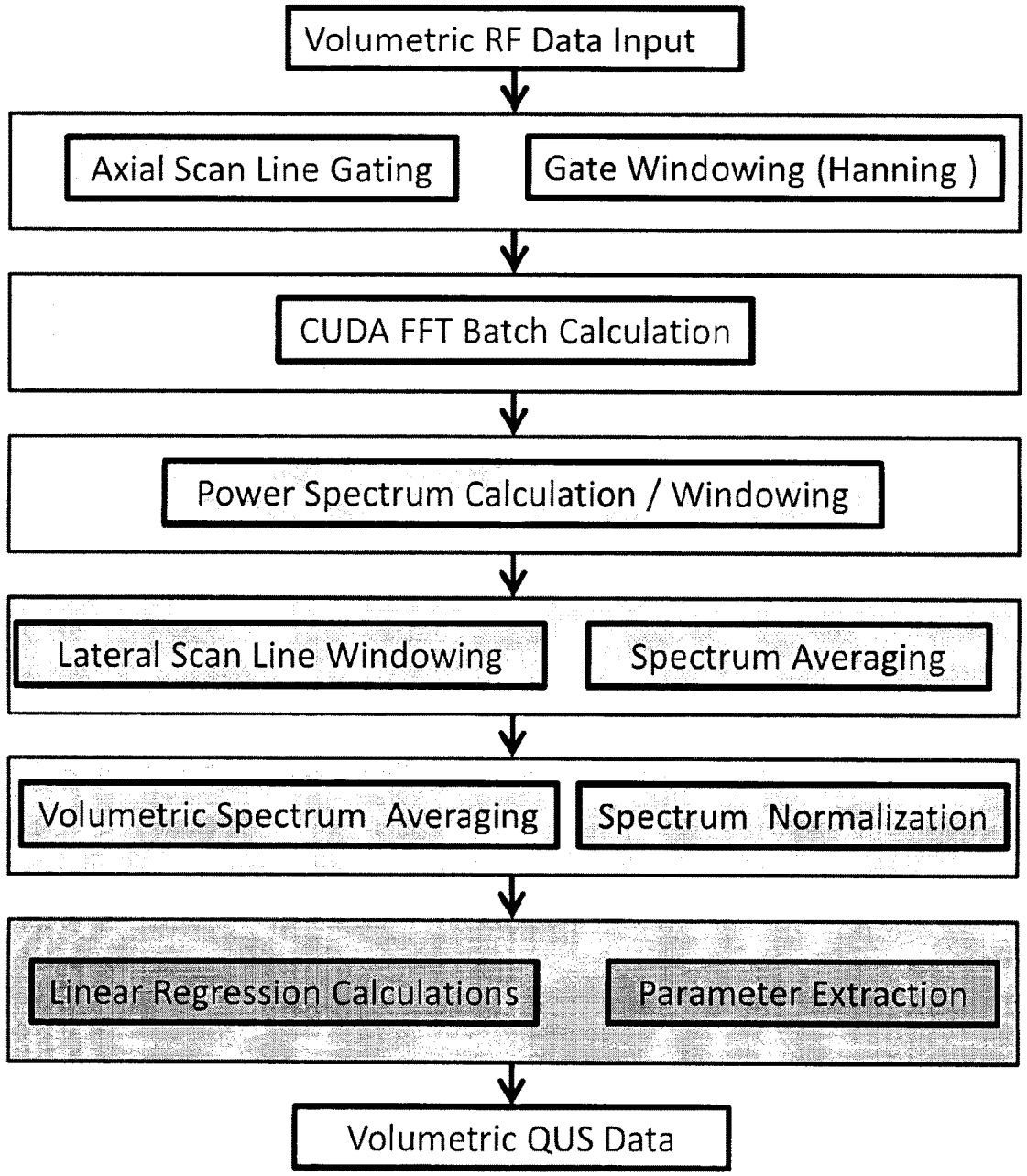
FIG. 33 is a depiction of a single gate parallelization process incorporating GASP for volumetric analysis.

The volumetric gate level parallelization process described herein and shown in more detail in FIG. 33 is not meant to be an exhaustive solution to all volumetric QUS data processing requirements. This particular example may be scaled based upon application requirements and hardware capabilities to include a given set or subset of volumetric gates however does not account for all QUS processing circumstances. Modifications for varying hardware RF data outputs or processing hardware limitations are examples of further extensions to this particular volumetric GASP implementation.

In an exemplary implementation, QUS value determination may occur in the following steps. In Step 1, the purpose of the first step is to extract a single axial volumetric gate of RF data from an input RF image data set and order the data in a manner suitable of use of the CUDA FFT batch computations. This example includes a Hanning windowing of the gated RF data. In some embodiments, inputs to this step may include (i) RF Image Data as a 1D array containing multiple planes of data scan line major ordering and (ii) Hanning Window Data as a 1D array containing Hanning window factors.

Figure 34:
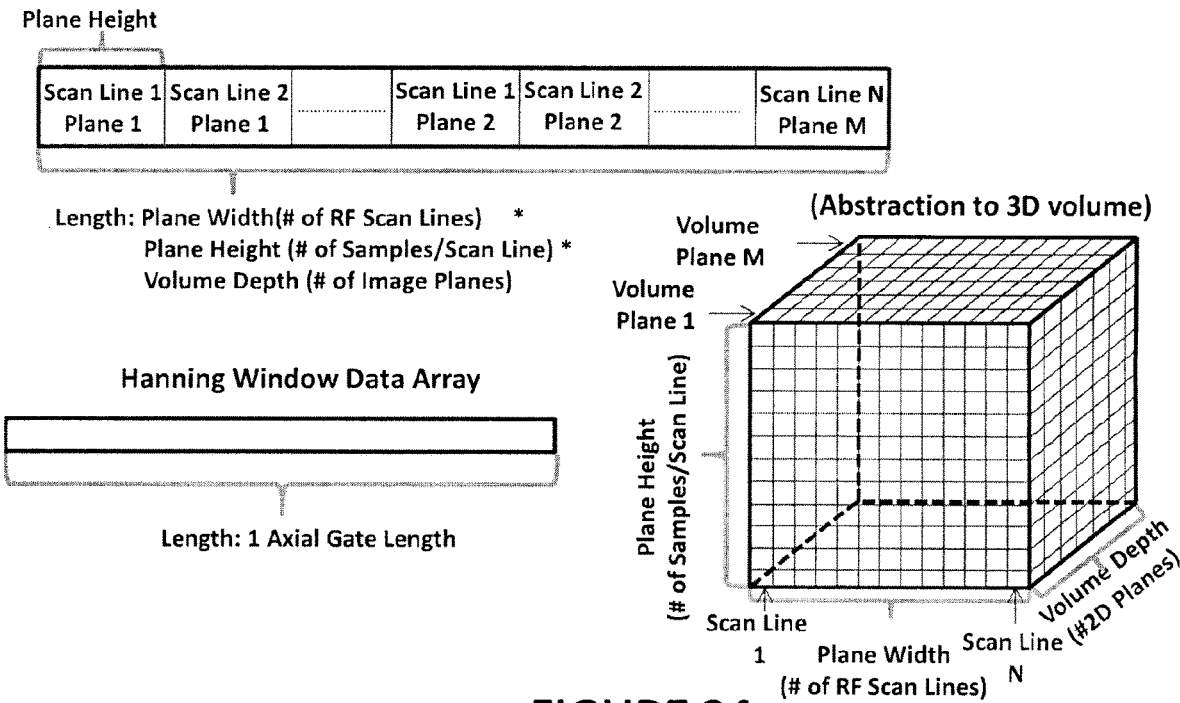
FIG. 34 is a depiction of a data analysis step in accordance with one embodiment of the instant application.

As shown in FIG. 34, at step 1 (Substep 1/3), data is comprised of a single array containing the original RF input data set for a volume of raw ultrasound data. The ultrasound data is stored in scan line/plane major ordering as shown in the image abstraction to three dimensions. As the implementation of this GASP system applies a Hanning window to the input RF data prior to computing the spectra, a Hanning input array is also required.

Figure 35:
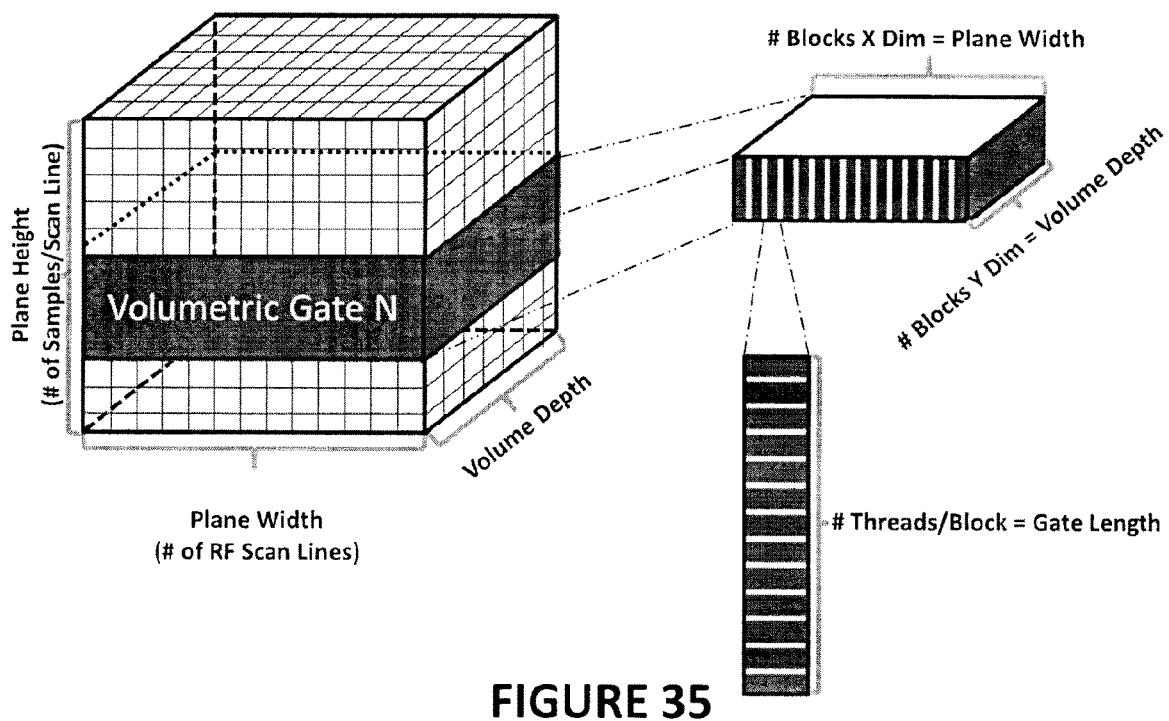
FIG. 35 is another depiction of a data analysis step in accordance with one embodiment of the instant application.

FIG. 35 depicts a visual representation of step 1 (Substep 2/3). At any volumetric gate throughout the input volume data, a Block of execution threads is executed for every scan line in in every plane the data set. Each block is executed with a Gate Length number of threads. This step may facilitate a parallelization strategy, that is that each volumetric gate is processed employing a plane width by volume depth grid of blocks. Each set of RF data from a respective scan line may be processed by a block of Gate Length # of threads and each thread may process a single RF value.

FIG. 36 depicts a visual representation of step 1 (Substep 3/3). Each kernel is executed on a GPU SIMD processor and is responsible for copying a single data point from the original input data set, applying the appropriate Hanning windowing, and saving the result to the required location in the FFTBatchCompute Array. In some embodiments, a kernel is copied as a single value from RF data into FFT Batch Compute array and multiplied by the windowing factor (# Blocks=Image Width*Volume Depth and # Threads=Gate Height).

Figure 37:
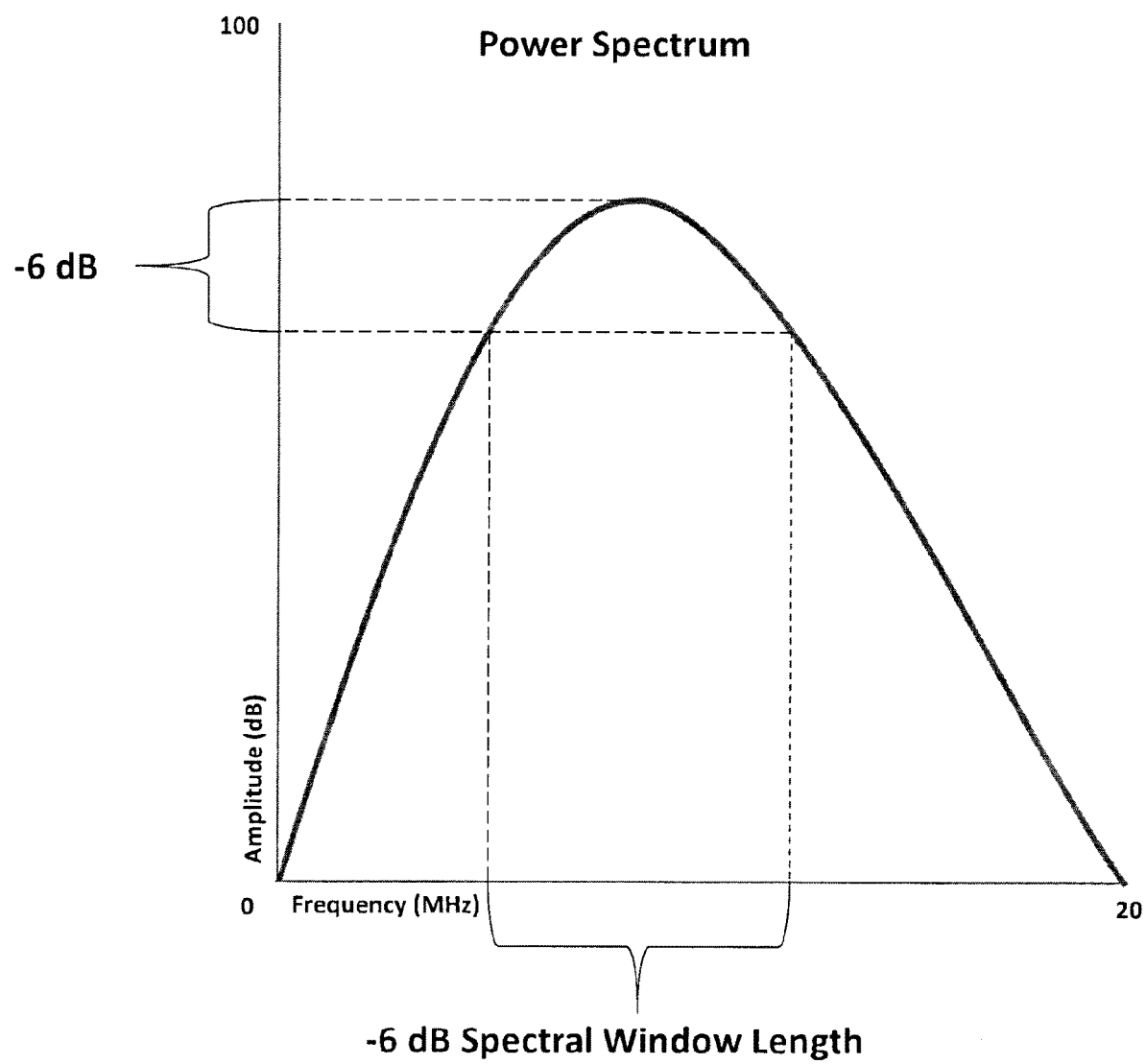
FIG. 37 is another depiction of a data analysis step in accordance with one embodiment of the instant application.

Step 2: The GASP system described in this example computes the power spectrum of the input RF data using the FFT Batch processing capabilities provided by the CUDA development architecture. An exemplary power spectrum in the frequency-domain is shown in FIG. 37. The input data to this processing step is described in Step 1. The output data of this step contains the computation of the Fourier transform for each scan line segment extracted for the Gate in step 1.

Step 3 Pre-Processing: This involves the calculation which may be required prior to the execution of Step 3. In order to perform the windowing of the spectral data, the system requires the start and end indexes of the spectral window being used. The example in this FIG. 37 is a pictorial representation of the calculation of the frequency bandwidth corresponding to a −6 dB window size. Selection of the frequency bandwidth may vary between applications and affect the amount of data processed by the GASP system.

Step 3: The purpose of this step is to calculate the logarithmically compressed power spectra from the FFT output data and extract the desired bandwidth described in the Step 3 pre-processing step. Inputs to this step may include the FFT Output Array, which is a 1D array containing one volumetric gate worth of computed FFT data. FFT data may be ordered by scan line by plane as in FIG. 38.

Figure 38:
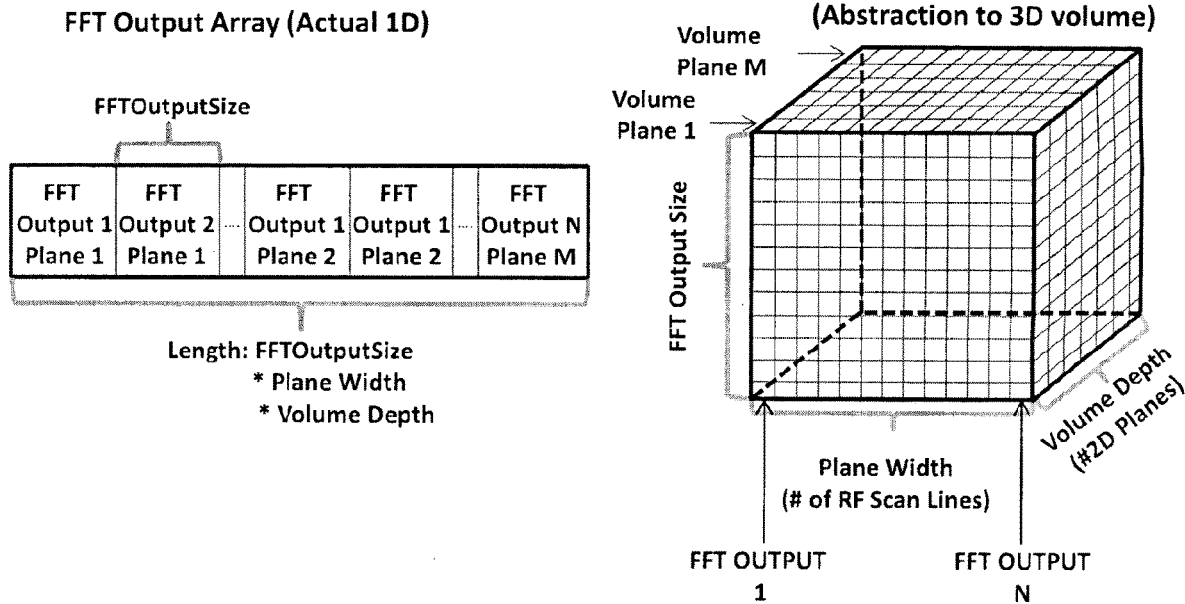
FIG. 38 is another depiction of a data analysis step in accordance with one embodiment of the instant application.

FIG. 38 depicts a visual representation of step 3 (Substep 1/3): This step relates to the generation of an array comprised of a single data array containing the output from the CUDA FFT Batch computations. As before, the individual FFT data are stored in scan line/plane major ordering as depicted in the 3D data abstraction.

Figure 39:
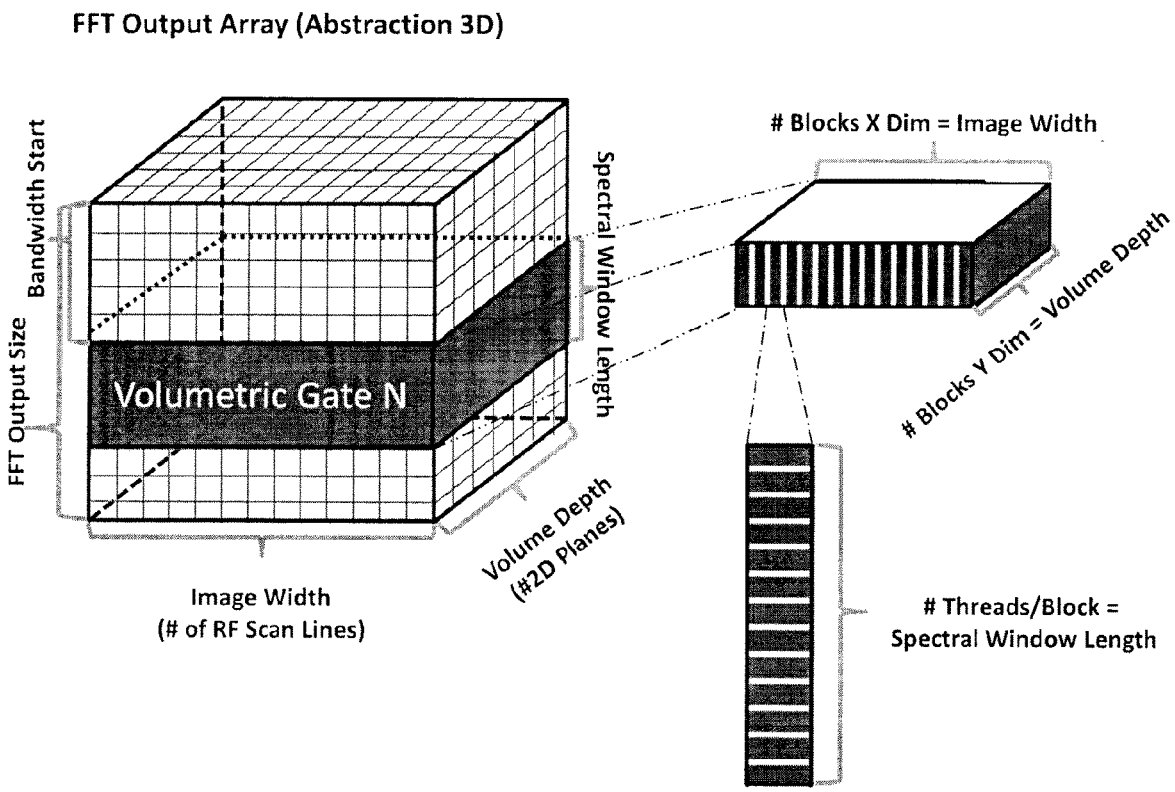
FIG. 39 is another depiction of a data analysis step in accordance with one embodiment of the instant application.

FIG. 39 depicts a visual representation of step 3 (Substep 2/3). A Block of execution threads is executed for lateral scan line across all planes in the computed volume FFT input set. Each block is executed with a Spectral Window Length number of threads. The Spectral Window Length is computed in the Step 3 pre-processing step. In this step, the following parallelization strategy may be used in some embodiments: each FFT processed volumetric gate is processed by an image width by volume depth grid of blocks, each FFT Output is processed by a 1D block of Gate Length # of threads and each thread processes a single RF value are all processed in parallel in the GPU.

FIG. 40 depicts a visual representation of step 3 (Substep 3/3). Each kernel is executed on a GPU SIMD processor and is responsible for copying two data points from the FFTOutput Array (real and imaginary), computing the data point in the logarithmically compressed power spectrum, and saving the result to the required location in the Windowed Power Spectra Array. In this step, a power spectra value is computed from FFT data.

Step 4: The purpose of this step is to calculate an averaged power spectrum for each lateral window across all planes in a single volumetric gate of windowed power spectra. The inputs for Step 4 may include a Windowed Power Spectra (WPS) Data Array (example: −6 dB), which can be characterized as a 1D array containing one volumetric gate worth of windowed power spectra data.

FIG. 41 depicts a visual representation of step 4 (Substep 1/4): This step comprises of a data array containing the logarithmically compressed power spectra output from step 3. As before, individual Spectra are stored in scan line/plane major ordering as depicted in the 3D data abstraction.

FIG. 42 depicts a visual representation of step 4 (2/4). A three dimensional Block of threads is executed, one for each lateral window through a plane, the second for each data point within the spectral window, and the third for each plane in the volume. Each block is executed with a Lateral Window Width number of threads. In this step, the following parallelization strategy may be used in some embodiments: 3D thread Block Grid used, X-Dim for each lateral window, Y-Dim for each point in the power spectra and Z-Dim for each volumetric window are processed in parallel in the GPU. Each thread computes the averaged power spectral point as one data point in one window.

FIG. 43 depicts a visual representation of step 4 (Substep 3/4). The first of two calculations performed for step 4 of the volumetric GASP system. Each kernel is executed on a GPU SIMD processor and is responsible for copying a single data point to a point in shared memory. Some embodiments may characterize a Kernel Step 1 of 2 as the following: copy 1 lateral window width of power spectral values to shared memory (#Blocks(x, y, z)=# Lateral Windows, Spectral Window Length, Volumetric Depth, #Threads(x)=Lateral Window Size).

FIG. 44 depicts a visual representation of step 4 (Substep 4/4). The second of two calculations performed for step 4 of the volumetric GASP system. Once the data points corresponding to a given frequency point are copied to the block shared memory in Step 4(3/4) a reduction operation is performed in order to obtain the average and saved in the corresponding position in the output Averaged Windowed Power Spectra data array. Some embodiments may characterize a Kernel Step 2 of 2 as the following: Perform reduction summation operation to determine averaged value in shared memory array and place averaged value into Averaged Windows Power Spectra (AWPS) output data array.

Step 5: The purpose of this step is to calculate an averaged power spectrum for each volumetric gate across all planes in a single volumetric gate of windowed power spectra. The inputs for this step may include: an Averaged Windowed Power Spectra (AWPS) Array, which is a 1D array containing one volumetric gate worth of averaged windowed power spectra data, wherein spectral data ordered by scan line and volumetric plane as shown in FIG. 45; and a Calibration Windowed Data Array (CWPS) Array, which is a 1D array containing one volumetric gate worth of 3D averaged spectral window data used for normalization.

FIG. 45 depicts a visual representation of step 5 (Substep 1/4). It is comprised of a data array containing the logarithmically compressed window averaged power spectra output from step 4. As before, individual Spectra are stored in window/plane major ordering as depicted in the 3D data abstraction. Additionally, a second input data array containing a previously calculated volumetric window averaged spectral data for a corresponding volumetric gate of calibration data is input.

Figure 46:
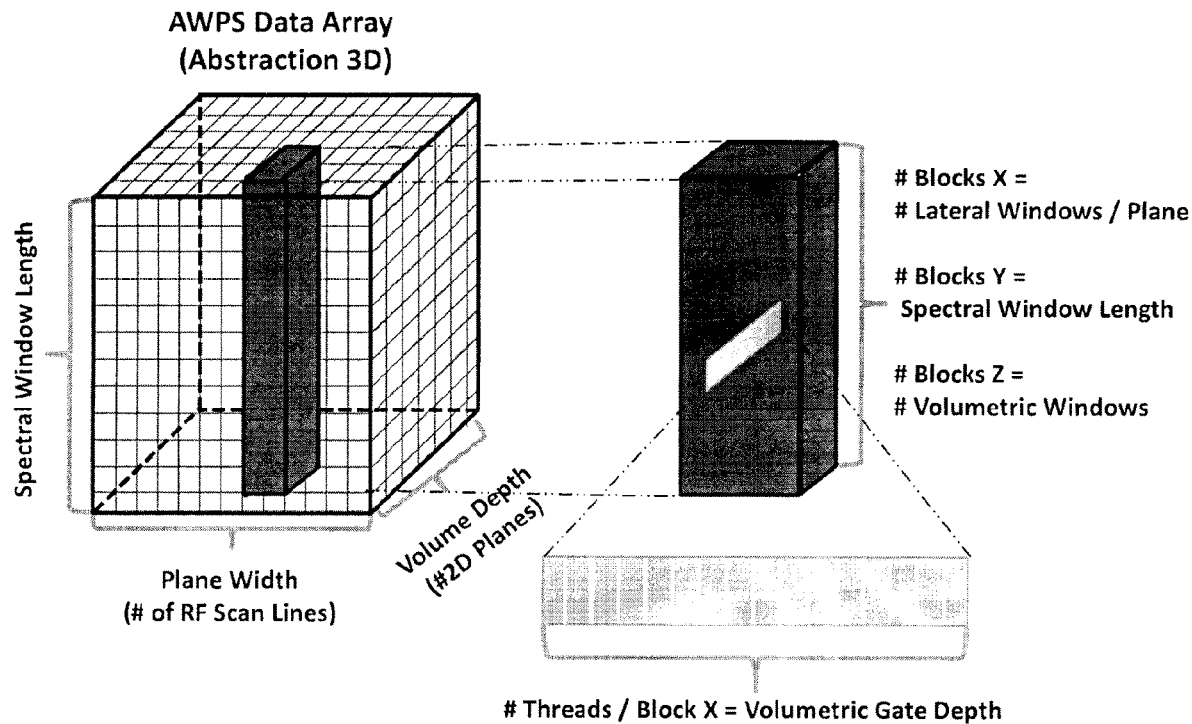
FIG. 46 is another depiction of a data analysis step in accordance with one embodiment of the instant application.

FIG. 46 depicts a visual representation of step 5 (Substep 2/4). A three dimensional Block of threads is executed, one for each lateral window through a plane, the second for each data point within the spectral window, and the third for each volumetric window in the volumetric gate. Each block is executed with a Volumetric Gate Depth number of threads. In this step, the following parallelization strategy may be used in some embodiments: 3D thread Block Grid used, X-Dim for each lateral window, Y-Dim for each point in the power spectra and Z-Dim for each volumetric window, and for each thread the averaged power spectral point for one data point in one volumetric window, may all be processed in parallel.

Figure 47:
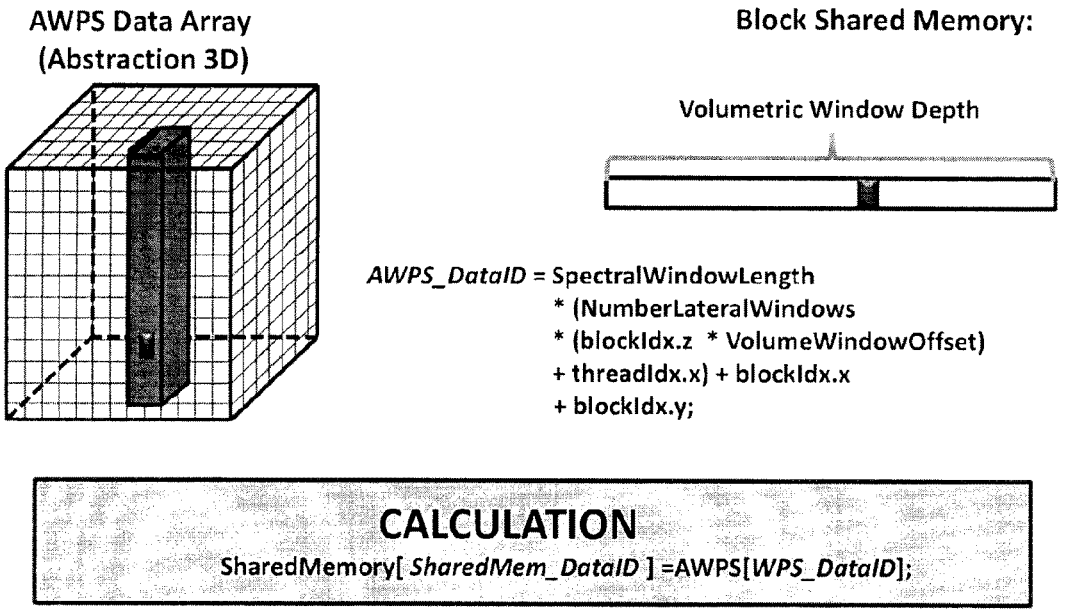
FIG. 47 is another depiction of a data analysis step in accordance with one embodiment of the instant application.

FIG. 47 depicts a visual representation of step 5 (Substep 3/4). Each kernel is executed on a GPU SIMD processor and is responsible for copying a single data point to a point in shared memory. Some embodiments may characterize a Kernel Step 1 of 2 as the following: copy 1 volumetric window depth of averaged power spectral values to shared memory.

FIG. 48 depicts a visual representation of step 5 (Substep 4/4). Once the data points corresponding to a given frequency point are copied to the block shared memory in Step 5 (Substep 3/4), a reduction operation is performed in order to obtain the average and saved in the corresponding position in the output Averaged Windowed Power Spectra data array. Some embodiments may characterize a Kernel Step 2 of 2 in this step as the following: Perform reduction summation operation to determine averaged value in shared memory array and place normalized averaged value into Averaged Windows Power Spectra (AWPS) output data array.

Step 6: This is the sixth and final step in the volumetric GASP system described in this documentation. The purpose of this step is to calculate the best fit line through each of the volumetric averaged spectral windows in the volumetric gate and extract desired spectral parameters. In some embodiments, inputs for this step may include: an Averaged Windowed Power Spectra Array comprising 1D array containing one volumetric gate worth of averaged windowed power spectra data (spectral data ordered by scan line and volumetric plane as shown in FIG. 49 and an X-Axis Frequency Array comprising a 1D array containing Spectral Window Length number of data points, representing the x-axis of the power spectrum data. In embodiments, 2 float values may also serve as input containing the sum of the frequency values as well as the sum of the squares is also input. These may be used in linear regression calculations.

FIG. 49 depicts a visual representation of step 6 (Substep 1/4). It is comprised of a data array containing the volumetric averaged, normalized, windowed and logarithmically compressed power spectra output from step 4. Individual averaged spectra are stored in volumetric window major ordering as depicted in the 3D data abstraction. Additionally, a second array containing the frequency values corresponding to the X-Axis of the power spectra are also provided as input. The previously calculated sum and sum of squares of the array are provided for linear regression calculations.

Figure 50:
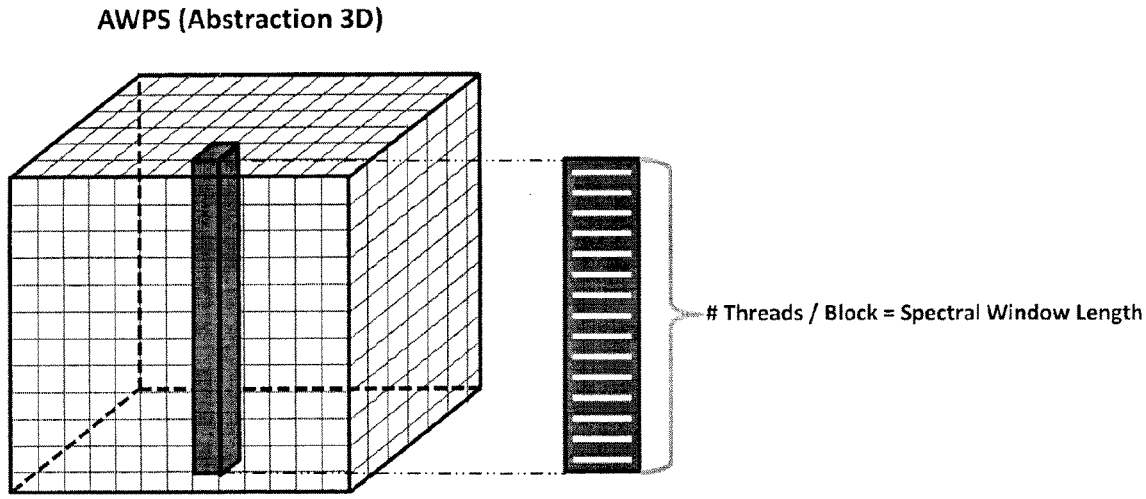
FIG. 50 is another depiction of a data analysis step in accordance with one embodiment of the instant application.

FIG. 50 depicts a visual representation of step 6 (Substep 2/4). A one dimensional Block of threads is executed; one for each volumetric window through the volumetric gate. Each block is executed with a Spectral Window Length number of threads. In this step, the following parallelization strategy may be used in some embodiments: each averaged power spectra is processed by a 1D block of Spectral Window Length # of threads (Base 2 for reduction), and each thread processes a single Power Spectral value, may all be processed in parallel in the GPU.

Figure 51:
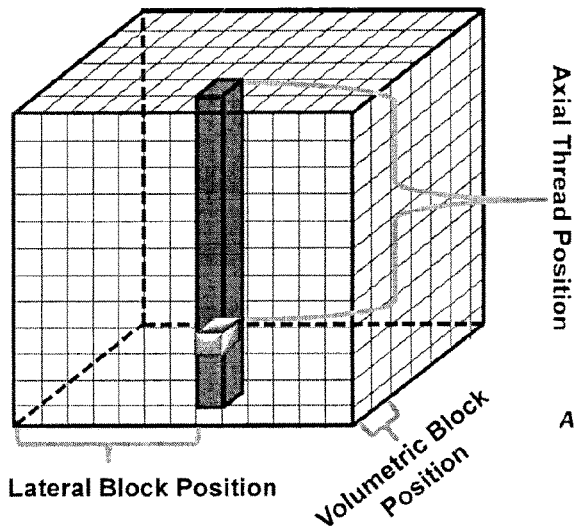
FIG. 51 is another depiction of a data analysis step in accordance with one embodiment of the instant application.

FIG. 51 depicts a visual representation of step 6 (Substep 3/4). Each kernel is executed on a GPU SIMD processor and is responsible for copying a single data point to a point in shared memory as well as multiplying it by the corresponding X-axis input value and copied to second point in shared memory. In some embodiments, the following processing instructions may be applied to any given kernel: copy Window values to shared memory and perform reduction to find 2 required linear regression values ($\Sigma x$ & $\Sigma x^2$ are input parameters), and once values have been obtained, QUS parameters are determined and saved to output array.

FIG. 29, which depicts a visual representation of the analogous step for a 2-dimensional process, equally applies to this step 6 (Substep 4/4). Once the data points corresponding to a given frequency point are copied to the block shared memory locations in Step 5: 3/4, two reduction operations are performed in order to obtain the sums. QUS linear regression parameters are calculated and stored to the corresponding location in the volumetric QUS Parameter output Array. Several example QUS parameters of interest calculations are displayed. In this example, the following parameters may be calculated as follows: Slope=$(N*\Sigma xy-\Sigma x\Sigma y)/N*(\Sigma x^2)-(\Sigma x)^2$, Intercept=$(\Sigma y*\Sigma x)-(\Sigma x*\Sigma xy)/N*(\Sigma x^2)-(\Sigma x)^2$, and MBF=Intercept+slope*x[MBFIndex].

Other statistical methods for determining relationships between variables may be used, and other values may be determined from such analyses that would be known to a person skilled in the art and the subject matter should not be limited to those methods and values disclosed in the foregoing example.

The volumetric gate level parallelization process described herein is not an exhaustive solution to all volumetric QUS data processing requirements, but rather an example of a GASP processing system. This particular process may be scaled based upon application requirements and hardware capabilities to include a given set or subset of volumetric gates, as required by individual QUS processing circumstances. Modifications to this particular GASP implementation include but are not limited to varying hardware RF data outputs as well as alternate spectral processing methods for QUS parameters.

Many of the following terms may be referred to herein:
0 Padding: An application specific range of 0 values padded to RF gate data in order to compute Fourier transforms to desired compute lengths.
Average Spectral Window (ASW): A single Lateral Window of spectral data containing the averaged power spectrum for the window.
Averaged Windowed Power Spectrum (AWPS): A single Lateral Window of spectral data containing the Averaged Windowed Power Spectrum for a single window.
Axial Gate Length: the number of axial data points contained in one gate.

Axial Scan Line Gating: The process of determining and/or extracting the ultrasound backscatter data for individual gate processing.

Bandwidth Frequency Data Array: Data array containing the frequency (X-Axis) data corresponding to the Spectral Frequency Window.

Block: A CUDA thread blocks.

BlockId.x/y/z: CUDA assigned thread identifiers.

Block Shared Memory: GPU memory shared between threads executing in a single Block.

CPU: Central Processing Unit.

FFTComputLength: Desired Fourier transform computation length. Application specific lengths accomplished with 0 padding of RF data.

FFT Output: The result of a single FFT calculation. Typically calculated in batches of multiple outputs.

FFTOutputSize: The number of data points returned from FFT calculations.

FFTOutputSize=(FFTComputeLength/2)+1

Gate: A depth dependent two-dimensional region of ultrasound backscatter data.

Gate Depth: The number of RF data points along a single scan line to the beginning of the desired gate.

Gate Depth=Gate Number*Gate Offset

Gate Length: The number of RF data points along a single scan line through a single gate.

Gate Number: Gates are numbered in increasing order from top to bottom starting at 0.

Gate Offset: The number of data points between individual gate starting depths.

Gate Windowing: The process of ultrasound backscatter data windowing for individual gate data. An example used in this documentation is applying a Hanning window to the ultrasound-related RF data for each individual gate.

GASP: GPU Accelerated Spectral Processing.

GPGPU: General Purpose Programming GPU.

GPU: Graphical Processing Unit.

Image Width: # of lateral RF data scan lines acquired in 2D image.

Image Height: # of axial RF data points per scan line in 2D image.

Lateral Window: Spectral data ranging over a desired number of gated RF scan line data.

Lateral Window Width: The number of computed spectral data lines within a single window.

Lateral Window Offset: The number of spectral data lines between Lateral Windows starting positions.

Lateral Window Spectrum Averaging: Two dimensional spectral data point averaging computation in order to obtain the averaged spectral data used in the generation of QUS parameters for individual QUS windows.

MBFIndex: The index used in the calculation of the MBF parameter. Represents the frequency at which the MBF is calculated using appropriate slope and intercept values.

Plane (Image Plane): A two-dimensional set of ultrasound backscatter data.

Plane Height: # of axial RF data points per scan line in two dimensional set of ultrasound backscatter data.

Plane Width: # of lateral RF data scan lines in two-dimensional set of ultrasound backscatter data.

QUS: Quantitative Ultrasound

QUS Parameter Array: A data array output containing data representing a single QUS parameter for each Lateral Window calculated in a single gate.

RF: Radiofrequency.

Sector: The percentage of the image/plane width acquired in an ultrasound backscatter data set.

SIMD: Single Instruction Multiple Data.

Spectral Frequency Window: The data points ranging within a desired window range. A −6 dB window is used as a common example.

Spectral Window Data Point Average: The average spectral value for a single spectral data point contained within an averaged spectral window.

Spectral Window Length: The number of data points contained within the Spectral Frequency Window.

Ultrasound Tissue Characterization (UTC): A scientific field of study which employs Quantitative Ultrasound analysis to discern various tissue features.

QUS Window: Two dimensional spectral data used to determine QUS parameters comprised of spectra computed from individual ultrasound backscatter scan lines.

Windowed Power Spectra (WPS): Power spectral data found within the Spectral Frequency Window.

Threads: CUDA kernel execution threads.

ThreadIdx.x/y: CUDA assigned thread identifiers.

Volume Depth: The number of two-dimensional Planes of ultrasound backscatter data contained within a volume of ultrasound data.

Volumetric Gate: A depth dependent three-dimensional region of ultrasound backscatter data.

Volumetric Spectrum Averaging: Spectral data point averaging computation in order to obtain the averaged spectral data used in the generation of QUS parameters for individual volumetric gates.

Any references herein or in any Figures to "SOA" refers to prior art.

Some additional examples of QUS post processing methods used in tissue characterization applications are:

AI Methods and Classification Processes:

Neural Networks and Support Vector Machines used in research.

Tree Classifiers used in research and patented by Volcano Crop.

Statistical QUS Analysis:

Texture analysis of QUS parameters: A statistical image processing method of determining information from an image.

Example in breast cancer treatment monitoring.

In addition, there are some alternative QUS parameter calculations using GASP. This includes testing done to date computes linear regression parameters from calculated power spectra. This represents the last step in the GASP process which computes the QUS parameters. There are additional parameters and methods of analysing the Spectral data and obtaining information from it. Based on the examples herein, QUS information may be achieved at increased processing speeds and may encompass many QUS analysis techniques.

In some embodiments, the GASP system described herein may employs a post-processing paradigm used to demonstrate the accelerated QUS parameter processing which may be achieved by parallelizing QUS processes, GASP may nevertheless be applied to process real-time data streams and achieve real-time QUS imaging. The results of the GASP system demonstrated herein and testing indicate that multi-frame/second QUS image processing is possible.

A framework for developing a parallelized process to real-time ultrasound data processing is provided. Multiple FFT calculations and gate processing kernel are functions that are highly parallelized.

Given that QUS parameters may be processed in multi-frame/second rates means in many cases the limiting factor is the data stream to the GASP system. An online service may be created allowing users to send ultrasound data via the internet or other networks, and return QUS processed data. This may provide for distance analysis when, for example, ultrasound transducers are remotely located; as well as for automated tissue characterization for a widely distributed set of patients or specimen, with a centrally-located and automated response data storage facility.

The GASP system demonstrated herein was developed using CUDA developed by NVIDIA. NVIDIA is an industry leader in GPGPU development, by providing both hardware and software development architectures. There are alternatives to CUDA for the programming of SIMD processor architectures, such as OpenCL which may be programmed for Video Cards manufactured by competitors to NVIDIA. The use of GPU described herein should extend to all SIMD devices.

EXAMPLES

This section contains experimental data resulting from experiments performed in calculating QUS parameters from an ultrasound-related RF data set and comparing the present system with current systems. The steps, data and processing methodologies of the instantly disclosed subject matter are not meant to represent exhaustive or optimal solutions to either approach, but rather to demonstrate effective implementations of the data processing steps described below using prior art (as a comparison) and GASP implementations, highlighting the acceleration in processing capable through a highly parallelized processing method.

Tests were conducted using the following hardware and software:
  Computer: Operating System: Microsoft Windows 7 Professional x64
  CPU: Intel® Core™ i7 CPU Q740 @1.73 GHZ
  RAM: 8 GB
  Video Card: NVIDIA GEForce GTX 770M
  Prior art implementation (CPU): Matlab R2013b
  GASP implementation: Microsoft Visual Studio 2010, CUDA Version 5.5

An ultrasound-related RF data set with the following acquisition parameters was employed for all tests:
  RF Image Data:
    Image Width: 256 RF Data Scan Lines/Frame
    Image Height: 1040 data points/Scan Line
    Sampling Frequency: 20 MHz Each of the tests below was conducted on the same data set. Each individual test was conducted by maintaining all QUS calculation parameters constant and investigating the effects of altering a single parameter upon calculation performance. Test results are displayed as the average amount of time measured to process the entire RF data set indicated above, with the GASP data indicating the average after 100 iterations and the CPU Matlab data indicating the average after 10 iterations. Parameters which were selected are representative of data processing settings which may vary between QUS and tissue characterization applications and hardware. It is not however, meant to be an exhaustive list of calculation parameters which can change between tissue characterization applications or hardware.

Example 1: Gate Length Test

This set of experiments was conducted with the following QUS image parameterization settings:

| | |
|---|---|
| FFTComputeLength | 4096 |
| Spectral Window Length | 615 |
| Gate Length | VARIABLE |
| Gate Offset | 20 |
| Lateral Window Width | 32 |
| Lateral Window Offset | 1 |

In this test, all parameters remained constant with the exception of the gate length. This parameter represents the amount of RF data which is included in a single gate depth. This parameter was selected as it is representative of a parameter which would be expected to vary between QUS applications and hardware requirements.

Figure 53:
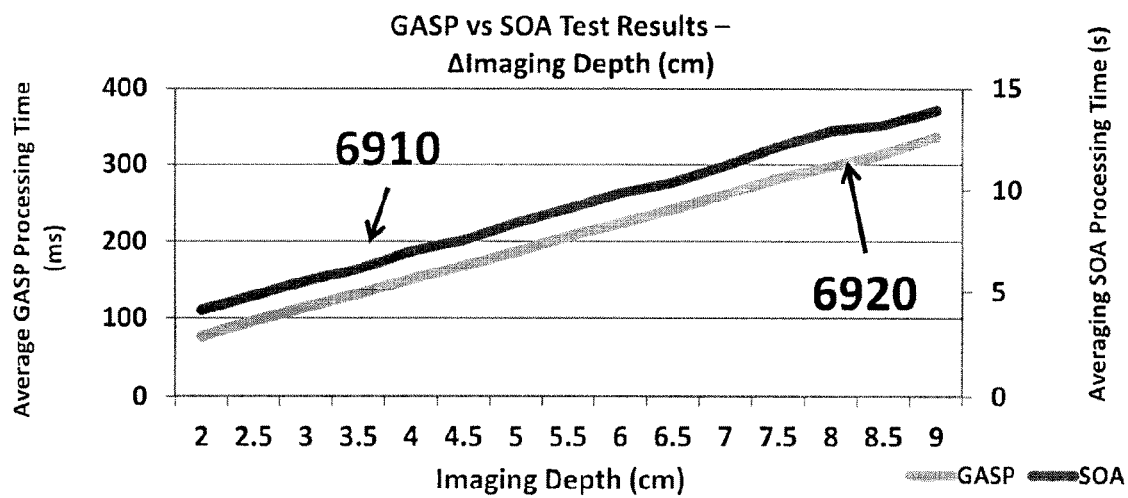
FIG. 53 is a graphical indication of performance in accordance with one embodiment of the instant application.

Results obtained from the variable Gate Length of Example 1 is shown in FIG. 53, as a comparison between the processing results of an embodiment of the disclosed subject matter 6920 and a CPU-based system (i.e. prior art) 6910. Obtained data highlights the increase in processing speeds obtained through the GASP implementation. Results were completed in the order of seconds with existing technology vs. milliseconds with GASP.

Example 2: Lateral Window Offset Test

This set of experiments was conducted with the following QUS image parameterization settings:

| | |
|---|---|
| FFTComputeLength | 4096 |
| Spectral Window Length | 615 |
| Gate Length | 120 |
| Gate Offset | 20 |
| Lateral Window Width | 32 |
| Lateral Window Offset | VARIABLE |

Figure 54:
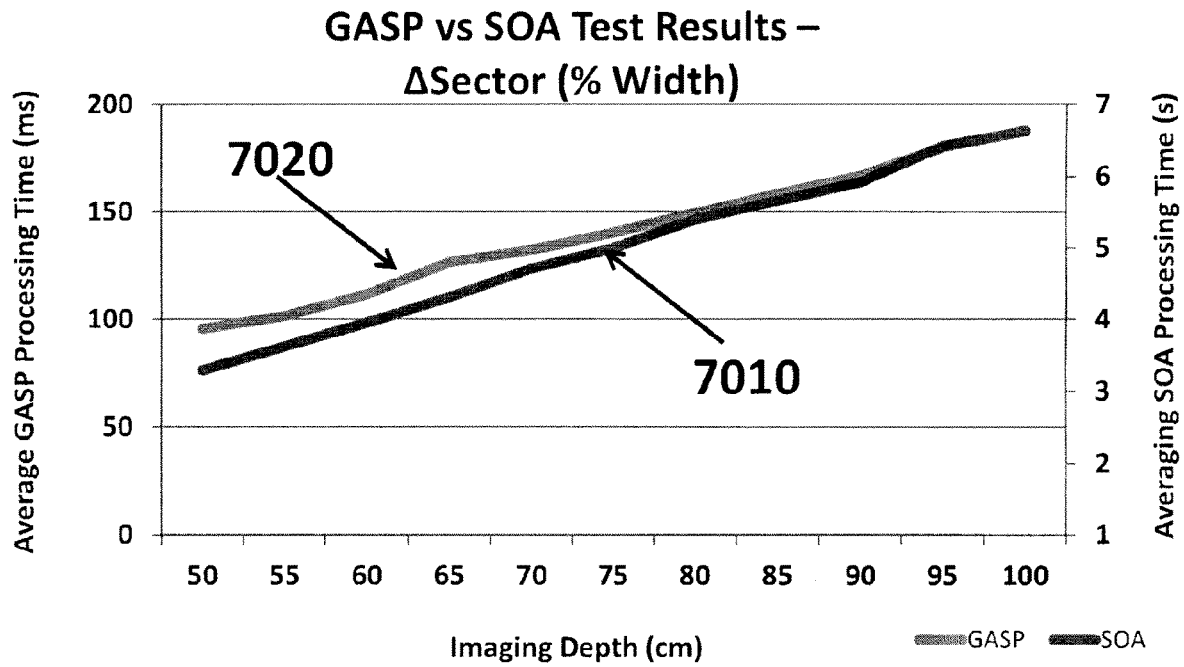
FIG. 54 is a graphical indication of performance in accordance with one embodiment of the instant application.

In this test, all parameters remained constant with the exception of the lateral window offset. This parameter represents the number of scan lines between lateral windows and thus affects the total number of windows processed for the data set. This parameter was selected as it is representative of a parameter which would be expected to vary between QUS applications and hardware requirements. Results obtained from the variable Lateral Window Offset, Example 2, are shown in FIG. 54, as a comparison between the processing results of an embodiment of the disclosed subject matter 7010 and a CPU-based system (i.e. prior art) 7020. Obtained data highlights the increase in processing speeds obtained through the GASP implementation. Results were completed in the order of seconds with existing technology vs. milliseconds with GASP.

Example 3: FFTComputeLength Test

This set of experiments was conducted with the following QUS image parameterization settings:

| | |
|---|---|
| FFTComputeLength | VARIABLE |
| Spectral Window Length | VARIABLE |
| Gate Length | 120 |
| Gate Offset | 20 |
| Lateral Window Width | 32 |
| Lateral Window Offset | 2 |

Figure 55:
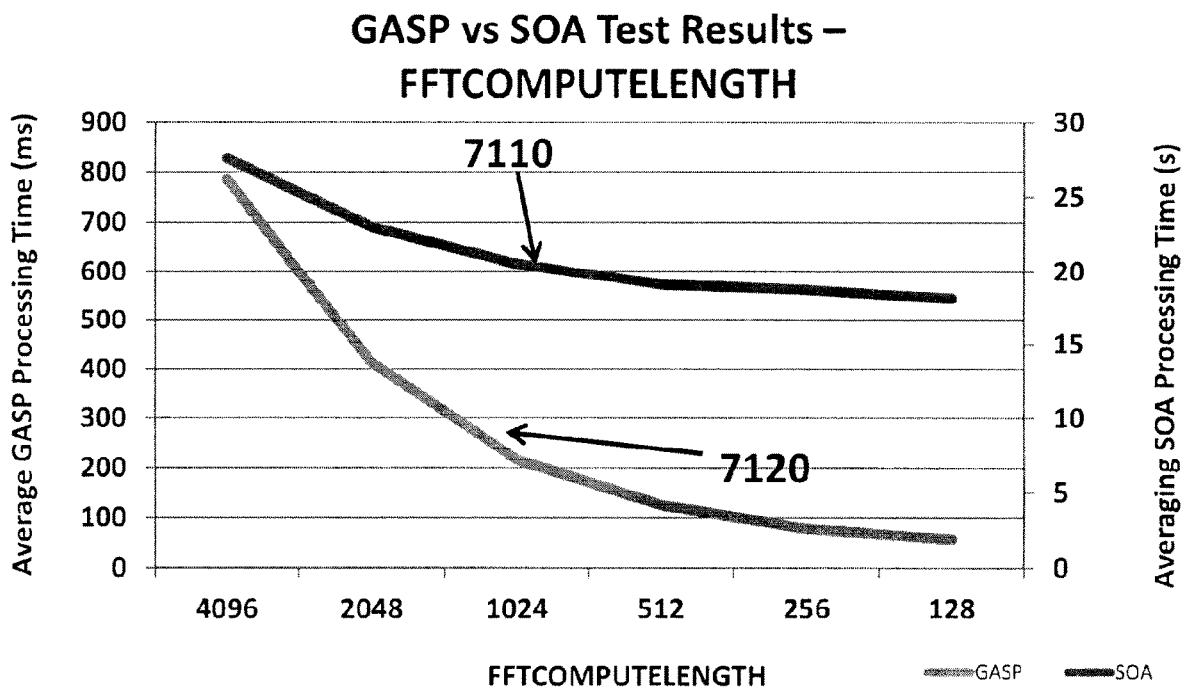
FIG. 55 is a graphical indication of performance in accordance with one embodiment of the instant application.
Figure 56:
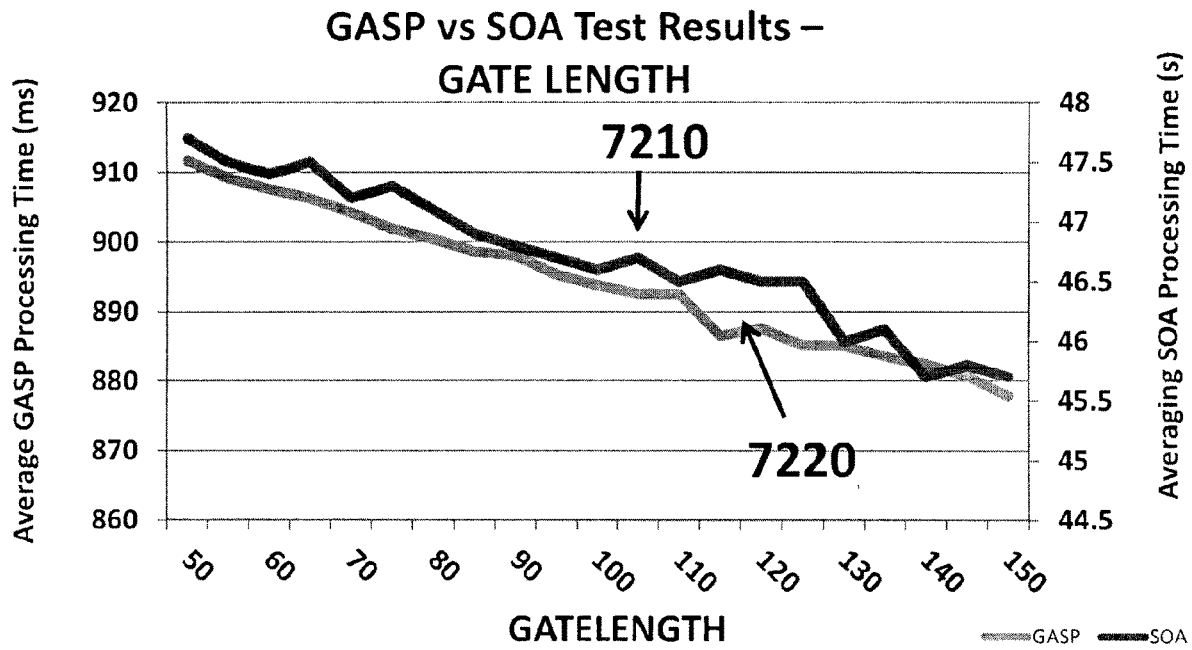
FIG. 56 is a graphical indication of performance in accordance with one embodiment of the instant application.
Figure 57:
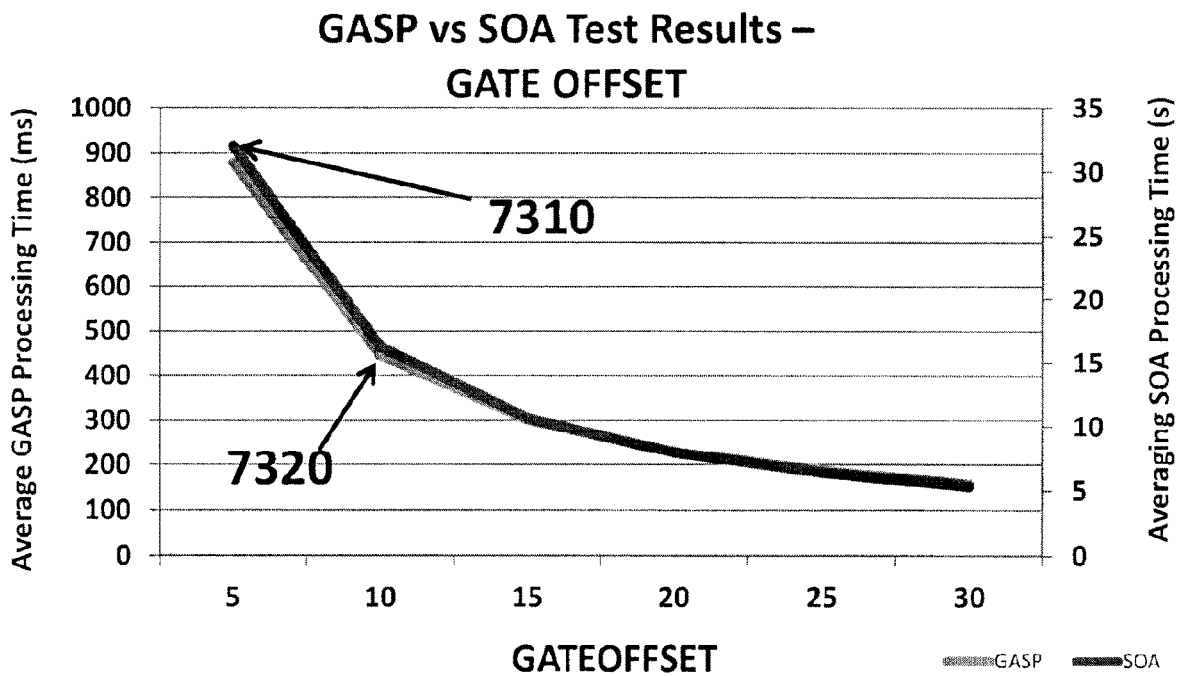
FIG. 57 is a graphical indication of performance in accordance with one embodiment of the instant application.
Figure 58:
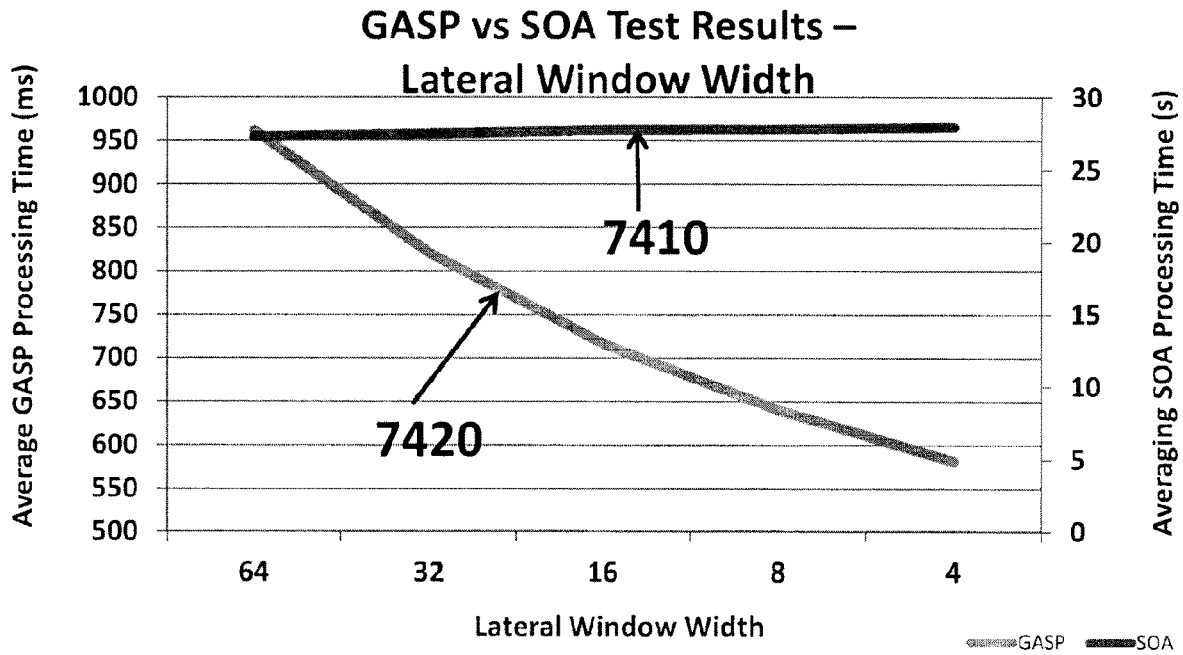
FIG. 58 is a graphical indication of performance in accordance with one embodiment of the instant application.
Figure 59:
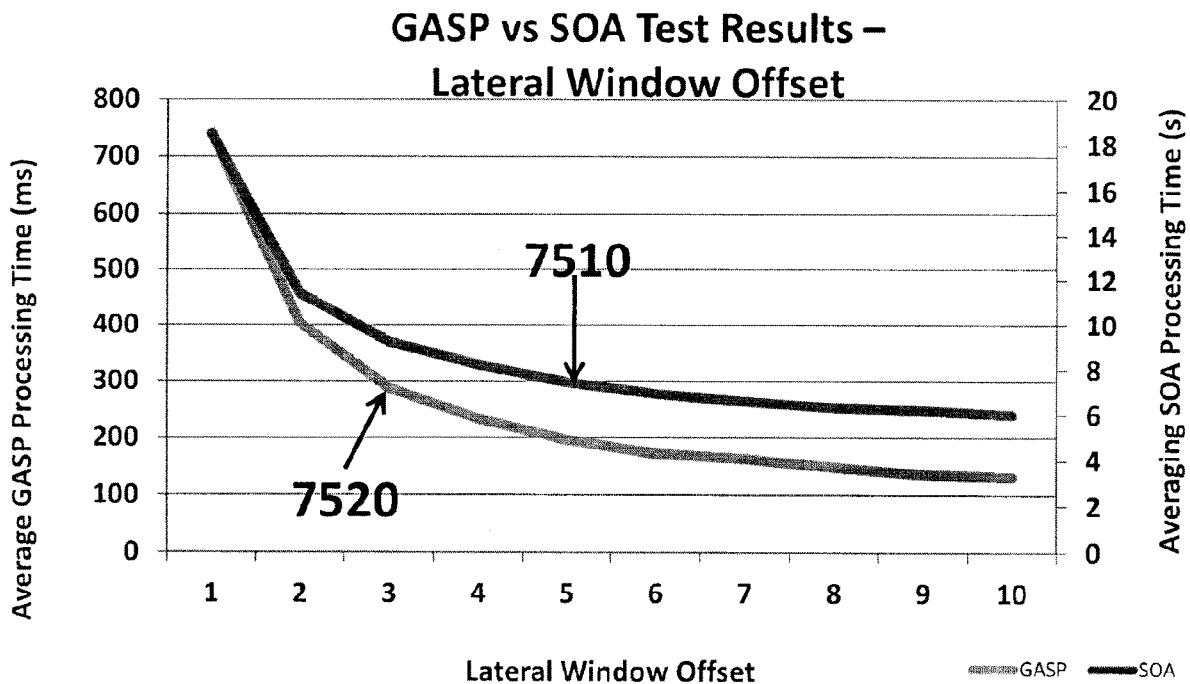
FIG. 59 is a graphical indication of performance in accordance with one embodiment of the instant application.

In this test, all parameters remained constant with the exception of the FFTComputeLength and spectral window length. This parameter represents the Fourier Transform computation length and thus affects the FFT computations and amount of data being processed by the GASP system. This parameter was selected as it is representative of a parameter which could vary between QUS applications and hardware requirements. Results obtained from the variable FFTComputeLength and spectral window length, Example 3, are shown in FIG. 55, as a comparison between the processing results of an embodiment of the disclosed subject matter 7120 and a CPU-based system (i.e. prior art) 7110. Obtained data highlights the increase in processing speeds obtained through the GASP implementation. Results were completed in the order of seconds with existing technology vs. milliseconds with GASP.

As may be seen from the above examples, implementation of the present system and method results in increased processing speed of the data, when compared to the prior art. Additional testing results having various parameters of the subject matter disclosed herein are shown in FIGS. 56 to 59 as a comparison between the processing results of embodiments of the instantly disclosed subject matter (respectively, 7220, 7320, 7420, and 7520 in FIGS. 55 through 59) and CPU-based systems (respectively, 7210, 7310, 7410, and 7510 in FIGS. 55 through 59) (i.e. prior art).

Real-Time Remote Implementation Example

Figure 52:
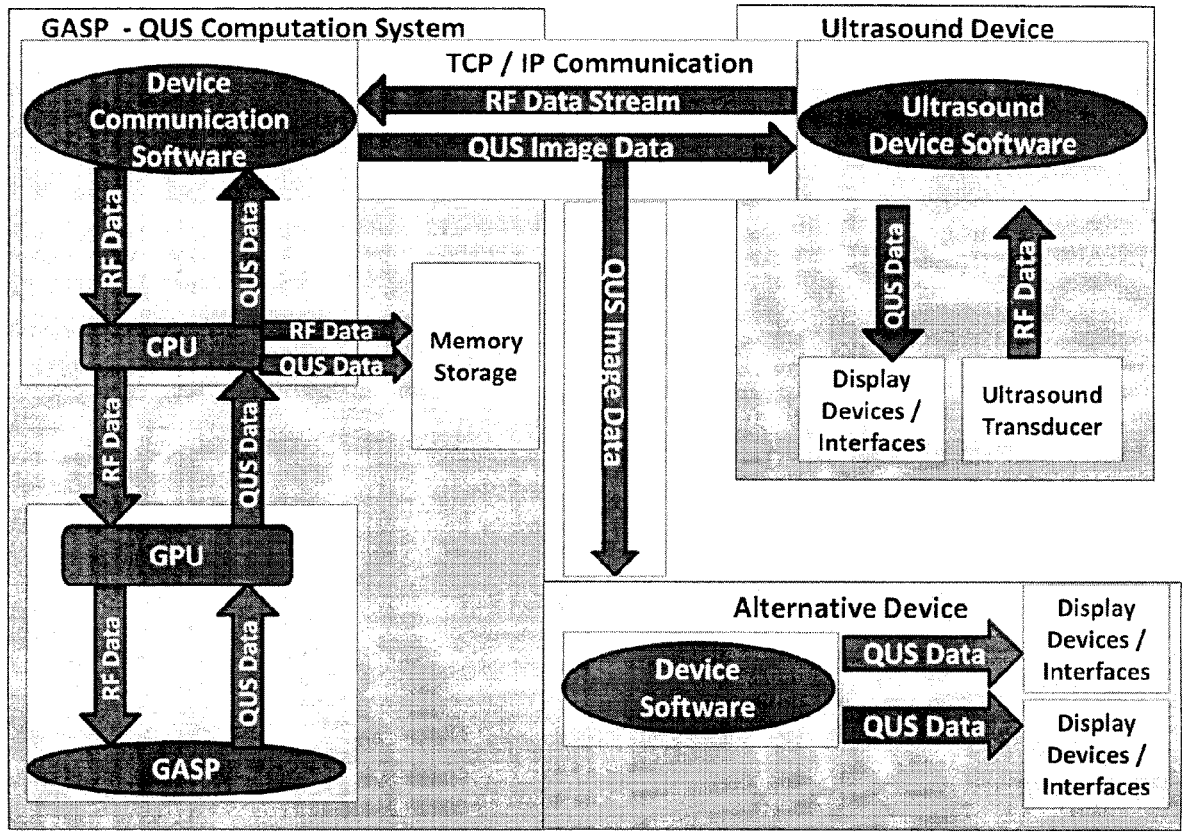
FIG. 52 is a depiction of a real-time remotely utilized system in accordance with an embodiment of the disclosed subject matter.

In order to demonstrate the capacity of a GASP system in processing QUS data from ultrasound backscatter data for the purposes of ultrasound tissue characterization in conjunction with data acquisition, a prototype system was designed, constructed, and tested. The computing system interfaces with an ultrasound device, and acquires ultrasound radiofrequency data in conjunction with data acquisition. A GASP processing engine (i.e. PPU) was incorporated and tested which implements the GASP system architecture disclosed herein. A simple schematic of the prototype system architecture and data communication pathway are pictorially demonstrated in FIG. 52.

In this exemplary embodiment, the prototype system interfaces with an Ultrasonix Touch imaging device manufactured by Analogics Inc., and was tested using an L14-5W imaging transducer. The device software interface version of 6.0.7 was employed as well as a corresponding Ulterius communication library. RF data is sent via TCP/IP connection in single frames of data, which in turn are processed employing the GASP QUS parameter processing system to determine user selected QUS parameters of interest. The prototype system allows for basic command and control of data acquisition and GASP processing parameters, saving of parameters to local memory storage as well as image display capabilities. Image display options have been developed which return a processed QUS image via TCP/IP communication protocols to the device software for display in the device software interface allowing for local real-time data processing. This is accomplished employing the Ulterius image injection functionality which allows for remote image injection to the device interface. The system has also been designed to display the resulting QUS images to alternative devices via TCP/IP protocols as well as to the prototype interface itself.

The prototype system was designed to demonstrate the capabilities of the GASP processing system and how it can be extended to encompass real-time, near real-time and online tissue characterization technologies. The system interfaces with an ultrasound imaging device and obtains real-time RF data during data acquisition. The tests conducted demonstrate the capacity for multi-frame per second QUS parameter processing speeds at various clinically relevant acquisition and computation settings. By employing a TCP/IP communication protocol between the GASP real-time prototype system and the ultrasound acquisition device, the system demonstrates the capabilities required for multi-frame per second online QUS parameter calculation and image display. This allows for GASP based tissue characterization technologies to be developed which employ remote calculation and display of calculated QUS parameters.

The prototype and any of its aspects including but not limited to architecture, hardware, GASP implementation, QUS Analysis methodology or analytical parameters, ultrasound device and ultrasound device communication software are not meant to be exhaustive solutions to all QUS requirements. This is meant to be a demonstration of GASP system capabilities for processing QUS parameters for the purpose of ultrasound tissue characterization.

It is to be understood that the above description is intended to be illustrative, and not restrictive. Many other embodiments will be apparent to those skilled in the art, upon reviewing the above description. The scope of the disclosure should, therefore, be determined with reference to the appended claims, along with the full scope of equivalents to which such claims are entitled.

As many changes can be made to the preferred embodiment without departing from the scope thereof; it is intended that all matter contained herein be considered illustrative and not in a limiting sense.

Although the present disclosure has been described with reference to specific exemplary embodiments, it will be evident that various modifications and changes may be made to these embodiments without departing from the broader spirit and scope of the disclosed subject matter as defined by the appended claims.

What is claimed is:

1. A spectral based quantitative ultrasound (QUS) system for microstructure characterization of a specimen, the system comprising:
   an ultrasound transducer operable to transmit ultrasound signals into the specimen along multiple adjacent scan lines extending axially within the specimen, and collect returned ultrasound signals therefrom and generate RF signals based on said returned ultrasound signals, wherein said RF signals are associated with respective ones of said scan lines to represent a characteristic of the specimen at each of multiple locations within the specimen along each of said scan lines; and
   a parallelizable processing unit communicatively coupled to said ultrasound transducer and operable to concurrently compute from said RF signals respective QUS values representative of said characteristic for each of a plurality of said multiple locations in parallel, wherein successive parallel outputs of said respective QUS values are characteristic of the specimen along each of said multiple scan lines.

2. The system of claim 1, wherein the successive parallel outputs are automatically combined to generate an array of said respective QUS values, said array comprising array elements each having a signal value associated with the RF signals associated with returned ultrasound signals collected from a given one of the multiple locations in the specimen.

3. The system of claim 2, wherein an image is generated from a plurality of pixels, each pixel deriving a pixel value from corresponding one or more array elements.

4. The system of claim 1 or 2, wherein the parallelizable processing unit is a graphics processing unit (GPU).

5. The system claim 4, wherein the graphics processing unit is configured for general purpose programming graphics processing unit (GPGPU).

6. The system of claim 4, wherein the GPU utilizes an SIMD architecture.

7. The system of claim 1, wherein a time-based signal window is measured from each of a plurality of sets of RF signals, each said set of RF signals associated with returned ultrasound signals collected from at least one of a group of adjacent locations along one or more of said scan lines.

8. The system of claim 7, wherein a distribution function is applied to each time-based signal window.

9. The system of claim 8, wherein the distribution function is a Hann window function.

10. The system of claim 7, wherein a frequency-based signal indicator is determined from at least some of the said time-based signal windows.

11. The system of claim 10, wherein the frequency-based signal indicator is calculated from a Fourier transform.

12. The system of claim 11, wherein the Fourier transform is a fast Fourier transform.

13. The system of claim 7, wherein at least one further signal parameter is determined from each said frequency based signal indicator.

14. The system of claim 13, wherein said at least one further signal parameter is selected from the following group: a regression-based slope, a regression-based intercept, a mid-band best fit, and a combination thereof.

15. The system of claim 1, wherein a region of the specimen being characterized is a 2-dimensional plane.

16. The system of claim 1, wherein a region of the specimen being characterized is a 3-dimensional volume.

17. A method of real-time spectral based quantitative ultrasound (QUS) calculation of a specimen microstructure across a region of a specimen, the specimen being subjected to ultrasound signals along one or more scan lines, the method comprising:
   associating RF signals generated from returned ultrasound signals from the specimen with respective locations along the one or more scan lines;
   providing to a parallelizable processing unit, in response to an initiating data request, a plurality of raw signal data, each of said raw signal data uniquely associated with the respective locations
   calculating, in parallel in said parallelizable processing unit, a plurality of QUS parameter values, each of said QUS parameter values associated with at least one of said raw signal data from a group of one or more adjacent respective locations along one or more of the one or more scan lines; and
   generating, in a communicatively coupled data storage medium, a data array of QUS parameter values, each of said QUS parameter values in said data array being indicative of a characteristic of the specimen at the at least one location associated with the returned ultrasound RF signals used to calculate that QUS parameter value.

18. The method of claim 17, wherein the parallelizable processing unit is a GPU.

19. The method of claim 17, wherein the QUS parameter value is selected from the following group: a time-base signal window, a frequency-based signal indicator, a spectral value resulting from regression-based analysis, and a combination thereof.

20. The method of claim 19 further comprising generating an image from said data array, wherein the image comprises a plurality of pixels, each said pixel based on a data array element corresponding to a given location in the region of the specimen.

21. The method of claim 17, wherein the region is one of a plane or a volume.

22. A parallelizable processing device for simultaneously calculating a plurality of spectral based quantitative ultrasound (QUS) values representative of a microstructure region of a specimen, said parallelizable processing unit configured to receive a plurality of RF signals collected from an ultrasound analysis of said region, each RF signal associated with respective axial scan lines in said specimen representative of a characteristic of the specimen at each of multiple locations within the specimen along each of said axial scan lines, said parallelizable processing device comprising:
   a data bus configured to accept a plurality of data values associated with said RF signals, each respective data value relating to a given RF signal based on an ultrasound signal from a given location in said specimen;
   a data storage medium configured to store said plurality of data values and, upon a data request, provide at least some of said plurality of data values; and
   a parallel processing unit, said parallel processing unit comprising a plurality of processors, said processors for concurrently performing the same analysis function in parallel on each of said provided data values.

23. The device of claim 22, wherein the analysis function provides a time-based signal window from one or more provided data values from a group of adjacent locations.

24. The device of claim 22, wherein the analysis function provides a frequency-based signal indicator.

25. The device of claim 24, wherein the analysis function further provides regression-based parameter values from said frequency based signal indicator.

26. The system of claim 5, wherein the GPU utilizes an SIMD architecture.

27. The system of claim 4, wherein a time-based signal window is measured from each of a plurality of sets of RF signals, each said set of RF signals associated with returned ultrasound signals collected from at least one of a group of adjacent locations along one or more of said scan lines.

* * * * *